(12) United States Patent
Kling et al.

(10) Patent No.: US 8,906,941 B2
(45) Date of Patent: *Dec. 9, 2014

(54) CARBOXAMIDE COMPOUNDS AND THEIR USE AS CALPAIN INHIBITORS

(75) Inventors: Andreas Kling, Mannheim (DE); Helmut Mack, Ludwigshafen (DE); Katja Jantos, Mannheim (DE); Achim Moeller, Grunstadt (DE); Wilfried Hornberger, Neustadt (DE); Charles W. Hutchins, Green Oaks, IL (US)

(73) Assignees: AbbVie Inc., North Chicago, IL (US); AbbVie Deutschland GmbH & Co. KG, Wiesbaden (DE)

( * ) Notice: Subject to any disclaimer, the term of this patent is extended or adjusted under 35 U.S.C. 154(b) by 837 days.

This patent is subject to a terminal disclaimer.

(21) Appl. No.: 12/708,662

(22) Filed: Feb. 19, 2010

(65) Prior Publication Data

US 2010/0216844 A1 Aug. 26, 2010

Related U.S. Application Data

(60) Provisional application No. 61/154,118, filed on Feb. 20, 2009, provisional application No. 61/289,772, filed on Dec. 23, 2009.

(51) Int. Cl.
| | | |
|---|---|---|
| C07D 277/30 | (2006.01) |
| C07D 417/04 | (2006.01) |
| C07D 417/02 | (2006.01) |
| C07D 413/04 | (2006.01) |
| C07D 401/04 | (2006.01) |
| C07D 401/02 | (2006.01) |
| A61K 31/4439 | (2006.01) |
| A61P 25/28 | (2006.01) |

(52) U.S. Cl.
CPC ............ C07D 401/04 (2013.01); C07D 277/30 (2013.01); C07D 417/04 (2013.01); C07D 413/04 (2013.01)
USPC ..... 514/338; 514/341; 546/270.1; 546/272.7; 546/273.4

(58) Field of Classification Search
CPC .. C07D 277/30; C07D 417/04; C07D 413/04; C07D 401/02; C07D 401/04; A61K 31/4439; A61P 25/28
See application file for complete search history.

(56) References Cited

U.S. PATENT DOCUMENTS

| | | | |
|---|---|---|---|
| 6,103,720 A | 8/2000 | Lubisch et al. |
| 6,380,220 B1 | 4/2002 | Lubisch et al. |
| 6,436,925 B1 | 8/2002 | Lubisch et al. |

(Continued)

FOREIGN PATENT DOCUMENTS

| | | |
|---|---|---|
| CA | 2328720 | 10/1999 |
| WO | 95/07271 | 3/1995 |

(Continued)

OTHER PUBLICATIONS

Hornberger et al., caplus an 2009:822183.*

(Continued)

*Primary Examiner* — Sun Jae Yoo
(74) *Attorney, Agent, or Firm* — Lisa V. Mueller; Michael Best & Friedrich LLP

(57) ABSTRACT

The present invention relates to novel carboxamide compounds and their use as a medicament. The carboxamide compounds are inhibitors of calpain (calcium dependant cysteine proteases). The invention therefore also relates to the use of these carboxamide compounds for treating a disorder associated with an elevated calpain activity and to a method for the therapeutic and/or prophylactic treatment by administering an effective amount of at least one of these carboxamide compounds.

The carboxamide compounds are compounds of the general formula I

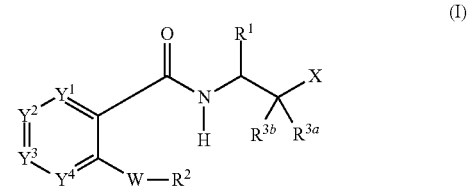

in which
W—$R^2$ is selected from

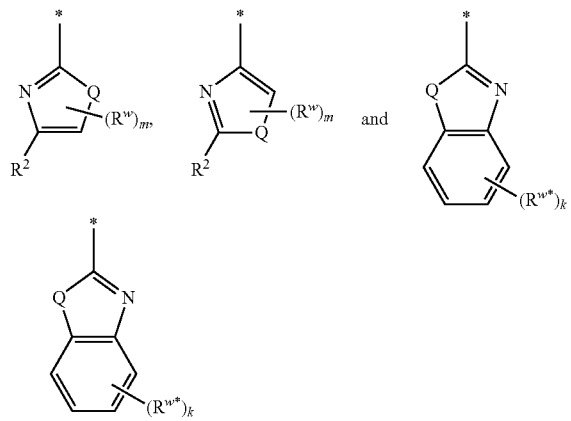

and $R^1$, $R^2$, $R^{3a}$, $R^{3b}$, $Y^1$, $Y^2$, $Y^3$, $Y^4$, X, Q, m, k, $R^w$ and $R^{w*}$ have the meanings mentioned in the claims, the tautomers thereof and the pharmaceutically suitable salts thereof. Of these compounds those are preferred wherein $Y^1$, $Y^2$, $Y^3$ and $Y^4$ are $CR^y$, or one or two of the variables $Y^1$ to $Y^4$ are a nitrogen atom and the remaining variables are $CR^y$, wherein the radicals $R^y$ may be identical or different and have the meanings mentionend in the claims.

26 Claims, No Drawings

(56) References Cited

U.S. PATENT DOCUMENTS

| | | |
|---|---|---|
| 6,436,949 B1 | 8/2002 | Lubisch et al. |
| 6,448,254 B1 | 9/2002 | Lubisch et al. |
| 6,482,832 B1 | 11/2002 | Lubisch et al. |
| 6,562,827 B1 | 5/2003 | Lubisch et al. |
| 6,630,493 B1 | 10/2003 | Lubisch et al. |
| 6,753,327 B1 | 6/2004 | Lubisch et al. |
| 7,511,013 B2 | 3/2009 | Molino et al. |
| 7,514,068 B2 | 4/2009 | Tung |
| 7,521,421 B2 | 4/2009 | Naicker et al. |
| 7,528,131 B2 | 5/2009 | Persichetti et al. |
| 7,531,685 B2 | 5/2009 | Czarnik |
| 7,534,814 B2 | 5/2009 | Ascher et al. |
| 7,538,189 B2 | 5/2009 | Naicker et al. |
| 7,728,012 B2 * | 6/2010 | Kling et al. .............. 514/341 |
| 2009/0082471 A1 | 3/2009 | Czarnik |
| 2009/0088416 A1 | 4/2009 | Czarnik |
| 2009/0093422 A1 | 4/2009 | Tung et al. |
| 2009/0105147 A1 | 4/2009 | Masse |
| 2009/0105307 A1 | 4/2009 | Galley et al. |
| 2009/0105338 A1 | 4/2009 | Czarnik |
| 2009/0111840 A1 | 4/2009 | Herold et al. |
| 2009/0118238 A1 | 5/2009 | Czarnik |
| 2009/0131363 A1 | 5/2009 | Harbeson |
| 2009/0131485 A1 | 5/2009 | Liu et al. |
| 2009/0137457 A1 | 5/2009 | Harbeson |
| 2011/0059968 A1 * | 3/2011 | Hornberger et al. ....... 514/235.5 |

FOREIGN PATENT DOCUMENTS

| | | |
|---|---|---|
| WO | 97/10223 | 3/1997 |
| WO | 98/16512 | 4/1998 |
| WO | 98/25883 | 6/1998 |
| WO | 98/25899 | 6/1998 |
| WO | 99/54294 | 10/1998 |
| WO | 99/17775 | 4/1999 |
| WO | 99/54293 | 10/1999 |
| WO | 99/54304 | 10/1999 |
| WO | 99/54305 | 10/1999 |
| WO | 99/54310 | 10/1999 |
| WO | 99/54320 | 10/1999 |
| WO | 99/61423 | 12/1999 |
| WO | 03/080182 | 10/2003 |
| WO | 2005/002503 | 1/2005 |
| WO | 2005/099353 | 10/2005 |
| WO | 2006/008754 | 1/2006 |
| WO | 2007/016589 | 2/2007 |
| WO | 2008/080969 | 7/2008 |
| WO | 2008/106130 | 9/2008 |

OTHER PUBLICATIONS

CalpainInhibitors, 2012, http://www.ncbi.nlm.nih.gov/pubmed/21434837.*

Edelstein, C.L., et al., Proc. Natl. Acad. Sci, USA, 1995, 92, pp. 7662-7666.
Yoshida, K.I., et al., Jap. Circ. J. 1995, 59(1), pp. 40-48.
Li, X., et al., Mol. Biochem. Parasitol. 2007, 155(1), pp. 26-32.
Peltier, J., et al., J A, Soc Nephrol. 2006, 17, pp. 3415-3423.
Groshong, J.S., et al., J. Clin. Invest. 2007, 117(10), pp. 2903-2912.
Takano, et al., J Biol Chem. 2005, 280(16), pp. 16175-16184.
Spencer, M.J., et al., Hum Mol Gen, 2002, 11(21), pp. 2645-2655.
Patrick, G., et al., Nature 1999, 402, pp. 615-622.
Monaco, E.A., et al., Curr. Alzheimer Res. 2004, 1(1), pp. 33-38.
Higuchi, J., et al., J. Biol. Chem. 2005, 280(15), pp. 15229-15237.
Mokhtarian, F., et al., J. Neuroimmunology 2006, vol. 180, pp. 135-146.
Park, et al. J. Meurosci. 2005, 25, pp. 5365-5375.
Higaki, J., et al., Neuron, 1995, 14, pp. 651-659.
Watanabe, N., et al., Cytokine 1994, 6(6), pp. 597-601.
Shiba, E., et al. 20th Meeting Int. Association Breast Cancer Res., Sendai Jp, Sep. 25-28, 1994, Int. J. Oncol. S (Suppl.), 1994, p. 381.
O'Donnell, et al., J. Neurosci. 2006, 26(3), pp. 981-990.
Teranishi, et al., Biochem. Biophys. Res. Comm. 2003, 303(3), pp. 940-946.
Kunz, et al., Pain 2004, 110, pp. 409-418.
Wang, et al., Brain 2004, 127, pp. 671-679.
Cuzzocrea, et al., American Journal of Pathology 2000, 157(6), pp. 2065-2079.
Shi, Y., et al., Am. J. Physiol. Renal Physiol. 2000, 279, pp. 509-517.
Dnyanmote, et al., Toxicology and Applied Pharmacology 2006, 215, pp. 146-157.
Chatterjee, P. et al., Biochem. Pharmacol. 2005, 7, pp. 1121-1131.
Pietsch, M., et al., current Topics in Medicinal Chemistry, 2010, 10, pp. 270-293.
Carragher, N.O., Curr. Pharm. Design 2006, 12, pp. 615-638.
Wang, K.K., et al. Drugs of the Future, 1998, 23(7), pp. 741-749; and Trends in Pharmacol. Sc. 1994, 15, pp. 412-419.
Fehrentz, J.A., et al., Synthesis 1983, pp. 676-678.
Saez, M.E., et al. "Drug Discovery Today", 2006, 11(19/20), pp. 917-923.
Suzuki, K., et al., Biol. Chem. Hoppe-Seyler, 1995, 376(9), pp. 523-529.
Barrett, M.J., et al. Life Sci. 1991, 48, pp. 1659-1669.
Wang, K., et al., Trends in Pharmacol. Sci. 1994, 15, pp. 412-419.
Medana, et al., Neuropath and Appl. Neurobiol. 2007, 33, pp. 179-192.
Hong, Seung-Chyul, et al., Stroke, 1994, 25(3), pp. 663-669.
Bartus, R.T., et al., Neurological Res. 1995, 17, pp. 249-258.
Saatman, K.E., et al., Proc. Natl. Acad. Sci. USA, 1996, 93, pp. 3428-3433.

* cited by examiner

CARBOXAMIDE COMPOUNDS AND THEIR USE AS CALPAIN INHIBITORS

CROSS-REFERENCE TO RELATED APPLICATIONS

This claims the benefit of U.S. Provisional Patent Application Nos. 61/154,118, filed Feb. 20, 2009 and 61/289,772, filed Dec. 23, 2009, the contents of all of which are incorporated herein by reference.

FIELD OF THE INVENTION

The present invention relates to novel carboxamide compounds and their use for the manufacture of a medicament. The carboxamide compounds are inhibitors of calpain (calcium dependant cysteine proteases). The invention therefore also relates to the use of these carboxamide compounds for treating a disorder associated with an elevated calpain activity.

BACKGROUND OF THE INVENTION

Calpains are intracellular, proteolytic enzymes from the cysteine protease group and are found in many cells. The enzyme calpain is activated by elevated calcium concentration, with a distinction being made between calpain I or μ-calpain, which is activated by μ-molar concentrations of calcium ions, and calpain II or m-calpain, which is activated by m-molar concentrations of calcium ions. Currently, further calpain isoenzymes are also postulated (M. E. Saez et al.; Drug Discovery Today 2006, 11 (19/20), pp. 917-923; K. Suzuki et al., Biol. Chem. Hoppe-Seyler, 1995, 376 (9), pp. 523-9).

Calpains play an important role in various physiological processes. These processes include the cleavage of different regulatory proteins such as protein kinase C, cytoskeletal proteins such as MAP 2 and spectrin, and muscle proteins, protein degradation in rheumatoid arthritis, proteins in the activation of platelets, neuropeptide metabolism, proteins in mitosis, and others which are listed in: M. J. Barrett et al., Life Sci. 1991, 48, pp. 1659-69; K. Wang et al., Trends in Pharmacol. Sci. 1994, 15, pp. 412-419.

Elevated calpain levels have been measured in various pathophysiological processes, for example: ischemias of the heart (e.g. myocardial infarction), the kidney, the lung, the liver or the central nervous system (e.g. stroke), inflammations, muscular dystrophies, cataracts of the eyes, diabetes, HIV disorders, injuries to the central nervous system (e.g. brain trauma), Alzheimer's, Huntington's, Parkinson's diseases, multiple sclerosis etc. (see K. K. Wang, above) and infectious diseases such as malaria (I M Medana et al., Neuropath and Appl. Neurobiol. 2007, 33, pp. 179-192). It is assumed that there is a connection between these diseases and generally or persistently elevated intracellular calcium levels. This results in calcium-dependent processes becoming hyperactivated and no longer being subject to normal physiological control. A corresponding hyperactivation of calpains can also trigger pathophysiological processes.

For this reason, it was postulated that inhibitors of calpain could be of use for treating these diseases. This postulate was confirmed by a variety of investigations. Thus, Seung-Chyul Hong et al., Stroke 1994, 25 (3), pp. 663-669, and R. T. Bartus et al., Neurological Res. 1995, 17, pp. 249-258, have demonstrated that calpain inhibitors have a neuroprotective effect in acute neurodegenerative impairments or ischemias such as occur after cerebral stroke. K. E. Saatman et al., Proc. Natl. Acad. Sci. USA, 1996, 93, pp. 3428-3433 describe that following experimental brain trauma, calpain inhibitors also improved recovery from the memory performance deficits and neuromotor impairments. C. L. Edelstein et al., Proc. Natl. Acad. Sci. USA, 1995, 92, pp. 7662-6, found that calpain inhibitors have a protective effect on hypoxia-damaged kidneys. Yoshida, Ken Ischi et al., Jap. Circ. J. 1995, 59 (1), pp. 40-48, pointed out that calpain inhibitors had favorable effects following cardiac damage which was produced by ischemia or reperfusion. The calpain inhibitor BDA-410 delayed the progression of malaria infection in a mouse model of malaria pathogenesis as shown by X. Li et al., Mol. Biochem. Parasitol. 2007, 155 (1), pp 26-32.

More recent studies have shown in calpastatin transgenic animals that the expression of the natural inhibitor of calpain significantly attenuates the pathophysiological effects of activated calpain in experimental glomerulonephritis shown by J. Peltier et al., J. Am. Soc. Nephrol. 2006, 17, pp. 3415-3423, in cardiovascular remodeling in angiotensin II-induced hypertension, in impaired synaptic transmission in slow-channel congenital myasthenic syndrome shown by J. S. Groshong et al., J. Clin. Invest. 2007, 117 (10), pp 2903-2912, in excitotoxic DNA fragmentation via mitochondrial pathways shown by J. Takano et al., J. Biol. Chem. 2005, 280 (16), pp. 16175-16184, and in necrotic processes in dystrophic muscles shown by M. J. Spencer et al., Hum. Mol. Gen., 2002, 11(21), pp. 2645-2655.

It has been shown in recent years that both the function and the metabolism of a number of important proteins involved in the development of Alzheimer's disease are modulated by calpain. Various external influences such as, for example, excitotoxins, oxidative stress or else the action of amyloid protein lead to hyperactivation of calpain in the nerve cell, causing, as cascade, a dysregulation of the CNS-specific kinase cdk5 and subsequently a hyperphosphorylation of the so-called tau protein. Whereas the actual task of the tau protein consists of stabilizing the microtubules and thus the cytoskeleton, phosphorylated tau is no longer able to fulfil this function; the cytoskeleton collapses, axonal transport of matter is impaired and thus eventually the nerve cell degenerates (G. Patrick et al., Nature 1999, 402, pp. 615-622; E. A. Monaco et al.; Curr. Alzheimer Res. 2004, 1 (1), pp. 33-38). Accumulation of phosphorylated tau additionally leads to the formation of so-called neurofibrillary tangles (NFTs) which, together with the well-known amyloid plaques, represent a pathological hallmark of Alzheimer's disease. Similar changes in the tau protein, generally referred to important feature of as tauopathies are also observed in other (neuro) degenerative disorders such as, for example, following stroke, inflammations of the brain, Parkinsonism, in normal-pressure hydrocephalus and Creutzfeldt-Jakob disease.

The involvement of calpain in neurodegenerative processes has been demonstrated in transgenic mice with the aid of calpastatin, a specific and natural inhibitor of calpains (Higuchi et al.; J. Biol. Chem. 2005, 280 (15), pp. 15229-15237). It was possible with the aid of a calpain inhibitor to reduce markedly the clinical signs of acute autoimmune encephalomyelitis in a mouse model of multiple sclerosis (F. Mokhtarian et al.; J. Neuroimmunology 2006, Vol. 180, pp. 135-146). It has further been shown that calpain inhibitors on the one hand block the Ab-induced degeneration of neurons (Park et al.; J. Neurosci. 2005, 25, pp. 5365-5375), and in addition reduce the release of the β-amyloid precursor protein (β APP) (J. Higaki et al., Neuron, 1995, 14, pp. 651-659). With this background, calpain inhibitors having sufficient CNS availability represent a novel therapeutic principle for the treatment of neurodegenerative disorders in general and in particular also of Alzheimer's disease.

The release of interleukin-1α is likewise inhibited by calpain inhibitors (N. Watanabe et al., Cytokine 1994, 6(6), pp. 597-601). It has additionally been found that calpain inhibitors show cytotoxic effects on tumor cells (E. Shiba et al. 20th Meeting Int. Ass. Breast Cancer Res., Sendai Jp, 1994, 25.-28. Sep., Int. J. Oncol. S(Suppl.), 1994, 381).

The involvement of calpain in HIV disorders has only recently been shown. Thus, it has been demonstrated that the HIV-induced neurotoxicity is mediated by calpain (O'Donnell et al.; J. Neurosci. 2006, 26 (3), pp. 981-990). Calpain involvement in the replication of the HIV virus has also been shown (Teranishi et al.; Biochem. Biophys. Res. Comm. 2003, 303 (3), pp. 940-946).

Recent investigations indicate that calpain plays a part in so-called nociception, the perception of pain. Calpain inhibitors showed a distinctly beneficial effect in various preclinically relevant models of pain, e.g. in the thermally induced hyperalgesia in rats (Kunz et al.; Pain 2004, 110, pp. 409-418), in Taxol-induced neuropathy (Wang et al.; Brain 2004, 127, pp. 671-679) and in acute and chronic inflammatory processes (Cuzzocrea et al.; American Journal of Pathololgy 2000, 157 (6), pp. 2065-2079).

The involvement of calpain in the development of kidney diseases, such as chronic kidney diseases, e.g. diabetic nephropathy, has also been shown recently. Thus, it has been demonstrated by Y. Shi et al. in animal models that the natural calpain inhibitor calpastatin is down regulated during renal ischemia reperfusion (Am. J. Physiol. Renal Physiol. 2000, 279, pp. 509-517). Furthermore, A. Dnyanmote et al., Toxicology and Applied Pharmacology 2006, 215, pp. 146-157, have shown that inhibition of calpain via overexpression of calpastatin reduces the progression of DCVC-induced renal injury in a model of acute renal failure. In addition, Peltier et al. have demonstrated that calpain activation and secretion promotes glomerular injury in experimental glomerulonephritis (J. Am. Soc. Nephrol. 2006, 17, pp. 3415-3423). It has also been shown that calpain inhibitors reduce renal dysfunction and injury caused by renal ischemia-reperfusion and thus may be useful in enhancing the tolerance of the kidney against renal injury associated with aortovascular surgery or renal transplantation (P. Chatterjee et al., Biochem. Pharmacol. 2005, 7, pp. 1121-1131).

Further possible applications of calpain inhibitors are detailed in: M. E. Saez et al.; Drug Discovery Today 2006, 11 (19/20), pp. 917-923; N, O. Carragher, Curr. Pharm. Design 2006, 12, pp. 615-638; K. K. Wang et al.; Drugs of the Future 1998, 23 (7), pp. 741-749; and Trends in Pharmacol. Sci. 1994, 15, pp. 412-419.

With the calpain inhibitors described to date a general distinction is made between irreversible and reversible inhibitors, and peptide and non-peptide inhibitors.

Irreversible inhibitors are usually alkylating substances. They have the disadvantage that they firstly react unselectively and/or are unstable in the body. Thus, corresponding inhibitors often show unwanted side effects such as toxicity, and application thereof is therefore markedly restricted. The irreversible inhibitors include for example epoxides such as E64, α-halo ketones, and disulfides.

A large number of known reversible calpain inhibitors are peptide aldehydes which are derived in particular from di- or tripeptides such as, for example, Z-Val-Phe-H (MDL 28170). Derivatives and prodrugs structurally derived from aldehydes are also described, especially corresponding acetals and hemiacetals (e.g. hydroxytetrahydro-furans, hydroxyoxazolindines, hydroxymorpholines and the like), but also imines or hydrazones. However, under physiological conditions, peptide aldehydes and related compounds usually have the disadvantage that, owing to their reactivity, they are frequently unstable, are rapidly metabolized and are prone to unspecific reactions which may likewise cause toxic effects (J. A. Fehrentz and B. Castro, Synthesis 1983, pp. 676-78).

In recent years, a number of non-peptide carboxamides having a β-keto function in the amine moiety and inhibiting calpain have been described. Thus, WO-98/16512 describes 3-amino-2-oxo carboxylic acid derivatives whose amino group is amidated with a 4-piperidinecarboxylic acid compound. WO-99/17775 describes similar compounds which are amidated with a quinolinecarboxylic acid. WO-98/25883, WO-98/25899 and WO-99/54294 describe 3-amino-2-oxo carboxylic acid derivatives whose amino group is amidated with a substituted benzoic acid. WO-99/61423 describes 3-amino-2-oxo carboxylic acid derivatives whose amino group is amidated with an aromatic carboxylic acid carrying a tetrahydroquinoline/isoquinoline and 2,3-dihydroindole/isoindole residue. Similar compounds in which the aromatic carboxylic acid residue carries a heterocyloalkyl radical or (hetero)aryl radical which is optionally connected via a linker are described in WO-99/54320, WO-99/54310, WO-99/54304 and WO-99/54305. Likewise, WO 08/080,969 describes nicotinamides of 3-amino-2-oxo carboxylic acid derivatives that in position 2 of the pyridine ring are linked to a substituted pyrazole via a nitrogen atom. WO-99/54293 describes benzamides of 4-amino-3-oxo carboxylic acid derivatives. WO-03/080182 describes the use of the aforementioned amides for the treatment of pulmonary diseases. The nonpeptide calpain inhibitors mentioned therein also have a number of disadvantages, in particular a low or absent selectivity in respect of related cysteine proteases, such as various cathepsins, likewise possibly leading to unwanted side effects.

SUMMARY OF THE INVENTION

The present invention is thus based on the object of providing compounds which inhibit, in particular selectively, calpain even at low serum concentrations. The compounds were intended in particular to display a high selectivity in relation to the inhibition of calpain, i.e. inhibit other cystein proteases, e.g. cathepsin, not at all or only at significantly higher concentrations. Furthermore, the compounds should have a sufficient cytosolic stability, in particular in human cells, such as human hepatocytes, and in consequence improved pharmacokinetics.

This object and further objects are achieved by the carboxamide compounds of the general formula I described below, the tautomers thereof and the pharmaceutically suitable salts thereof:

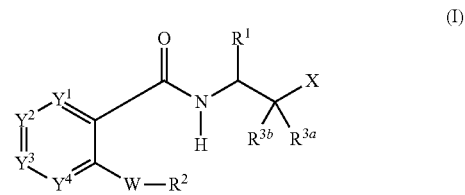

in which
$R^1$ is hydrogen, $C_1$-$C_{10}$-alkyl, $C_2$-$C_{10}$-alkenyl, $C_2$-$C_{10}$-alkynyl, where the last 3 radicals mentioned may be partly or completely halogenated and/or have 1, 2 or 3 substituents $R^{1a}$, $C_3$-$C_7$-cycloalkyl, $C_3$-$C_7$-cycloalkyl-$C_1$-$C_4$-alkyl, where a $CH_2$ group in the cycloalkyl moiety of the last two radicals mentioned may be replaced by O, NH, or S, or two adjacent C atoms may form a double bond, where the cycloalkyl moiety may further have 1, 2, 3 or 4 radicals $R^{1b}$, aryl, hetaryl, aryl-$C_1$-$C_6$-alkyl, aryl-$C_2$-$C_6$-alkenyl, hetaryl-$C_1$-$C_4$-alkyl or hetaryl-$C_2$-$C_6$-alkenyl, where aryl and hetaryl in the last 6 radicals mentioned may be unsubstituted or carry 1, 2, 3 or 4 identical or different radicals $R^{1c}$; where $R^{1a}$ is selected independently of one another from OH, SH, COON, CN, $OCH_2COOH$, $C_1$-$C_6$-alkoxy, $C_1$-$C_6$-haloalkoxy, $C_3$-$C_7$-cycloalkyloxy, $C_1$-$C_6$-alkylthio, $C_1$-$C_6$-haloalkylthio, $COOR^{a1}$, $CONR^{a2}R^{a3}$, $SO_2NR^{a2}R^{a3}$, $-NR^{a2}-SO_2-R^{a4}$, $NR^{a2}-CO-R^{a5}$, $SO_2-R^{a4}$ and $NR^{a6}R^{a7}$, $R^{1b}$ is selected independently of one another from OH, SH, COON, CN, $OCH_2COOH$, halogen, phenyl which optionally has 1, 2 or 3 substituents $R^{1d}$, or $C_1$-$C_6$-alkyl, $C_1$-$C_6$-alkoxy, $C_1$-$C_6$-alkylthio, where the alkyl moieties in the last 3 substituents mentioned may be partly or completely halogenated and/or have 1, 2 or 3 substituents $R^{1a}$, $COOR^{b1}$, $CONR^{b2}R^{b3}$, $SO_2NR^{b2}R^{b3}$, $NR^{b2}-SO_2-R^{b4}$, $NR^{b2}-CO-R^{b5}$, $SO_2-R^{b4}$, and $NR^{b6}R^{b7}$, in addition two $R^{1b}$ radicals may together form a $C_1$-$C_4$-alkylene group, or 2 $R^{1b}$ radicals bonded to adjacent C atoms of cycloalkyl may form together with the carbon atoms to which they are bonded also a benzene ring, $R^{1c}$ is selected independently of one another from OH, SH, halogen, $NO_2$, $NH_2$, CN, COON, $OCH_2COOH$, $C_1$-$C_6$-alkyl, $C_1$-$C_6$-alkoxy, $C_1$-$C_6$-alkoxy-$C_1$-$C_4$-alkyl, $C_1$-$C_6$-alkylthio, where the alkyl moieties in the last 4 substituents mentioned may be partly or completely halogenated and/or have 1, 2 or 3 substituents $R^{1a}$, $C_3$-$C_7$-cycloalkyl, $C_3$-$C_7$-cycloalkyl-$C_1$-$C_4$-alkyl, $C_3$-$C_7$-cycloalkyloxy, where the cycloalkyl moiety of the last three radicals mentioned may have 1, 2, 3 or 4 $R^{1b}$ radicals, and where 1 or 2 $CH_2$-groups in the cycloalkyl moiety may be replaced by O, NH or S, aryl, hetaryl, O-aryl, O—$CH_2$-aryl, where the last three radicals mentioned are unsubstituted in the aryl moiety or may carry 1, 2, 3 or 4 radicals $R^{1d}$, $COOR^{c1}$, $CONR^{c2}R^{c3}$, $SO_2NR^{c2}R^{c3}$, $NR^{c2}-SO_2-R^{c4}$, $NR^{c2}-CO-R^{c5}$, $SO_2-R^{c4}$, —$(CH_2)_p$—$NR^{c6}R^{c7}$ with p=0, 1, 2, 3, 4, 5 or 6 and O—$(CH_2)_q$—$NR^{c6}R^{c7}$ with q=2, 3, 4, 5 or 6; where $R^{a1}$, $R^{b1}$ and $R^{c1}$ are independently of one another H, $C_1$-$C_6$-alkyl, $C_1$-$C_6$-haloalkyl, $C_1$-$C_6$-alkyl which has 1, 2 or 3 substituents $R^{1a}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, aryl-$C_1$-$C_4$-alkyl, hetaryl or hetaryl-$C_1$-$C_4$-alkyl, where aryl and hetaryl in the last 4 radicals mentioned are unsubstituted or have 1, 2 or 3 substituents $R^{1d}$, $R^{a2}$, $R^{b2}$ and $R^{c2}$ are independently of one another H, $C_1$-$C_6$-alkyl, $C_1$-$C_6$-haloalkyl, $C_1$-$C_6$-alkyl which has 1, 2 or 3 substituents $R^{1a}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, aryl-$C_1$-$C_4$-alkyl, hetaryl or hetaryl-$C_1$-$C_4$-alkyl, where aryl and hetaryl in the last 4 radicals mentioned are unsubstituted or have 1, 2 or 3 substituents $R^{1d}$, and $R^{a3}$, $R^{b3}$ and $R^{c3}$ are independently of one another H, $C_1$-$C_6$-alkyl, $C_1$-$C_6$-haloalkyl, $C_1$-$C_6$-alkyl which has 1, 2 or 3 substituents $R^{1a}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, aryl-$C_1$-$C_4$-alkyl, hetaryl or hetaryl-$C_1$-$C_4$-alkyl, where aryl and hetaryl in the last 4 radicals mentioned are unsubstituted or have 1, 2 or 3 substituents $R^{1d}$, or the two radicals $R^{a2}$ and $R^{a3}$, or $R^{b2}$ and $R^{b3}$ or $R^{c2}$ and $R^{c3}$ form together with the N atom a 3 to 7-membered, optionally substituted nitrogen heterocycle which may optionally have 1, 2 or 3 further different or identical heteroatoms from the group of O, N, S as ring members, $R^{a4}$, $R^{b4}$ and $R^{c4}$ are independently of one another $C_1$-$C_6$-alkyl, $C_1$-$C_6$-haloalkyl, $C_1$-$C_6$-alkyl which has 1, 2 or 3 substituents $R^{1a}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, aryl-$C_1$-$C_4$-alkyl, hetaryl or hetaryl-$C_1$-$C_4$-alkyl, where aryl and hetaryl in the last 4 radicals mentioned are unsubstituted or have 1, 2 or 3 substituents $R^{1d}$, and $R^{a5}$, $R^{b5}$ and $R^{c5}$ have independently of one another one of the meanings mentioned for $R^{a1}$, $R^{b1}$ and $R^{c1}$;

$R^{a6}$, $R^{b6}$ and $R^{c6}$ are independently of one another H, $C_1$-$C_6$-alkyl, $C_1$-$C_6$-alkoxy, $C_1$-$C_6$-haloalkyl, $C_1$-$C_6$-alkyl which has 1, 2 or 3 substituents $R^{1a}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, CO—$C_1$-$C_6$-alkyl, CO—O—$C_1$-$C_6$-alkyl, $SO_2$—$C_1$-$C_6$-alkyl, aryl, hetaryl, O-aryl, $OCH_2$-aryl, aryl-$C_1$-$C_4$-alkyl, hetaryl-$C_1$-$C_4$-alkyl, CO-aryl, CO-hetaryl, CO-(aryl-$C_1$-$C_4$-alkyl), CO-(hetaryl-$C_1$-$C_4$-alkyl), CO—O-aryl, CO—O-hetaryl, CO—O-(aryl-$C_1$-$C_4$-alkyl), CO—O-(hetaryl-$C_1$-$C_4$-alkyl), $SO_2$-aryl, $SO_2$-hetaryl, $SO_2$-(aryl-$C_1$-$C_4$-alkyl) or $SO_2$—(hetaryl-$C_1$-$C_4$-alkyl), where aryl and hetaryl in the last 18 radicals mentioned are unsubstituted or have 1, 2 or 3 substituents $R^{1d}$, and $R^{a7}$, $R^{b7}$ and $R^{c7}$ are independently of one another H, $C_1$-$C_6$-alkyl, $C_1$-$C_6$-haloalkyl, $C_1$-$C_6$-alkyl which has 1, 2 or 3 substituents $R^{1a}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, aryl-$C_1$-$C_4$-alkyl, hetaryl or hetaryl-$C_1$-$C_4$-alkyl, where aryl and hetaryl in the last 4 radicals mentioned are unsubstituted or have 1, 2 or 3 substituents $R^{1d}$, or the two radicals $R^{a6}$ and $R^{a7}$, or $R^{b6}$ and $R^{b7}$ or $R^{c6}$ and $R^{c7}$ form together with the N atom a 3 to 7-membered, optionally substituted nitrogen heterocycle which may optionally have 1, 2 or 3 further different or identical heteroatoms from the group of O, N and S as ring members, or two radicals $R^{1b}$ or $R^{1c}$ bonded to adjacent C atoms form together with the C atoms to which they are bonded a 4-, 5-, 6- or 7-membered, optionally substituted carbocycle or an optionally substituted heterocycle which has 1, 2 or 3 different or identical heteroatoms from the group of O, N and S as ring members;

$R^{1d}$ is selected from halogen, OH, SH, $NO_2$, COON, C(O)$NH_2$, CHO, CN, $NH_2$, $OCH_2COOH$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, CO—$C_1$-$C_6$-alkyl, CO—O—$C_1$-$C_6$-alkyl, NH—$C_1$-$C_6$-alkyl, NHCHO, NH—C(O)$C_1$-$C_6$-alkyl, and $SO_2$—$C_1$-$C_6$-alkyl;

$R^2$ is $C_3$-$C_7$-cycloalkyl, $C_3$-$C_7$-cycloalkyl-$C_1$-$C_4$-alkyl, where a $CH_2$ group in the cycloalkyl moiety of the last two radicals mentioned may be replaced by O, NH, or S, or two adjacent C atoms may form a double bond, where the cycloalkyl moiety may additionally have 1, 2, 3 or 4 $R^{2a}$ radicals;

aryl, O-aryl, O—$CH_2$-aryl, hetaryl, aryl-$C_1$-$C_6$-alkyl, aryl-$C_2$-$C_6$-alkenyl, hetaryl-$C_1$-$C_4$-alkyl or hetaryl-$C_2$-$C_6$-alkenyl, where aryl and hetaryl in the last 8 radicals mentioned may be unsubstituted or carry 1, 2, 3 or 4 identical or different $R^{2b}$ radicals; where $R^{2a}$ has one of the meanings indicated for $R^{1b}$, and
$R^{2b}$ has one of the meanings indicated for $R^{1c}$;

$R^{3a}$ and $R^{3b}$ are independently of one another hydroxy or $C_1$-$C_4$-alkoxy, or together with the carbon atom to which they are bonded are C=O; or $R^{3a}$ and $R^{3b}$ together form a moiety S-Alk-S, O-Alk-S or O-Alk-O, wherein Alk is linear $C_2$-$C_5$-alkandiyl, which may be unsubstituted or substituted with 1, 2, 3 or 4 radicals selected from $C_1$-$C_4$-alkyl or halogen;

X is hydrogen or a radical of the formulae C(=O)—O—$R^{x1}$, C(=O)—$NR^{x2}R^{x3}$, C(=O)—N($R^{x4}$)—($C_1$-$C_6$-alkylene)-$NR^{x2}R^{x3}$ or C(=O)—N($R^{x4}$)$NR^{x2}R^{x3}$, in which $R^{x1}$ is hydrogen, $C_1$-$C_6$-alkyl, $C_1$-$C_6$-haloalkyl, $C_1$-$C_6$-alkyl which has 1, 2 or 3 substituents $R^{xa}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, where alkyl, alkenyl, alkoxy, alkynyl, cycloalkyl, heterocycloalkyl in the last 6 radicals mentioned are unsubstituted or have 1, 2 or 3 substituents $R^{xa}$, or aryl, aryl-$C_1$-$C_4$-alkyl, hetaryl or hetaryl-$C_1$-$C_4$-alkyl, where aryl and hetaryl in the last 4 radicals mentioned are unsubstituted or have 1, 2 or 3 substituents $R^{xd}$, $R^{x2}$ is H, OH, CN, $C_1$-$C_6$-alkyl, $C_1$-$C_6$-haloalkyl, $C_1$-$C_6$-alkyl which has 1, 2 or 3 substituents $R^{xa}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, CO—$C_1$-$C_6$-alkyl, CO—O—$C_1$-$C_6$-alkyl, $SO_2$—$C_1$-$C_6$-alkyl, O—$C_1$-$C_6$-alkyl, where alkyl, alkoxy, alkenyl, alkynyl, cycloalkyl, heterocycloalkyl in the last 10 radicals mentioned are unsubstituted or have 1, 2 or 3 substituents $R^{xa}$, aryl, O-aryl, O—$CH_2$-aryl, hetaryl, O—$CH_2$-hetaryl, aryl-$C_1$-$C_4$-alkyl, hetaryl-$C_1$-$C_4$-alkyl, CO-aryl, CO-hetaryl, CO-(aryl-$C_1$-$C_4$-alkyl), CO-(hetaryl-$C_1$-$C_4$-alkyl), CO—O-aryl, CO—O-hetaryl, CO—O-(aryl-$C_1$-$C_4$-alkyl), CO—O-(hetaryl-$C_1$-$C_4$-alkyl), $SO_2$-aryl, $SO_2$-hetaryl, $SO_2$-(aryl-$C_1$-$C_4$-alkyl) or $SO_2$-(hetaryl-$C_1$-$C_4$-alkyl), where aryl and hetaryl in the last 19 radicals mentioned are unsubstituted or have 1, 2 or 3 substituents $R^{xd}$, $R^{x3}$ is H, $C_1$-$C_6$-alkyl, $C_1$-$C_6$-haloalkyl, $C_1$-$C_6$-alkyl which has 1, 2 or 3 substituents $R^{xa}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, where alkyl, alkenyl, alkoxy, alkynyl, cycloalkyl, heterocycloalkyl in the last 6 radicals mentioned are unsubstituted or have 1, 2 or 3 substituents $R^{xa}$, aryl, aryl-$C_1$-$C_4$-alkyl, hetaryl or hetaryl-$C_1$-$C_4$-alkyl, where aryl and hetaryl in the last 4 radicals mentioned are unsubstituted or have 1, 2 or 3 substituents $R^{xd}$, or the two radicals $R^{x2}$ and $R^{x3}$ form together with the N atom a 3- to 7-membered nitrogen heterocycle which may optionally have 1, 2 or 3 further different or identical heteroatoms from the group of O, N, S as ring members, and which may have 1, 2 or 3 substituents $R^{xb}$, and $R^{x4}$ is H, OH, CN, $C_1$-$C_6$-alkyl, $C_1$-$C_6$-haloalkyl, $C_1$-$C_6$-alkyl which has 1, 2 or 3 substituents $R^{xa}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, CO—$C_1$-$C_6$-alkyl, CO—O—$C_1$-$C_6$-alkyl, $SO_2$—$C_1$-$C_6$-alkyl, where alkyl, alkenyl, alkoxy, alkynyl, cycloalkyl, heterocycloalkyl in the last 9 radicals mentioned are unsubstituted or have 1, 2 or 3 substituents $R^{xa}$, aryl, O-aryl, O—$CH_2$-aryl, hetaryl, aryl-$C_1$-$C_4$-alkyl, hetaryl-$C_1$-$C_4$-alkyl, CO-aryl, CO-hetaryl, CO-(aryl-$C_1$-$C_4$-alkyl), CO-(hetaryl-$C_1$-$C_4$-alkyl), CO—O-aryl, CO—O-hetaryl, CO—O-(aryl-$C_1$-$C_4$-alkyl), CO—O-(hetaryl-$C_1$-$C_4$-alkyl), $SO_2$-aryl, $SO_2$-hetaryl, $SO_2$-(aryl-$C_1$-$C_4$-alkyl) or $SO_2$-(hetaryl-$C_1$-$C_4$-alkyl), where aryl and hetaryl in the last 18 radicals mentioned are unsubstituted or have 1, 2 or 3 substituents $R^{xd}$, and where $R^{xa}$ has one of the meanings indicated for $R^{1a}$, $R^{xb}$ has one of the meanings indicated for $R^{1b}$, and $R^{xd}$ has one of the meanings indicated for $R^{1d}$;

$Y^1$, $Y^2$, $Y^3$ or $Y^4$ are $CR^y$, or one or two of the variables $Y^1$, $Y^2$, $Y^3$ or $Y^4$ are a nitrogen atom, and the remaining variables $Y^1$, $Y^2$, $Y^3$ or $Y^4$ are $CR^y$;

$R^y$ is selected independently of one another from hydrogen, OH, SH, halogen, $NO_2$, $NH_2$, CN, $CF_3$, $CHF_2$, $CH_2F$, O—$CF_3$, O—$CHF_2$, O—$CH_2F$, COON, $OCH_2COOH$, $C_1$-$C_6$-alkyl, $C_1$-$C_6$-alkoxy, $C_1$-$C_6$-alkoxy-$C_1$-$C_4$-alkyl, $C_1$-$C_6$-alkylthio, where the last 4 radicals mentioned may be partly or completely halogenated and/or have 1, 2 or 3 substituents $R^{ya}$, $C_3$-$C_7$-cycloalkyl, $C_3$-$C_7$-cycloalkyl-$C_1$-$C_4$-alkyl, $C_3$-$C_7$-cycloalkyl-O, where the cycloalkyl moiety in the last three radicals mentioned may have 1, 2, 3 or 4 $R^{yb}$ radicals, and where 1 or 2 $CH_2$-groups in the cycloalkyl moiety may be replaced by O, NH or S, aryl, hetaryl, O-aryl, $CH_2$-aryl, O—$CH_2$-aryl, where the last 4 radicals mentioned are unsubstituted in the aryl moiety or may carry 1, 2, 3 or 4 radicals $R^{yd}$, $COOR^{y1}$, $CONR^{y2}R^{y3}$, $SO_2NR^{y2}R^{y3}$, —NH—$SO_2$—$R^{y4}$, NH—CO—$R^{y5}$, $SO_2$—$R^{y4}$, —($CH_2$)$_p$—$NR^{y6}R^{y7}$ with p=0, 1, 2, 3, 4, 5 or 6 and O—($CH_2$)$_q$—$NR^{y6}R^{y7}$ with q=2, 3, 4, 5 or 6;

or two $R^y$ radicals bonded to adjacent C atoms form together with the C atoms to which they are bonded a 4-, 5-, 6- or 7-membered, optionally substituted carbocycle or an optionally substituted heterocycle which has 1, 2 or 3 different or identical heteroatoms from the group of O, N, S as ring members, where $R^{ya}$ has one of the meanings indicated for $R^{1a}$,
$R^{yb}$ has one of the meanings indicated for $R^{1b}$,
$R^{yd}$ has one of the meanings indicated for $R^{1d}$,
$R^{y1}$ has one of the meanings indicated for $R^{c1}$,
$R^{y2}$ has one of the meanings indicated for $R^{c2}$,
$R^{y3}$ has one of the meanings indicated for $R^{c3}$,
$R^{y4}$ has one of the meanings indicated for $R^{c4}$,
$R^{y5}$ has one of the meanings indicated for $R^{c5}$,
$R^{y6}$ has one of the meanings indicated for $R^{c6}$, and
$R^{y7}$ has one of the meanings indicated for $R^{c7}$;

W is a radical of the formulae W1 or W2:

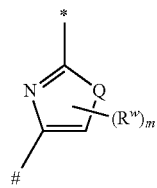

(W1)

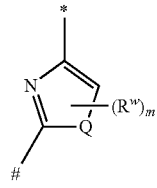

(W2)

in which
* means the linkage to the 6-membered aromatic ring, and
# means the linkage to $R^2$,
m is 0 or 1,
Q is O, S or $NR^{ww}$,
$R^w$ is selected from OH, SH, halogen, $NO_2$, $NH_2$, CN, COON, $OCH_2COOH$, $C_1$-$C_6$-alkyl, $C_1$-$C_6$-alkoxy, $C_1$-$C_6$-alkoxy-$C_1$-$C_4$-alkyl, $C_1$-$C_6$-alkylthio, where the last 4 radicals mentioned may be partly or completely halogenated and/or have 1, 2 or 3 substituents $R^{wa}$,
$C_3$-$C_7$-cycloalkyl, $C_3$-$C_7$-cycloalkyl-$C_1$-$C_4$-alkyl, $C_3$-$C_7$-cycloalkyloxy, where the cycloalkyl moiety of the last three radicals mentioned may have 1, 2, 3 or 4 radicals $R^{wb}$,
aryl, O-aryl, O—$CH_2$-aryl, hetaryl, where the last four radicals mentioned are unsubstituted in the aryl moiety or may carry 1, 2, 3 or 4 radicals $R^{wd}$,
$COOR^{w1}$, $CONR^{w2}R^{w3}$, $SO_2NR^{w2}R^{w3}$, $NR^{w2}$—$SO_2$—$R^{w4}$,
$NR^{w2}$—CO—$R^{w5}$, $SO_2$—$R^{w4}$,
—$(CH_2)_p$—$NR^{w6}R^{w7}$ with p=0, 1, 2, 3, 4, 5 or 6 and O—$(CH_2)_q$—$NR^{w6}R^{w7}$ with q=2, 3, 4, 5 or 6;
or two $R^w$ radicals bonded to adjacent C atoms form together with the C atoms to which they are bonded a 4-, 5-, 6- or 7-membered, optionally substituted carbocycle or an optionally substituted heterocycle which has 1, 2 or 3 different or identical heteroatoms from the group of O, N, S as ring members, where
$R^{wa}$ has one of the meanings indicated for $R^{1a}$,
$R^{wb}$ has one of the meanings indicated for $R^{1b}$,
$R^{wd}$ has one of the meanings indicated for $R^{1d}$,
$R^{w1}$ has one of the meanings indicated for $R^{c1}$,
$R^{w2}$ has one of the meanings indicated for $R^{c2}$,
$R^{w3}$ has one of the meanings indicated for $R^{c3}$,
$R^{w4}$ has one of the meanings indicated for $R^{c4}$,
$R^{w5}$ has one of the meanings indicated for $R^{c5}$,
$R^{w6}$ has one of the meanings indicated for $R^{c6}$,
$R^{w7}$ has one of the meanings indicated for $R^{c7}$,
$R^{ww}$ is selected from H, OH, $NH_2$, CN, $CF_3$, $CHF_2$, $CH_2F$, O—$CF_3$, O—$CHF_2$, O—$CH_2F$, COON, $OCH_2COOH$, $C_1$-$C_6$-alkyl, $C_1$-$C_6$-alkoxy, $C_1$-$C_6$-alkoxy-$C_1$-$C_4$-alkyl, where the last 4 radicals mentioned may be partly or completely halogenated and/or have 1, 2 or 3 substituents $R^{wa}$,
$C_3$-$C_7$-cycloalkyl, $C_3$-$C_7$-cycloalkyl-$C_1$-$C_4$-alkyl, $C_3$-$C_7$-cycloalkyloxy, where the cycloalkyl moiety of the last three radicals mentioned may have 1, 2, 3 or 4 radicals $R^{wb}$, aryl, O-aryl, O—$CH_2$-aryl, hetaryl, where the last four radicals mentioned are unsubstituted in the aryl moiety or may carry 1, 2, 3 or 4 radicals $R^{wd}$,
$COOR^{w1}$, $CONR^{w2}R^{w3}$, $SO_2NR^{w2}R^{w3}$, $NR^{w2}$—$SO_2$—$R^{w4}$,
$NR^{w2}$—CO—$R^{w5}$, $SO_2$—$R^{w4}$,
—$(CH_2)_p$—$NR^{w6}R^{w7}$ with p=0, 1, 2, 3, 4, 5 or 6 and O—$(CH_2)_q$—$NR^{w6}R^{w7}$ with q=2, 3, 4, 5 or 6;
or
W forms together with $R^2$ a radical of the formula W3:

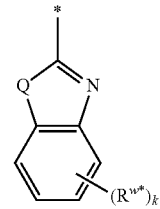

(W3)

in which
* means the linkage to the 6-membered aromatic ring,
Q has one of the meanings indicated for Q in formula W1,
k is 0, 1 or 2, and
$R^{w*}$ has one of the meanings indicated for $R^w$.

The present invention therefore relates to the carboxamide compounds of the general formula I, their tautomers and the pharmaceutically suitable salts of the carboxamide compounds I.

The carboxamide compounds of the invention of the formula I, their salts and their tautomers effectively inhibit calpain even at low concentrations. They additionally show a high selectivity in relation to the inhibition of the calpain compared with other cysteine proteases such as cathepsin B, cathepsin K, cathepsin L and cathepsin S.

The carboxamide compounds of the invention of the formula I, their salts and their tautomers are therefore particularly suitable for treating disorders, impairments and conditions in creatures, especially human creatures, which are associated with an elevated calpain activity.

The invention therefore also relates to the use of carboxamide compounds of the formula I, their tautomers and their pharmaceutically suitable salts for the manufacture of a medicament, in particular of a medicament which is suitable for the treatment of a disorder or a condition which is associated with an elevated calpain activity.

The invention further relates to a medicament, in particular a medicament which is suitable for the treatment of a disorder or a condition which is associated with an elevated calpain activity. The medicament comprises at least one carboxamide compound of the formula I, as described herein, a tautomer or a pharmaceutically suitable salt of the compound I.

The invention further relates to a method for the therapeutic and/or prophylactic treatment of a mammal requiring a treatment, which method comprises administering an effective amount of at least one compound of the formula I as described herein, a tautomer thereof or a pharmaceutically suitable salt thereof, for the treatment of a disease/disorder, of a condition or of an impairment which is associated with an elevated calpain activity or which is set forth in any of the claims.

DETAILED DESCRIPTION OF THE INVENTION

The carboxamide compounds of the formula I may be in the form of β-keto compounds, i.e. the radicals $R^{3a}$ and $R^{3b}$ in the compounds of the formula I form together with the carbon atom to which they are bonded a carbonyl group as shown in the formula on the left in Scheme A. The compounds of the invention may also be in the form of a hydrate, i.e. the radicals $R^{3a}$ and $R^{3b}$ are each OH, as shown in the formula on the right in Scheme A. $R^1$, $R^2$, W, X and Y in Scheme A have the aforementioned meanings.

Scheme A:

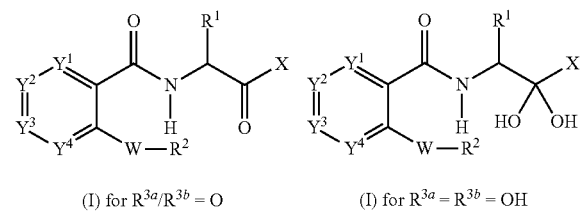

(I) for $R^{3a}/R^{3b} = O$    (I) for $R^{3a} = R^{3b} = OH$

In the presence of water, especially under physiological conditions, usually both the β-keto form and the hydrate form are present in a mixture.

Where only the β-keto form is indicated in the following formulae and descriptions, this is intended to include also the hydrate and mixtures thereof with the β-keto form unless indicated otherwise. Hydrates and β-keto forms are equally suitable as calpain inhibitors.

The carboxamide compounds of the invention of the formula I are also able to form tautomers when $R^{3a}$ and $R^{3b}$ form a carbonyl group together with the carbon atom to which they are bonded. The tautomers are equally suitable as calpain inhibitors. Particular examples of tautomers to be mentioned are the compounds of the formula I-T:

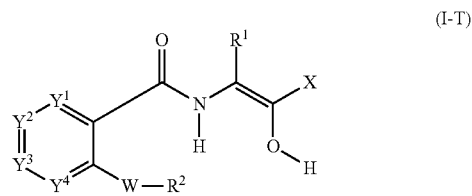

(I-T)

$R^1$, $R^2$, W, X and Y in formula I-T have the aforementioned meanings.

The carboxamide compounds of the invention of the formula I can also form hemiacetals, hemiketals, acetals or ketals with alkanols. These compounds are equally suitable as calpain inhibitors as they are prodrugs of the compounds I, where $CR^{3a}R^{3b}$ is a carbonyl group (i.e. C=O) or $C(OH)_2$. Accordingly, compounds where one or both radicals $R^{3a}$ and $R^{3b}$ are a radical derived from an alkanol, and especially $C_1$-$C_4$-alkoxy, can also be used according to the invention.

The term prodrug, as used herein refers to a compound which is transformed under metabolic conditions into a compound of the formula I. Apart from the aforementioned hemiacetals, hemiketals, acetals and ketals, prodrugs of the compounds I include the compounds of the formula I, wherein $R^{3a}$ and $R^{3b}$ together form a group O-Alk-O, S-Alk-O or S-Alk-S, where Alk is linear $C_2$-$C_5$-alkandiyl, which may be unsubstituted or substituted with 1, 2, 3 or 4 radicals selected from $C_1$-$C_4$-alkyl or halogen, examples for such groups including $O(CH_2)_2O$, $O(CH_2)_5O$, $O(CH_2)_4O$, $S(CH_2)_2O$, $S(CH_2)_5O$, $S(CH_2)_4O$, etc. Further prodrugs of the compounds I include the compounds of the formula I, wherein $R^{3a}$ and $R^{3b}$ together with the carbon atom form a group $C=NR^3$, where $R^3$ is selected from H, $C_1$-$C_6$-alkyl, $C_1$-$C_6$-alkoxy, $C_2$-$C_6$-alkenyl, $C_3$-$C_6$-cycloalkyl, $C_3$-$C_6$-cycloalkyl-$C_1$-$C_4$-alkyl, $C_2$-$C_6$-alkenyloxy, $C_3$-$C_6$-cycloalkyloxy, $C_3$-$C_6$-cycloalkyl-$C_1$-$C_4$-alkyloxy. Under metabolic conditions, the aforementioned prodrugs are transformed into the corresponding β-keto compounds of the formula I ($CR^{3a}R^{3b}$ is C=O) or into the hydrates thereof ($CR^{3a}R^{3b}$ is $C(OH)_2$).

It is equally possible to use pharmaceutically suitable salts of the carboxamide compounds of the formula I, of their tautomers or of their prodrugs, especially acid addition salts with physiologically tolerated organic or inorganic acids. Examples of suitable physiologically tolerated organic and inorganic acids are hydrochloric acid, hydrobromic acid, phosphoric acid, nitric acid, sulfuric acid, organic sulfonic acids having 1 to 12 carbon atoms, e.g. $C_1$-$C_4$-alkylsulfonic acids such as methanesulfonic acid, cycloaliphatic sulfonic acids such as S-(+)-10-camphorsulfonic acids, and aromatic sulfonic acids such as benzenesulfonic acid and toluenesulfonic acid, di- and tricarboxylic acids and hydroxy carboxylic acids having 2 to 10 carbon atoms, such as oxalic acid, malonic acid, maleic acid, fumaric acid, mucic acid, lactic acid, tartaric acid, citric acid, glycolic acid and adipic acid, as well as cis- and trans-cinnamic acid, furan-2-carboxylic acid and benzoic acid. Further suitable acids are described in "Fortschritte der Arzneimittelforschung", Volume 10, pages 224 et seq., Birkhäuser Verlag, Basel and Stuttgart, 1966. The physiologically tolerated salts of the compounds of the formula I may be in the form of mono-, di-, tri- or tetrasalts, meaning that they may comprise 1, 2, 3 or 4 of the aforementioned acid molecules per molecule of the formula I. The acid molecules may be present in their acidic form or as anion.

The compounds of the invention may be in the form of a mixture of diastereomers, or of a mixture of diastereomers in which one of the two diastereomers is enriched, or of essentially diastereomerically pure compounds (diastereomeric excess de>90%). The compounds are preferably in the form of essentially diastereomerically pure compounds (diastereomeric excess de>90%). The compounds I of the invention may furthermore be in the form of a mixture of enantiomers (for example as racemate), of a mixture of enantiomers in which one of the two enantiomers is enriched, or essentially in enantiomerically pure compounds (enantiomeric excess ee>90%). However, the compounds of the invention are frequently prone to racemization in relation to the stereochemistry of the carbon atom which carries the radical $R^1$, so that mixtures are frequently obtained in relation to this carbon atom, or compounds which exhibit a uniform stereochemistry in relation to this C atom form mixtures under physiological conditions. However, in relation to other stereocenters and the occurrence, associated therewith, of enantiomers and diastereomers, it is preferred to employ the compounds enantiomerically pure or diastereomerically pure.

In the context of the present description, unless stated otherwise, the terms "alkyl", "alkoxy", "alkylthio", "haloalkyl", "haloalkoxy", "haloalkylthio", "alkenyl", "alkynyl", "alkylene" and radicals derived therefrom always include both unbranched and branched "alkyl", "alkoxy", "alkylthio", "haloalkyl", "haloalkoxy", "haloalkylthio", "alkenyl", "alkynyl" and "alkylene", respectively.

The prefix $C_n$—$C_m$— indicates the respective number of carbons in the hydrocarbon unit. Unless indicated otherwise, halogenated substituents preferably have one to five identical or different halogen atoms, especially fluorine atoms or chlorine atoms. $C_0$-Alkylene or $(CH_2)_0$ or similar expressions in the context of the description designate, unless indicated otherwise, a single bond.

The term "halogen" designates in each case, fluorine, bromine, chlorine or iodine, specifically fluorine, chlorine or bromine.

Examples of other meanings are:

Alkyl, and the alkyl moieties for example in alkoxy, alkylthio, arylalkyl, hetarylalkyl, cycloalkylalkyl or alkoxyalkyl: saturated, straight-chain or branched hydrocarbon radicals having one or more C atoms, e.g. 1 to 4, 1 to 6 or 1 to 10 carbon atoms, e.g. $C_1$-$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl. In one embodiment of the invention, alkyl stands for small alkyl groups such as $C_1$-$C_4$-alkyl. In another embodiment of the invention, alkyl stands for larger alkyl groups such as $C_5$-$C_{10}$-alkyl.

Haloalkyl: an alkyl radical having ordinarily 1 to 6 or 1 to 4 C atoms as mentioned above, whose hydrogen atoms are partly or completely replaced by halogen atoms such as fluorine, chlorine, bromine and/or iodine, e.g. chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl. Cycloalkyl, and the cycloalkyl moieties for example in cycloalkoxy or cycloalkyl-$C_1$-$C_6$-alkyl: monocyclic, saturated hydrocarbon groups having three or more C atoms, e.g. 3 to 7 carbon ring members, for example 3, 4, 5, 6 or 7 carbon ring members, such as cyclopropyl, cyclobutyl, cyclopentyl, cyclohexyl.

Alkenyl, and alkenyl moieties for example in aryl-($C_2$-$C_6$)-alkenyl: monounsaturated, straight-chain or branched hydrocarbon radicals having two or more C atoms, e.g. 2 to 4, 2 to 6 or 2 to 10 carbon atoms and one double bond in any position, e.g. $C_2$-$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl.

Alkynyl: straight-chain or branched hydrocarbon groups having two or more C atoms, e.g. 2 to 4, 2 to 6 or 2 to 10 carbon atoms and one or two triple bonds in any position but nonadjacent, e.g. $C_2$-$C_6$-alkynyl such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl.

Alkoxy or alkoxy moieties for example in alkoxyalkyl:

Alkyl as defined above having preferably 1 to 6 or 1 to 4 C atoms, which is linked via an O atom: e.g. methoxy, ethoxy, n-propoxy, 1-methylethoxy, butoxy, 1-methylpropoxy, 2-methylpropoxy or 1,1-dimethylethoxy, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy.

Haloalkoxy: alkoxy as described above, in which the hydrogen atoms of these groups are partly or completely replaced by halogen atoms, i.e. for example $C_1$-$C_6$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy, nonafluorobutoxy, 5-fluoro-1-pentoxy, 5-chloro-1-pentoxy, 5-bromo-1-pentoxy, 5-iodo-1-pentoxy, 5,5,5-trichloro-1-pentoxy, undecafluoropentoxy, 6-fluoro-1-hexoxy, 6-chloro-1-hexoxy, 6-bromo-1-hexoxy, 6-iodo-1-hexoxy, 6,6,6-trichloro-1-hexoxy or dodecafluorohexoxy, specifically chloromethoxy, fluoromethoxy, difluoromethoxy, trifluoromethoxy, 2-fluoroethoxy, 2-chloroethoxy or 2,2,2-trifluoroethoxy.

Alkoxyalkyl: an alkyl radical ordinarily having 1 to 4 C atoms, in which one hydrogen atom is replaced by an alkoxy radical ordinarily having 1 to 6 or 1 to 4 C atoms.

Examples thereof are $CH_2$—$OCH_3$, $CH_2$—$OC_2H_5$, n-propoxymethyl, $CH_2$—$OCH(CH_3)_2$, n-butoxymethyl, (1-methylpropoxy)methyl, (2-methylpropoxy)methyl, $CH_2$—$OC(CH_3)_3$, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl, 4-(1,1-dimethylethoxy)butyl, etc.

Alkylthio: alkyl as defined above preferably having 1 to 6 or 1 to 4 C atoms, which is linked via an S atom, e.g. methylthio, ethylthio, n-propylthio and the like.

Haloalkylthio: haloalkyl as defined above preferably having 1 to 6 or 1 to 4 C atoms, which is linked via an S atom, e.g. fluoromethylthio, difluoromethylthio, trifluoromethylthio, 2-fluoroethylthio, 2,2-difluoroethylthio, 2,2,2-trifluoroethylthio, pentafluoroethylthio, 2-fluoropropylthio, 3-fluoropropylthio, 2,2-difluoropropylthio, 2,3-difluoropropylthio, and heptafluoropropylthio.

Aryl: a mono-, bi- or tricyclic aromatic hydrocarbon radical such as phenyl or naphthyl, especially phenyl.

Heterocyclyl: a heterocyclic radical which may be saturated or partly unsaturated and which ordinarily has 3, 4, 5, 6, 7 or 8 ring atoms, where ordinarily 1, 2, 3 or 4, in particular 1, 2 or 3, of the ring atoms are heteroatoms such as N, S or O, besides carbon atoms as ring members.

Examples of saturated heterocycles are in particular:

Heterocycloalkyl: i.e. a saturated heterocyclic radical which ordinarily has 3, 4, 5, 6 or 7 ring atoms, where ordinarily 1, 2 or 3 of the ring atoms are heteroatoms such as N, S or O, besides carbon atoms as ring members. These include for example:

C-bonded, 3-4-membered saturated rings such as
2-oxiranyl, 2-oxetanyl, 3-oxetanyl, 2-aziridinyl, 3-thiethanyl, 1-azetidinyl, 2-azetidinyl.

C-bonded, 5-membered saturated rings such as
tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, tetrahydropyrazol-3-yl, tetrahydropyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 1,3,2-dioxathiolan-4-yl.

C-bonded, 6-membered saturated rings such as:
tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl.

N-bonded, 5-membered saturated rings such as:
tetrahydropyrrol-1-yl, tetrahydropyrazol-1-yl, tetrahydroisoxazol-2-yl, tetrahydroisothiazol-2-yl, tetrahydroimidazol-1-yl, tetrahydrooxazol-3-yl, tetrahydrothiazol-3-yl.

N-bonded, 6-membered saturated rings such as:
piperidin-1-yl, hexahydropyrimidin-1-yl, hexahydropyrazin-1-yl, hexahydropyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl, tetrahydro-1,2-oxazin-2-yl.

Unsaturated heterocyclic radicals which ordinarily have 4, 5, 6 or 7 ring atoms, where ordinarily 1, 2 or 3 of the ring atoms are heteroatoms such as N, S or O, besides carbon atoms as ring members. These include for example:

C-bonded, 5-membered, partially unsaturated rings such as:
2,3-dihydrofuran-2-yl, 2,3-dihydrofuran-3-yl, 2,5-dihydrofuran-2-yl, 2,5-dihydrofuran-3-yl, 4,5-dihydrofuran-2-yl, 4,5-dihydrofuran-3-yl, 2,3-dihydrothien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-5-yl, 2,3-dihydroisothiazol-4-yl, 2,3-dihydroisothiazol-5-yl, 4,5-dihydro-1H-imidazol-2-yl, 4,5-dihydro-1H-imidazol-4-yl, 4,5-dihydro-1H-imidazol-5-yl, 2,5-dihydro- 1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl, 1,3-oxathiol-5-yl.

C-bonded, 6-membered, partially unsaturated rings such as:

2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydrothiopyran-6-yl, 2H-3,4-dihydrothiopyran-5-yl, 2H-3,4-dihydrothiopyran-4-yl, 2H-3,4-dihydrothiopyran-3-yl, 2H-3,4-dihydrothiopyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetrahydropyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 3,4-dihydropyridin-2-yl, 3,4-dihydropyridin-3-yl, 3,4-dihydropyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydropyridazin-4-yl, 1,2,5,6-tetrahydropyridazin-5-yl, 1,2,5,6-tetrahydropyridazin-6-yl, 1,2,3,6-tetrahydropyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5-6-tetrahydropyrimidin-2-yl, 3,4,5,6-tetrahydropyrimidin-4-yl, 3,4,5,6-tetrahydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydropyrimidin-2-yl, 1,2,3,4-tetrahydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4-thiazin-5-yl, 2,3-dihydro-1,4-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-oxazin-4-yl, 6H-1,3-oxazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl or 3,4-dihydropyrimidin-6-yl.

N-bonded, 5-membered, partially unsaturated rings such as:

2,3-dihydro-1H-pyrrol-1-yl, 2,5-dihydro-1H-pyrrol-1-yl, 4,5-dihydro-1H-pyrazol-1-yl, 2,5-dihydro-1H-pyrazol-1-yl, 2,3-dihydro-1H-pyrazol-1-yl, 2,5-dihydroisoxazol-2-yl, 2,3-dihydroisoxazol-2-yl, 2,5-dihydroisothiazol-2-yl, 2,3-dihydroisoxazol-2-yl, 4,5-dihydro-1H-imidazol-1-yl, 2,5-dihydro-1H-imidazol-1-yl, 2,3-dihydro-1H-imidazol-1-yl, 2,3-dihydrooxazol-3-yl, 2,3-dihydrothiazol-3-yl.

N-bonded, 6-membered, partially unsaturated rings such as:

1,2,3,4-tetrahydropyridin-1-yl, 1,2,5,6-tetrahydropyridin-1-yl, 1,4-dihydropyridin-1-yl, 1,2-dihydropyridin-1-yl, 2H-5,6-dihydro-1,2-oxazin-2-yl, 2H-5,6-dihydro-1,2-thiazin-2-yl, 2H-3,6-dihydro-1,2-oxazin-2-yl, 2H-3,6- dihydro-1,2-thiazin-2-yl, 2H-3,4-dihydro-1,2-oxazin-2-yl, 2H-3,4-dihydro-1,2-thiazin-2-yl, 2,3,4,5-tetrahydropyridazin-2-yl, 1,2,5,6-tetrahydropyridazin-1-yl, 1,2,5,6-tetrahydropyridazin-2-yl, 1,2,3,6-tetrahydropyridazin-1-yl, 3,4,5,6-tetrahydropyrimidin-3-yl, 1,2,3,4-tetrahydropyrazin-1-yl, 1,2,3,4-tetrahydropyrimidin-1-yl, 1,2,3,4-tetrahydropyrimidin-3-yl, 2,3-dihydro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4-dihydropyridazin-1-yl, 1,4-dihydropyrazin-1-yl, 1,2-dihydropyrazin-1-yl, 1,4-dihydropyrimidin-1-yl or 3,4-dihydropyrimidin-3-yl.

Hetaryl: a 5- or 6-membered aromatic heterocyclic radical which ordinarily has 1, 2, 3 or 4 nitrogen atoms or a heteroatom selected from oxygen and sulfur and, if appropriate, 1, 2 or 3 nitrogen atoms as ring members besides carbon atoms as ring members: for example C-bonded, 5-membered heteroaromatic radicals having 1, 2, 3 or 4 nitrogen atoms or a heteroatom selected from oxygen and sulfur and, if appropriate, having 1, 2 or 3 nitrogen atoms as ring members, such as:

2-furyl, 3-furyl, 2-thienyl, 3-thienyl, pyrrol-2-yl, pyrrol-3-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, oxazol-2-yl, oxazol-4-yl, oxazol-5-yl, thiazol-2-yl, thiazol-4-yl, thiazol-5-yl, 1,2,3-oxadiazol-4-yl, 1,2,3-oxadiazol-5-yl, 1,2,4-oxadiazol-3-yl, 1,2,4-oxadiazol-5-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl, 1,2,3-triazol-4-yl, 1,2,4-triazol-3-yl, tetrazol-5-yl.

C-bonded, 6-membered heteroaromatic radicals having 1, 2, 3 or 4 nitrogen atoms as ring members, such as:

pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, 1,3,5-triazin-2-yl, 1,2,4-triazin-3-yl, 1,2,4-triazin-5-yl, 1,2,4-triazin-6-yl, 1,2,4,5-tetrazin-3-yl.

N-bonded, 5-membered heteroaromatic radicals having 1, 2, 3 or 4 nitrogen atoms as ring members, such as:

pyrrol-1-yl, pyrazol-1-yl, imidazol-1-yl, 1,2,3-triazol-1-yl, 1,2,4-triazol-1-yl, tetrazol-1-yl.

Heterocyclyl also includes bicyclic heterocycles which have one of the aforementioned 5- or 6-membered heterocyclic rings and a further saturated, unsaturated or aromatic carbocycle fused thereto, for example a benzene, cyclohexane, cyclohexene or cyclohexadiene ring, or a further 5- or 6-membered heterocyclic ring fused thereto, where the latter may likewise be saturated, unsaturated or aromatic. These include for example quinolinyl, isoquinolinyl, indolyl, indolizynyl, isoindolyl, indazolyl, benzofuryl, benzothienyl, benzo[b]thiazolyl, benzoxazolyl, benzthiazolyl and benzimidazolyl. Examples of 5- to 6-membered heteroaromatic compounds comprising a fused benzene ring include dihydroindolyl, dihydroindolizynyl, dihydroisoindolyl, dihydroquinolinyl, dihydroisoquinolinyl, chromenyl and chromanyl.

Arylalkyl: an aryl radical as defined above which is linked via an alkylene group, in particular via a methylene, 1,1-ethylene or 1,2-ethylene group, e.g. benzyl, 1-phenylethyl and 2-phenylethyl.

Arylalkenyl: an aryl radical as defined above, which is linked via an alkenylene group, in particular via a 1,1-ethenyl, 1,2-ethenyl or 1,3-propenyl group, e.g. 2-phenylethen-1-yl and 1-phenylethen-1-yl.

Cycloalkoxy: a cycloalkyl radical as defined above which is linked via an oxygen atom, e.g. cyclopropyloxy, cyclobutyloxy, cyclopentyloxy or cyclohexyloxy.

Cycloalkylalkyl: a cycloalkyl radical as defined above which is linked via an alkylene group, in particular via a methylene, 1,1-ethylene or 1,2-ethylene group, e.g. cyclopropylm ethyl, cyclobutylmethyl, cyclopentylmethyl or cyclohexylmethyl.

Heterocyclylalkyl and hetarylalkyl: a heterocyclyl or hetaryl radical as defined above which is linked via an alkylene group, in particular via a methylene, 1,1-ethylene or 1,2-ethylene group.

The expression "optionally substituted" means in the context of the present invention that the respective moiety is substituted or has 1, 2 or 3, in particular 1, substituents which are selected from halogen, $C_1$-$C_4$-alkyl, OH, SH, CN, $CF_3$, O—$CF_3$, COON, O—$CH_2$—COON, $C_1$-$C_6$-alkoxy, C, $C_6$ alkylthio, $C_3$-$C_7$-cycloalkyl, COO—$C_1$-$C_6$-alkyl, $CONH_2$, CONH—$C_1$-$C_6$-alkyl, $SO_2$NH—$C_1$-$C_6$-alkyl, CON—($C_1$-$C_6$-alkyl)$_2$, $SO_2$N—($C_1$-$C_6$-alkyl)$_2$, NH—$SO_2$—$C_1$-$C_6$-alkyl, NH—CO—$C_1$-$C_6$-alkyl, $SO_2$—$C_1$-$C_6$-alkyl, O-phenyl, O—$CF_{12}$-phenyl, CONH-phenyl, $SO_2$NH-phenyl, CONH-hetaryl, $SO_2$NH-hetaryl, $SO_2$-phenyl, NH—$SO_2$-phenyl, NH—CO-phenyl, NH—$SO_2$-hetaryl and NH—CO-hetaryl, where phenyl and hetaryl in the last 11 radicals mentioned are unsubstituted or may have 1, 2 or 3 substituents which are selected from halogen, $C_1$-$C_4$-alkyl, C, $C_4$ haloalkyl, $C_1$-$C_4$-alkoxy and $C_1$-$C_4$-haloalkoxy.

In relation to their use as calpain inhibitors, the variables $R^1$, $R^2$, W and X preferably have the following meanings, where these represent, both considered on their own and in combination with one another, special embodiments of the compounds of the formula I:

$R^1$ $C_1$-$C_{10}$-alkyl, preferably $C_3$-$C_{10}$-alkyl, which may be partly or completely halogenated and/or have 1, 2 or 3 substituents $R^{1a}$, in particular unsubstituted $C_1$-$C_{10}$-alkyl, specifically unsubstituted $C_3$-$C_{10}$-alkyl, $C_3$-$C_7$-cycloalkyl-$C_1$-$C_4$-alkyl, specifically $C_3$-$C_7$-cycloalkylmethyl, 1-($C_3$-$C_7$-cycloalkyl)ethyl or 2-($C_3$-$C_7$-cycloalkyl)ethyl, where the cycloalkyl moiety may have 1, 2, 3 or 4 radicals $R^{1b}$, very specifically cyclohexylmethyl, phenyl-$C_1$-$C_4$-alkyl and hetaryl-$C_1$-$C_4$-alkyl, in particular benzyl, 1-phenylethyl, 2-phenylethyl, hetarylmethyl, 1-hetarylethyl, 2-hetarylethyl such as thienylmethyl, pyridinylmethyl, where phenyl and hetaryl in the last radicals mentioned may be unsubstituted or carry 1, 2, 3 or 4 identical or different radicals $R^{1c}$.

Preferred among these are compounds of the general formula I where $R^1$ is $C_3$-$C_{10}$-alkyl which is unsubstituted or may be partly or completely halogenated and/or have 1, 2 or 3 substituents $R^{1a}$, in particular $C_3$-$C_{10}$-alkyl and most preferred $C_3$-$C_8$-alkyl.

Likewise preferred among these are compounds of the general formula I where $R^1$ is phenyl-$C_1$-$C_4$-alkyl or hetaryl-$C_1$-$C_4$-alkyl, where phenyl and hetaryl in the last 2 radicals mentioned is unsubstituted or carries 1, 2, 3 or 4 identical or different radicals $R^{1c}$. In hetaryl-$C_1$-$C_4$-alkyl, the hetaryl moiety is preferably pyridyl or thienyl.

In a particular preferred embodiment $R^1$ is phenyl-$C_1$-$C_4$-alkyl and most preferred benzyl, wherein the phenyl ring in phenyl-$C_1$-$C_4$-alkyl or benzyl is unsubstituted or carries 1, 2, 3 or 4 identical or different radicals $R^{1c}$.

In this connection, $R^{1a}$, $R^{1b}$ and $R^{1c}$ where present have the aforementioned meanings. In particular:

$R^{1a}$ is $C_1$-$C_4$-alkoxy or $C_1$-$C_4$-haloalkoxy;

$R^{1b}$ is halogen, $C_1$-$C_4$-alkyl, $C_1$-$C_4$-haloalkyl, $C_1$-$C_4$-alkoxy or $C_1$-$C_4$-haloalkoxy; and $R^{1c}$ is halogen, $C_1$-$C_4$-alkyl, $C_1$-$C_4$-haloalkyl, OH, SH, CN, COON, O—$CH_2$—COON, $C_1$-$C_8$-alkoxy, $C_1$-$C_4$-haloalkoxy, $C_1$-$C_8$-alkylthio, $C_3$-$C_7$-cycloalkyl, COO—$C_1$-$C_8$-alkyl, $CONH_2$, CONH—$C_1$-$C_8$-alkyl, $SO_2NH$—$C_1$-$C_8$-alkyl, CON—$(C_1$-$C_8$-alkyl$)_2$, $SO_2N$—$(C_1$-$C_8$-alkyl$)_2$, NH—$SO_2$—$C_1$-$C_8$-alkyl, NH—CO—$C_1$-$C_6$-alkyl, $SO_2$—$C_1$-$C_8$-alkyl, O-phenyl, O—$CH_2$-phenyl, CONH-phenyl, $SO_2NH$-phenyl, CONH-hetaryl, $SO_2NH$-hetaryl, $SO_2$-phenyl, NH—$SO_2$-phenyl, NH—CO-phenyl, NH—$SO_2$-hetaryl, NH—CO-hetaryl where phenyl and hetaryl in the last 11 radicals mentioned are unsubstituted or may have 1, 2 or 3 substituents which are selected from halogen, $C_1$-$C_4$-alkyl, $C_1$-$C_4$-haloalkyl, $C_1$-$C_4$-alkoxy and $C_1$-$C_4$-haloalkoxy, —$(CH_2)_p$—$NR^{c6}R^{c7}$ with p=0, 1, 2, 3, 4, 5 or 6, in particular 0, and —O—$(CH_2)_q$—$NR^{c6}R^{c7}$ with q=2, 3, 4, 5 or 6, in particular 2, where $R^{c6}$, $R^{c7}$ are independently of one another hydrogen or $C_1$-$C_6$-alkyl, or together with the nitrogen atom to which they are bonded, are a morpholine, piperidine, pyrrolidine, azetidine or piperazine residue, where the last 5 radicals mentioned are unsubstituted or may carry 1, 2, 3 or 4 radicals selected from $C_1$-$C_4$-alkyl, $C_1$-$C_4$-haloalkyl, $C_1$-$C_4$-alkoxy or $C_1$-$C_4$-haloalkoxy.

$R^{1c}$ is in particular halogen, $C_1$-$C_4$-alkyl, $C_1$-$C_4$-haloalkyl, especially $C_1$-$C_2$-fluoroalkyl such as $CF_3$, $CHF_2$, $CH_2F$, specially $CF_3$, $C_1$-$C_4$-alkoxy or $C_1$-$C_4$-haloalkoxy, especially $C_1$-$C_2$-fluoroalkoxy such as O—$CF_3$, O—$CHF_2$ or O—$CH_2F$, specially O—$CF_3$.

$R^2$ is, in particular:

aryl or hetaryl, where aryl and hetaryl in the last 2 radicals mentioned may be unsubstituted or carry 1, 2, 3 or 4 identical or different radicals $R^{2b}$, aryl-$C_1$-$C_6$-alkyl, aryl-$C_2$-$C_6$-alkenyl or hetaryl-$C_1$-$C_4$-alkyl, where aryl and hetaryl in the last 3 radicals mentioned may be unsubstituted or carry 1, 2 or 3 or 4 identical or different radicals $R^{2b}$.

Preferred among these are those compounds of the general formula I in which $R^2$ is selected from aryl and hetaryl, specifically from phenyl, naphthyl, thienyl and pyridyl, and most preferred from phenyl and naphthyl, where aryl and hetaryl (or phenyl, naphthyl, thienyl and pyridyl) may be unsubstituted or carry 1, 2, 3 or 4, in particular 1 or 2, identical or different radicals $R^{2b}$.

In this connection $R^{2b}$ where present has the aforementioned meanings. In particular:

$R^{2b}$ is halogen, $C_1$-$C_4$-alkyl, OH, SH, CN, $CF_3$, O—$CF_3$, COON, O—$CH_2$—COOH, $C_1$-$C_6$-alkoxy, $C_1$-$C_6$-alkylthio, $C_3$-$C_7$-cycloalkyl, COO—$C_1$-$C_6$-alkyl, $CONH_2$, CONH—$C_1$-$C_6$-alkyl, $SO_2NH$—$C_1$-$C_6$-alkyl, CON—$(C_1$-$C_6$-alkyl$)_2$, $SO_2N$—$(C_1$-$C_6$-alkyl$)_2$, NH—$SO_2$—$C_1$-$C_6$-alkyl, NH—CO—$C_1$-$C_6$-alkyl, $SO_2$—$C_1$-$C_6$-alkyl, O-phenyl, O—$CH_2$-phenyl, CONH-phenyl, $SO_2NH$-phenyl, CONH-hetaryl, $SO_2NH$-hetaryl, $SO_2$-phenyl, NH—$SO_2$-phenyl, NH—CO-phenyl, NH—$SO_2$-hetaryl, NH—CO-hetaryl, where phenyl and hetaryl in the last 11 radicals mentioned are unsubstituted or may have 1, 2 or 3 substituents which are selected from halogen, $C_1$-$C_4$-alkyl, $C_1$-$C_4$-haloalkyl, $C_1$-$C_4$-alkoxy and $C_1$-$C_4$-haloalkoxy, —$(CH_2)_p$—$NR^{c6}R^{c7}$ with p=0, 1, 2, 3, 4, 5 or 6, in particular 0, and —O—$(CH_2)_q$—$NR^{c6}R^{c7}$ with q=2, 3, 4, 5 or 6, in particular 2, where $R^{c6}$, $R^{c7}$ are independently of one another hydrogen or $C_1$-$C_6$-alkyl, or together with the nitrogen atom to which they are bonded are a morpholine, piperidine, pyrrolidine, azetidine or piperazine residue, where the last 5 radicals mentioned are unsubstituted or may carry 1, 2, 3 or 4 radicals selected from $C_1$-$C_4$-alkyl, $C_1$-$C_4$-haloalkyl, $C_1$-$C_4$-alkoxy or $C_1$-$C_4$-haloalkoxy.

$R^{3a}$, $R^{3b}$ in particular OH or the group $CR^{3a}R^{3b}$ is a carbonyl group, wherein the latter is most preferred.

W a radical of the formulae W1 or W2, wherein m is 0 or 1, in particular 0, or the group W—$R^2$ is a radical of the formula W3, wherein k is 0 or 1, in particular 0.

Where m or k is 1 or 2, $R^w$ and $R^{w*}$ are preferably selected from halogen, $C_1$-$C_6$-alkyl, $C_1$-$C_6$-alkyl which is substituted by 1, 2 or 3 substituents $R^{wa}$, or OH, SH, CN, COON, O—$CH_2$—COON, $C_1$-$C_6$-haloalkyl, especially $C_1$-$C_2$-fluoroalkyl such as $CF_3$, $CHF_2$, $CH_2F$, specially $CF_3$, $C_1$-$C_6$-alkoxy, $C_1$-$C_6$-haloalkoxy especially $C_1$-$C_2$-fluoroalkoxy such as O—$CF_3$, O—$CHF_2$ or O—$CH_2F$, specially O—$CF_3$, $C_1$-$C_6$-alkylthio, $C_3$-$C_7$-cycloalkyl, COO—$C_1$-$C_6$-alkyl, $CONH_2$, CONH—$C_1$-$C_6$-alkyl, $SO_2NH$—$C_1$-$C_6$-alkyl, CON—$(C_1$-$C_6$-alkyl$)_2$, $SO_2N$—$(C_1$-$C_6$-alkyl$)_2$, NH—$SO_2$—$C_1$-$C_6$-alkyl, NH—CO—$C_1$-$C_6$-alkyl, $SO_2$—$C_1$-$C_6$-alkyl, O-phenyl, O—$CH_2$-phenyl, CONH-phenyl, $SO_2NH$-phenyl, CONH-hetaryl, $SO_2NH$-hetaryl, $SO_2$-phenyl, NH—$SO_2$-phenyl, NH—CO-phenyl, NH—$SO_2$-hetaryl, NH—CO-hetaryl, where phenyl and hetaryl in the last 11 radicals mentioned are unsubstituted or may have 1, 2 or 3 substituents which are selected from halogen, $C_1$-$C_4$-alkyl, $C_1$-$C_4$-haloalkyl, $C_1$-$C_4$-alkoxy and $C_1$-$C_4$-haloalkoxy. $R^w$ and $R^{w*}$ are in particular selected from OH, F, Cl, CN, $CF_3$, $C_1$-$C_6$-alkyl which is unsubstituted or may have 1, 2 or 3 substituents $R^{wa}$, $C_1$-$C_6$-haloalkyl, $C_1$-$C_6$-alkoxy, $C_1$-$C_6$-haloalkoxy and $C_3$-$C_7$-cycloalkyl. In this connection, $R^{wa}$ has the aforementioned meanings and is in particular $C_1$-$C_4$-alkoxy or $C_1$-$C_4$-haloalkoxy. $R^w$ and $R^{w*}$ are particularly preferably selected from F, Cl, CN, $CF_3$, $CH_3$, $C_2H_5$ and $OCH_3$.

Compounds of the formula I which are particularly preferred among the compounds of the invention of the general formula I are those in which W is a radical W1 or W2, wherein in each case Q is selected from S, O and NH, specifically from S and O, and particularly preferred among these are those in which m is 0 or 1 and specifically 0. Particular preference is given to compounds of the formula I, wherein W is W1 or W2 and Q is S.

Compounds of the formula I which are particularly preferred among the compounds of the invention of the general formula I are those in which W—$R^2$ is a radical W3, wherein Q is selected from S, O and NH, specifically from S and O, and particularly preferred among these are those in which m is 0 or 1 and specifically 0. Particular preference is given to compounds of the formula I, wherein W—$R^2$ is a radical W3, wherein Q is S.

X is a radical C(=O)—$NR^{x2}R^{x3}$ in which $R^{x2}$ and $R^{x3}$ have one of the aforementioned meanings. Compounds preferred among these are those in which:

$R^{x2}$ is H, OH, CN, $C_1$-$C_6$-alkyl, $C_1$-$C_6$-haloalkyl, $C_1$-$C_6$-alkyl which has 1, 2 or 3 substituents $R^{xa}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, hetaryl, aryl-$C_1$-$C_4$-alkyl or hetaryl-$C_1$-$C_4$-alkyl, where aryl and hetaryl in the last 4 radicals mentioned are unsubstituted or have 1, 2 or 3 substituents $R^{xd}$. In particular, $R^{x2}$ is hydrogen, $C_1$-$C_6$-alkyl, $C_1$-$C_6$-haloalkyl, $C_1$-$C_6$-alkyl which has 1 or 2 substituents $R^{xa}$, $C_3$-$C_7$-cycloalkyl-$C_1$-$C_4$-alkyl, $C_3$-$C_7$-heterocycloalkyl-$C_1$-$C_4$-alkyl, aryl, hetaryl, aryl-$C_1$-$C_4$-alkyl or hetaryl-$C_1$-$C_4$-alkyl. $R^{x2}$ is very particularly preferably hydrogen.

$R^{x3}$ is H, $C_1$-$C_6$-alkyl, $C_1$-$C_6$-haloalkyl or $C_1$-$C_6$-alkyl which has 1, 2 or 3 substituents $R^{xa}$. In particular, $R^{x3}$ is hydrogen, $C_1$-$C_6$-alkyl, $C_1$-$C_6$-haloalkyl, $C_1$-$C_6$-alkyl which has 1 or 2 substituents $R^{xa}$. $R^{x3}$ is very particularly preferably hydrogen.

Compounds of the formula I which are likewise preferred are those in which the group $NR^{x2}R^{x3}$ is a nitrogen heterocycle of the following formulae:

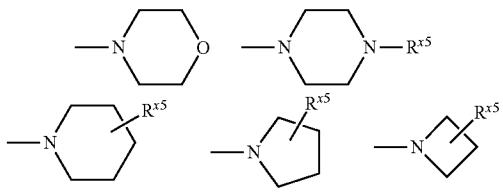

in which $R^{x5}$ is hydrogen or has the meaning indicated for $R^{xb}$. In particular, $R^{x5}$ is $C_1$-$C_6$-alkyl, $C_1$-$C_6$-haloalkyl, $C_1$-$C_6$-alkyl which has 1, 2 or 3 substituents $R^{xa}$, or $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl-$C_1$-$C_4$-alkyl or hetaryl-$C_1$-$C_4$-alkyl, where aryl and hetaryl in the last 2 radicals mentioned are unsubstituted or have 1, 2 or 3 substituents $R^{xd}$, or COO—$C_1$-$C_6$-alkyl, $CONH_2$, CONH—$C_1$-$C_6$-alkyl, $SO_2NH$—$C_1$-$C_6$-alkyl, CON—$(C_1$-$C_6$-alkyl$)_2$, $SO_2N$—$(C_1$-$C_6$-alkyl$)_2$, NH—$SO_2$—$C_1$-$C_6$-alkyl, CONH-phenyl, $SO_2NH$-phenyl, CONH-hetaryl, $SO_2NH$-hetaryl, where phenyl and hetaryl in the last 4 radicals mentioned are unsubstituted or may have 1, 2 or 3 substituents which are selected from the halogen, $C_1$-$C_4$-alkyl, $C_1$-$C_4$-haloalkyl, $C_1$-$C_4$-alkoxy and $C_1$-$C_4$-haloalkoxy. In particular, $R^{x5}$ is hydrogen or $C_1$-$C_4$-alkyl.

In a particularly preferred embodiment of the invention, X is C(O)—$NH_2$.

In another particularly preferred embodiment of the invention, X is C(O)—$NHR^{x2a}$, wherein $R^{x2a}$ has one of the meanings given above for $R^{x2}$, except for hydrogen. In this particular embodiment, $R^{x2a}$ is preferably selected from OH, $C_1$-$C_6$-alkyl, $C_1$-$C_6$-haloalkyl, $C_1$-$C_6$-alkyl which has 1, 2 or 3 substituents $R^{xa}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, O—$C_1$-$C_6$-alkyl, where alkyl, alkoxy, alkenyl, alkynyl, cycloalkyl, heterocycloalkyl in the last 7 radicals mentioned are unsubstituted or have 1, 2 or 3 substituents $R^{xa}$, aryl, O-aryl, O—$CH_2$-aryl, hetaryl, O—$CH_2$-hetaryl, aryl-$C_1$-$C_4$-alkyl and hetaryl-$C_1$-$C_4$-alkyl, where aryl and hetaryl in the last 7 radicals mentioned are unsubstituted or have 1, 2 or 3 substituents $R^{xd}$. Especially, $R^{x2a}$ is selected from $C_1$-$C_6$-alkyl, $C_1$-$C_6$-haloalkyl, $C_2$-$C_6$-alkenyl, $C_3$-$C_7$-cycloalkyl, $C_3$-$C_7$-cycloalkylmethyl, $C_1$-$C_6$-alkoxy-$C_1$-$C_4$-alkyl and O—$C_1$-$C_6$-alkyl.

In another embodiment of the invention, X is hydrogen.

In another embodiment of the invention, X is C(O)OR$^{x1}$ in which $R^{x1}$ has the aforementioned meanings. In particular, $R^{x1}$ is $C_1$-$C_6$-alkyl, $C_1$-$C_6$-haloalkyl, $C_1$-$C_6$-alkyl which has 1, 2 or 3 substituents $R^{xa}$, or $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, hetaryl, aryl-$C_1$-$C_4$-alkyl or hetaryl-$C_1$-$C_4$-alkyl, where aryl and hetaryl in the last 4 radicals mentioned are unsubstituted or have 1, 2 or 3 substituents $R^{xd}$.

In this connection, $R^{xa}$ has the aforementioned meanings and is in particular $C_1$-$C_4$-alkoxy or $C_1$-$C_4$-haloalkoxy. In this connection, $R^{xd}$ has the aforementioned meanings and is preferably F, Cl, OH, COON, C(O)$NH_2$, CN, $NH_2$, $OCH_2COOH$, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, CO—$C_1$-$C_4$-alkyl, CO—O—$C_1$-$C_4$-alkyl, NH—$C_1$-$C_4$-alkyl, NH—C(O)$C_1$-$C_4$-alkyl or $SO_2$—$C_1$-$C_4$-alkyl.

$Y^1$, $Y^2$, $Y^3$ or $Y^4$ are $CR^y$, or one or two of the variables $Y^1$ to $Y^4$ are a nitrogen atom and the remaining variables $Y^1$, $Y^2$, $Y^3$ or $Y^4$ are $CR^y$, wherein the radicals $R^y$ may be identical or different, each having one of the aforementioned meanings.

In a preferred embodiment of the invention, $Y^4$ is N.

In a particular preferred embodiment of the invention, $Y^4$ is N, and $Y^1$, $Y^2$ and $Y^3$ are $CR^y$. Thus, in this embodiment the divalent, 6-membered heteroaromatic radical of formula I that includes the variables $Y^1$ to $Y^4$ is pyridinediyl.

In another particular preferred embodiment of the invention, $Y^4$ and $Y^1$ are N, and $Y^2$ and $Y^3$ are $CR^y$. Thus, in this embodiment the divalent, 6-membered heteroaromatic radical of formula I that includes the variables $Y^1$ to $Y^4$ is pyrazinediyl.

In another particular preferred embodiment of the invention, $Y^4$ and $Y^2$ are N, and $Y^1$ and $Y^3$ are $CR^y$. Thus, in this embodiment the divalent, 6-membered heteroaromatic radical of formula I that includes the variables $Y^1$ to $Y^4$ is pyrimidinediyl.

In yet another particular preferred embodiment of the invention, $Y^1$, $Y^2$, $Y^3$ and $Y^4$ are $CR^y$. Thus, in this embodiment the divalent, 6-membered aromatic radical of formula I that includes the variables $Y^1$ to $Y^4$ is benzdiyl.

The 6-membered (hetero)aromatic radical of formula I that includes the variables $Y^1$ to $Y^4$ preferably has 0, 1 or 2 identical or different substituents $R^y$ other than hydrogen and more preferably 0 or 1 substituent $R^y$ other than hydrogen. Particularly preferred are compounds of formula I, wherein all substituents $R^y$ are hydrogen.

Where a substituent $R^y$ is present that is not hydrogen, it is preferably selected from OH, F, Cl, $NH_2$, CN, $CF_3$, $CHF_2$, O—$CF_3$, O—$CHF_2$, O—$CH_2F$, $C_1$-$C_6$-alkyl, $C_3$-$C_7$-cycloalkyl, $C_1$-$C_6$-alkylamino, $C_1$-$C_6$-dialkylamino, pyrrolidinyl, piperidinyl, morpholinyl, imidazolyl, $C_1$-$C_4$-alkoxy, $C_1$-$C_4$-alkoxy-$C_1$-$C_4$-alkyl, $CONR^{y2}R^{y3}$, $SO_2NR^{y2}R^{y3}$, NH—$SO_2$—$R^{y4}$, —$(CH_2)_p$—$NR^{y6}R^{y7}$, NH—CO—$R^{y5}$, in which p is 0, 1, 2, 3, 4, or 5, and in which $R^{y2}$, $R^{y3}$, $R^{y4}$, $R^{y5}$, $R^{y6}$, $R^{y7}$ have the aforementioned meanings, preferably the meanings mentioned as preferred below, and are in particular H and $C_1$-$C_6$-alkyl, phenyl, benzyl and O-benzyl, where the phenyl ring in the last 3 groups mentioned may have 1, 2 or 3 substituents selected from halogen, OH, SH, $NO_2$, COON, C(O)$NH_2$, CHO, CN, $NH_2$, $OCH_2COOH$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, CO—$C_1$-$C_6$-alkyl, CO—O—$C_1$-$C_6$-alkyl, NH—$C_1$-$C_6$-alkyl, NHCHO, NH—C(O)$C_1$-$C_6$-alkyl, and $SO_2$—$C_1$-$C_6$-alkyl.

In particular, $R^y$ that is not hydrogen, is OH, F, Cl, $NH_2$, CN, $CF_3$, $CHF_2$, O—$CF_3$, O—$CHF_2$, O—$CH_2F$, $C_1$-$C_6$-alkyl, $C_3$-$C_7$-cycloalkyl, $C_1$-$C_6$-alkylamino, $C_1$-$C_6$-dialkylamino, pyrrolidinyl, piperidinyl, morpholinyl, imidazolyl, $C_1$-$C_4$-alkoxy, $C_1$-$C_4$-alkoxy-$C_1$-$C_4$-alkyl, CONH—$C_1$-$C_6$-alkyl, $SO_2N(C_1$-$C_6$-alkyl$)_2$, NH—$SO_2$—$C_1$-$C_6$-alkyl, NH—CO—$C_1$-$C_6$-alkyl, $(CH_2)_p$—$N(C_1$-$C_6$-alkyl$)_2$, in which p is 2, 3 or 4.

$R^y$ that is not hydrogen, is particularly preferably F, Cl, CN, $CF_3$, $CHF_2$, O—$CF_3$, O—$CHF_2$, O—$CH_2F$ or $C_1$-$C_3$-alkyl.

More preferred are compounds of the formula I wherein:
W is W1, wherein Q is O, S or NH,
$R^1$ is phenyl-$C_1$-$C_4$-alkyl, which is unsubstituted or carries 1, 2, 3 or 4 identical or different radicals $R^{1c}$,
$R^2$ is phenyl or is naphthyl, where phenyl and naphthyl may be unsubstituted or substituted with 1 or 2 identical or different radicals $R^{2b}$,
X is $CONH_2$, and
$R^{3a}$ and $R^{3b}$ are each OH or the group $CR^{3a}R^{3b}$ is a carbonyl group.

Also more preferred are compounds of the formula I wherein:
W is W1, wherein Q is O, S or NH, in particular O or S,
$R^1$ is $C_3$-$C_8$-alkyl,
$R^2$ is phenyl or is naphthyl, where phenyl and naphthyl may be unsubstituted or substituted with 1 or 2 identical or different radicals $R^{2b}$,
X is $CONH_2$, and
$R^{3a}$ and $R^{3b}$ are each OH or the group $CR^{3a}R^{3b}$ is a carbonyl group.

Also more preferred are compounds of the formula I wherein:
W is W2, wherein Q is O, S or NH, in particular O or S,
$R^1$ is phenyl-$C_1$-$C_4$-alkyl, which is unsubstituted or carries 1, 2, 3 or 4 identical or different radicals $R^{1c}$,
$R^2$ is phenyl or is naphthyl, where phenyl and naphthyl may be unsubstituted or substituted with 1 or 2 identical or different radicals $R^{2b}$,
X is $CONH_2$, and
$R^{3a}$ and $R^{3b}$ are each OH or the group $CR^{3a}R^{3b}$ is a carbonyl group.

Also more preferred are compounds of the formula I wherein:
W is W2, wherein Q is O, S or NH, in particular O or S,
$R^1$ is $C_3$-$C_8$-alkyl,
$R^2$ is phenyl or is naphthyl, where phenyl and naphthyl may be unsubstituted or substituted with 1 or 2 identical or different radicals $R^{2b}$,
X is $CONH_2$, and
$R^{3a}$ and $R^{3b}$ are each OH or the group $CR^{3a}R^{3b}$ is a carbonyl group.

Also more preferred are compounds of the formula I wherein:
W—$R^2$ is W3, wherein Q is O, S or NH, in particular O or S,
$R^1$ is phenyl-$C_1$-$C_4$-alkyl, which is unsubstituted or carries 1, 2, 3 or 4 identical or different radicals $R^{1c}$,
X is $CONH_2$, and
$R^{3a}$ and $R^{3b}$ are each OH or the group $CR^{3a}R^{3b}$ is a carbonyl group.

Also more preferred are compounds of the formula I wherein:
W—$R^2$ is W3, wherein Q is O, S or NH, in particular O or S,
$R^1$ is $C_3$-$C_8$-alkyl,
X is $CONH_2$, and
$R^{3a}$ and $R^{3b}$ are each OH or the group $CR^{3a}R^{3b}$ is a carbonyl group.

Also more preferred are compounds of the formula I wherein:
W is W1, wherein Q is O, S or NH,
$R^1$ is phenyl-$C_1$-$C_4$-alkyl, which is unsubstituted or carries 1, 2, 3 or 4 identical or different radicals $R^{1c}$,
$R^2$ is phenyl or is naphthyl, where phenyl and naphthyl may be unsubstituted or substituted with 1 or 2 identical or different radicals $R^{2b}$,
X is $CONHR^{x2a}$, wherein $R^{x2a}$ are as defined above and
$R^{3a}$ and $R^{3b}$ are each OH or the group $CR^{3a}R^{3b}$ is a carbonyl group.

Also more preferred are compounds of the formula I wherein:
W is W1, wherein Q is O, S or NH, in particular O or S,
$R^1$ is $C_3$-$C_8$-alkyl,
$R^2$ is phenyl or is naphthyl, where phenyl and naphthyl may be unsubstituted or substituted with 1 or 2 identical or different radicals $R^{2b}$,
X is $CONHR^{x2a}$, wherein $R^{x2a}$ are as defined above and
$R^{3a}$ and $R^{3b}$ are each OH or the group $CR^{3a}R^{3b}$ is a carbonyl group.

Also more preferred are compounds of the formula I wherein:
W is W2, wherein Q is O, S or NH, in particular O or S,
$R^1$ is phenyl-$C_1$-$C_4$-alkyl, which is unsubstituted or carries 1, 2, 3 or 4 identical or different radicals $R^{1c}$,
$R^2$ is phenyl or is naphthyl, where phenyl and naphthyl may be unsubstituted or substituted with 1 or 2 identical or different radicals $R^{2b}$,
X is $CONHR^{x2a}$, wherein $R^{x2a}$ are as defined above and
$R^{3a}$ and $R^{3b}$ are each OH or the group $CR^{3a}R^{3b}$ is a carbonyl group.

Also more preferred are compounds of the formula I wherein:
W is W2, wherein Q is O, S or NH, in particular O or S,
$R^1$ is $C_3$-$C_8$-alkyl,
$R^2$ is phenyl or is naphthyl, where phenyl and naphthyl may be unsubstituted or substituted with 1 or 2 identical or different radicals $R^{2b}$,
X is $CONHR^{x2a}$, wherein $R^{x2a}$ are as defined above and
$R^{3a}$ and $R^{3b}$ are each OH or the group Gee is a carbonyl group.

Also more preferred are compounds of the formula I wherein:
W—$R^2$ is W3, wherein Q is O, S or NH, in particular O or S,
$R^1$ is phenyl-$C_1$-$C_4$-alkyl, which is unsubstituted or carries 1, 2, 3 or 4 identical or different radicals $R^{1c}$,
X is $CONHR^{x2a}$, wherein $R^{x2a}$ are as defined above and
$R^{3a}$ and $R^{3b}$ are each OH or the group $CR^{3a}R^{3b}$ is a carbonyl group.

Also more preferred are compounds of the formula I wherein:
W—$R^2$ is W3, wherein Q is O, S or NH, in particular O or S,
$R^1$ is $C_3$-$C_8$-alkyl, X is CONHR$^{x2a}$, wherein R$^{x2a}$ are as defined above and R$^{3a}$ and R$^{3b}$ are each OH or the group Gee is a carbonyl group.

Otherwise, the radicals R$^{x4}$, R$^{ya}$, R$^{wa}$, R$^{yb}$, R$^{wb}$, R$^{yd}$, R$^{wd}$, R$^{a1}$, R$^{b1}$, R$^{c1}$, R$^{y1}$, R$^{w1}$, R$^{a2}$, R$^{b2}$, R$^{c2}$, R$^{y2}$, R$^{w2}$, R$^{a3}$, R$^{b3}$, R$^{c3}$, R$^{y3}$, R$^{w3}$, R$^{a4}$, R$^{b4}$, R$^{c4}$, R$^{y4}$, R$^{w4}$, R$^{a5}$, R$^{b5}$, R$^{c5}$, R$^{y5}$, R$^{w5}$, R$^{a6}$, R$^{b6}$, R$^{c6}$, R$^{y6}$, R$^{w6}$, R$^{a7}$, R$^{b7}$, R$^{c7}$, R$^{y7}$, R$^{w7}$, and R$^{ww}$ have, unless otherwise indicated, independently of one another preferably one of the following meanings:

R$^{x4}$: hydrogen or C$_1$-C$_8$-alkyl.

R$^{ya}$, R$^{wa}$ independently of one another: C$_1$-C$_4$-alkoxy or C$_1$-C$_4$-haloalkoxy.

R$^{yb}$, R$^{wb}$ independently of one another: halogen, C$_1$-C$_4$-alkyl, C$_1$-C$_4$-haloalkyl, C$_1$-C$_4$-alkoxy or C$_1$-C$_4$-haloalkoxy.

R$^{yd}$, R$^{wd}$ independently of one another: F, Cl, OH, COON, C(O)NH$_2$, CN, NH$_2$, OCH$_2$COOH, C$_1$-C$_4$-alkyl, C$_1$-C$_4$-haloalkyl, C$_1$-C$_4$-alkoxy, C$_1$-C$_4$-haloalkoxy, C$_1$-C$_4$-alkylthio, C$_1$-C$_4$-haloalkylthio, CO—C$_1$-C$_4$-alkyl, CO—O—C$_1$-C$_4$-alkyl, NH—C$_1$-C$_4$-alkyl, NH—C(O)C$_1$-C$_4$-alkyl or SO$_2$—C$_1$-C$_4$-alkyl.

R$^{a1}$, R$^{b1}$, R$^{c1}$, R$^{y1}$, R$^{w1}$ independently of one another: hydrogen, C$_1$-C$_8$-alkyl, C$_1$-C$_8$-haloalkyl, phenyl, benzyl, hetaryl and hetarylmethyl, where phenyl and hetaryl in the last 4 radicals mentioned are unsubstituted or have 1, 2 or 3 substituents which are selected from halogen, C$_1$-C$_4$-alkyl, C$_1$-C$_4$-haloalkyl, C$_1$-C$_4$-alkoxy and C$_1$-C$_4$-haloalkoxy.

R$^{a2}$, R$^{b2}$, R$^{c2}$, R$^{y2}$, R$^{w2}$ independently of one another: hydrogen, C$_1$-C$_6$-alkyl, phenyl, benzyl, hetaryl and hetarylmethyl, where phenyl and hetaryl in the last 4 radicals mentioned are unsubstituted or have 1, 2 or 3 substituents which are selected from halogen, C$_1$-C$_4$-alkyl, C$_1$-C$_4$-haloalkyl, C$_1$-C$_4$-alkoxy and C$_1$-C$_4$-haloalkoxy.

R$^{a3}$, R$^{b3}$, R$^{c3}$, R$^{y3}$, R$^{w3}$ independently of one another: hydrogen or C$_1$-C$_6$-alkyl, or R$^{a2}$ with R$^{a3}$ (and likewise R$^{b2}$ with R$^{b3}$, R$^{c2}$ with R$^{c3}$, R$^{y2}$ with R$^{y3}$ and R$^{w2}$ with R$^{w3}$) together with the nitrogen atom to which they are bonded are a morpholine, piperidine, pyrrolidine, azetidine or piperazine residue, where the last 5 radicals mentioned are unsubstituted or may carry 1, 2, 3 or 4 radicals selected from C$_1$-C$_4$-alkyl, C$_1$-C$_4$-haloalkyl, C$_1$-C$_4$-alkoxy or C$_1$-C$_4$-haloalkoxy.

R$^{a4}$, R$^{b4}$, R$^{c4}$, R$^{y4}$, R$^{w4}$ independently of one another: hydrogen, C$_1$-C$_6$-alkyl, phenyl, benzyl, hetaryl and hetarylmethyl, where phenyl and hetaryl in the last 4 radicals mentioned are unsubstituted or have 1, 2 or 3 substituents which are selected from halogen, C$_1$-C$_4$-alkyl, C$_1$-C$_4$-haloalkyl, C$_1$-C$_4$-alkoxy and C$_1$-C$_4$-haloalkoxy.

R$^{a5}$, R$^{b5}$, R$^{c5}$, R$^{y5}$, R$^{w5}$ independently of one another: hydrogen, C$_1$-C$_6$-alkyl, phenyl, benzyl, hetaryl and hetarylmethyl, where phenyl and hetaryl in the last 4 radicals mentioned are unsubstituted or have 1, 2 or 3 substituents which are selected from halogen, C$_1$-C$_4$-alkyl, C$_1$-C$_4$-haloalkyl, C$_1$-C$_4$-alkoxy and C$_1$-C$_4$-haloalkoxy.

R$^{a6}$, R$^{b6}$, R$^{c6}$, R$^{y6}$, R$^{w6}$ independently of one another: hydrogen, C$_1$-C$_6$-alkyl, phenyl, benzyl, hetaryl and hetarylmethyl, where phenyl and hetaryl in the last 4 radicals mentioned are unsubstituted or have 1, 2 or 3 substituents which are selected from halogen, C$_1$-C$_4$-alkyl, C$_1$-C$_4$-haloalkyl, C$_1$-C$_4$-alkoxy and C$_1$-C$_4$-haloalkoxy.

R$^{a7}$, R$^{b7}$, R$^{c7}$, R$^{y7}$, R$^{w7}$ independently of one another: hydrogen or C$_1$-C$_6$-alkyl, or R$^{a6}$ with R$^{a7}$ (and likewise R$^{b6}$ with R$^{b7}$, R$^{c6}$ with R$^{c7}$, R$^{y6}$ with R$^{y7}$ and R$^{w6}$ with R$^{w7}$) together with the nitrogen atom to which they are bonded are a morpholine, piperidine, pyrrolidine, azetidine or piperazine residue, where the last 5 radicals mentioned are unsubstituted or may carry 1, 2, 3 or 4 radicals selected from C$_1$-C$_4$-alkyl, C$_1$-C$_4$-haloalkyl, C$_1$-C$_4$-alkoxy or C$_1$-C$_4$-haloalkoxy, R$^{ww}$: hydrogen or C$_1$-C$_4$-alkyl.

Preferred among the carboxamide compounds of the invention of the formula I are those compounds which correspond to the general formula I-A,

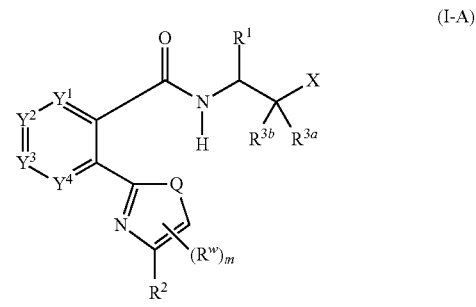

(I-A)

in which m, X, Q, Y$^1$, Y$^2$, Y$^3$, Y$^4$, R$^1$, R$^2$, R$^{3a}$, R$^{3b}$ and R$^w$ have the aforementioned meanings, in particular the meanings mentioned as preferred. In formula I-A m is preferably 0 or 1 and particularly 0. The variable Q is preferably a sulfur atom, a oxygen atom or a NH-moiety. Preferably, the variable Y$^4$ is a nitrogen atom and the remaining variables Y$^1$, Y$^2$ and Y$^3$ are each a CH-moiety, or the variables Y$^1$ and Y$^4$ or Y$^2$ and Y$^4$ are each a nitrogen atom and the remaining variables Y$^2$ and Y$^3$ or Y$^1$ and Y$^3$ are each a CH-moiety, or all variables Y$^1$, Y$^2$, Y$^3$ and Y$^4$ are each a CH-moiety. Also preferred are the tautomers of I-A, the pharmaceutically suitable salts thereof and the tautomers thereof.

Also preferred among the carboxamide compounds of the invention of the formula I are those compounds which correspond to the general formula I-B,

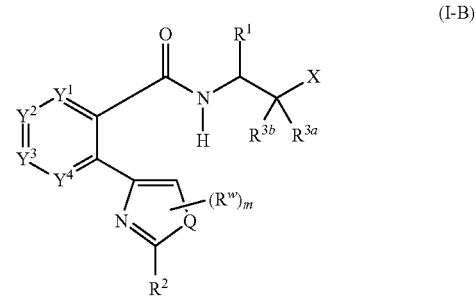

(I-B)

in which m, X, Q, Y$^1$, Y$^2$, Y$^3$, Y$^4$, R$^1$, R$^2$, R$^{3a}$, R$^{3b}$ and R$^w$ have the aforementioned meanings, in particular the meanings mentioned as preferred. In formula I-B m is preferably 0 or 1 and particularly 0. The variable Q is preferably a sulfur atom, a oxygen atom or a NH-moiety. Preferably, the variable Y$^4$ is a nitrogen atom and the remaining variables Y$^1$, Y$^2$ and Y$^3$ are each a CH-moiety, or the variables Y$^1$ and Y$^4$ or Y$^2$ and Y$^4$ are each a nitrogen atom and the remaining variables Y$^2$ and Y$^3$ or Y$^1$ and Y$^3$ are each a CH-moiety, or all variables Y$^1$, Y$^2$, Y$^3$ and Y$^4$ are each a CH-moiety. Also preferred are the tautomers of I-B, the pharmaceutically suitable salts thereof and the tautomers thereof.

Also preferred among the carboxamide compounds of the invention of the formula I are those compounds which correspond to the general formula I-C,

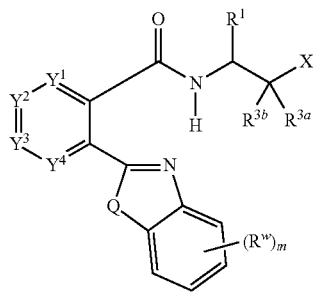

(I-C)

in which m, X, Q, $Y^1, Y^2, Y^3, Y^4, R^1, R^{3a}, R^{3b}$ and $R^w$ have the aforementioned meanings, in particular the meanings mentioned as preferred. In formula I-C m is preferably 0 or 1 and particularly 0. The variable Q is preferably a sulfur atom, a oxygen atom or a NH-moiety. Preferably, the variable $Y^4$ is a nitrogen atom and the remaining variables $Y^1, Y^2$ and $Y^3$ are each a CH-moiety, or the variables $Y^1$ and $Y^4$ or $Y^2$ and $Y^4$ are each a nitrogen atom and the remaining variables $Y^2$ and $Y^3$ or $Y^1$ and $Y^3$ are each a CH-moiety, or all variables $Y^1, Y^2, Y^3$ and $Y^4$ are each a CH-moiety. Also preferred are the tautomers of I-C, the pharmaceutically suitable salts thereof and the tautomers thereof.

Also preferred among the carboxamide compounds of the invention of the formula I are those compounds which correspond to the general formula I-a,

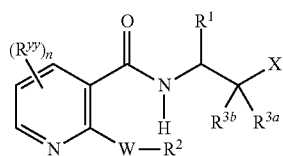

(I-a)

in which X, W, $R^1, R^2, R^{3a}, R^{3b}$, have the aforementioned meanings. $R^{yy}$ has one of the meanings indicated for $R^y$ that are different from hydrogen, in particular the meanings mentioned as preferred. The variable n is preferably 0 or 1 and particularly 0. W is preferably selected from W1 or W2, wherein in each case Q is preferably selected from S, O and NH, or W together with $R^2$ forms a radical W3, wherein Q is preferably selected from S, O and NH. Also preferred are the tautomers of I-a, the pharmaceutically suitable salts thereof and the tautomers thereof.

Also preferred among the carboxamide compounds of the invention of the formula I are those compounds which correspond to the general formula I-b,

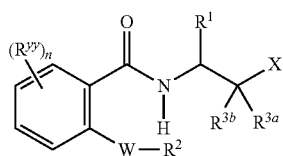

(I-b)

in which X, W, $R^1, R^2, R^{3a}, R^{3b}$, have the aforementioned meanings. $R^{yy}$ has one of the meanings indicated for $R^y$ that are different from hydrogen, in particular the meanings mentioned as preferred. The variable n is preferably 0 or 1 and particularly 0. W is preferably selected from W1 or W2, wherein in each case Q is preferably selected from S, O and NH, or W together with $R^2$ forms a radical W3, wherein Q is preferably selected from S, O and NH. Also preferred are the tautomers of I-b, the pharmaceutically suitable salts thereof and the tautomers thereof.

Also preferred among the carboxamide compounds of the invention of the formula I are those compounds which correspond to the general formula I-c,

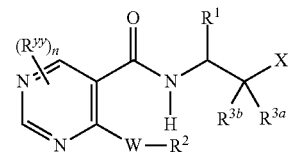

(I-c)

in which X, W, $R^1, R^2, R^{3a}, R^{3b}$, have the aforementioned meanings. $R^{yy}$ has one of the meanings indicated for $R^y$ that are different from hydrogen, in particular the meanings mentioned as preferred. The variable n is preferably 0 or 1 and particularly 0. W is preferably selected from W1 or W2, wherein in each case Q is preferably selected from S, O and NH, or W together with $R^2$ forms a radical W3, wherein Q is preferably selected from S, O and NH. Also preferred are the tautomers of I-c, the pharmaceutically suitable salts thereof and the tautomers thereof.

Also preferred among the carboxamide compounds of the invention of the formula I are those compounds which correspond to the general formula I-d,

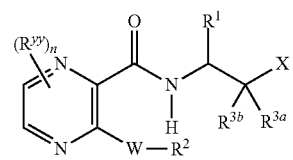

(I-d)

in which X, W, $R^1, R^2, R^{3a}, R^{3b}$, have the aforementioned meanings. $R^{yy}$ has one of the meanings indicated for $R^y$ that are different from hydrogen, in particular the meanings mentioned as preferred. The variable n is preferably 0 or 1 and particularly 0. W is preferably selected from W1 or W2, wherein in each case Q is preferably selected from S, O and NH, or W together with $R^2$ forms a radical W3, wherein Q is preferably selected from S, O and NH. Also preferred are the tautomers of I-d, the pharmaceutically suitable salts thereof and the tautomers thereof.

Particularly preferred are compounds of the formulae I-a and I-b wherein:
W is W1, wherein Q is O, S or NH,
$R^1$ is phenyl-$C_1$-$C_4$-alkyl, which is unsubstituted or carries 1, 2, 3 or 4 identical or different radicals $R^{1c}$,
$R^2$ is phenyl or is naphthyl, where phenyl and naphthyl may be unsubstituted or substituted with 1 or 2 identical or different radicals $R^{2b}$,
X is $CONH_2$, and
$R^{3a}$ and $R^{3b}$ are each OH or the group $CR^{3a}R^{3b}$ is a carbonyl group.

Likewise particularly preferred are compounds of the formulae I-a and I-b wherein:
W is W1, wherein Q is O, S or NH, in particular O or S,
$R^1$ is $C_3$-$C_8$-alkyl, $R^2$ is phenyl or is naphthyl, where phenyl and naphthyl may be unsubstituted or substituted with 1 or 2 identical or different radicals $R^{2b}$,
X is $CONH_2$, and
$R^{3a}$ and $R^{3b}$ are each OH or the group $CR^{3a}R^{3b}$ is a carbonyl group.

Likewise particularly preferred are compounds of the formulae I-a and I-b wherein:
W is W2, wherein Q is O, S or NH, in particular O or S,
$R^1$ is phenyl-$C_1$-$C_4$-alkyl, which is unsubstituted or carries 1, 2, 3 or 4 identical or different radicals $R^{1c}$,
$R^2$ is phenyl or is naphthyl, where phenyl and naphthyl may be unsubstituted or substituted with 1 or 2 identical or different radicals $R^{2b}$,
X is $CONH_2$, and
$R^{3a}$ and $R^{3b}$ are each OH or the group $CR^{3a}R^{3b}$ is a carbonyl group.

Likewise particularly preferred are compounds of the formulae I-a and I-b wherein:
W is W2, wherein Q is O, S or NH, in particular O or S,
$R^1$ is $C_3$-$C_8$-alkyl,
$R^2$ is phenyl or is naphthyl, where phenyl and naphthyl may be unsubstituted or substituted with 1 or 2 identical or different radicals $R^{2b}$,
X is $CONH_2$, and
$R^{3a}$ and $R^{3b}$ are each OH or the group $CR^{3a}R^{3b}$ is a carbonyl group.

Likewise particularly preferred are compounds of the formulae I-a and I-b wherein:
W—$R^2$ is W3, wherein Q is O, S or NH, in particular O or S,
$R^1$ is phenyl-$C_1$-$C_4$-alkyl, which is unsubstituted or carries 1, 2, 3 or 4 identical or different radicals $R^{1c}$,
X is $CONH_2$, and
$R^{3a}$ and $R^{3b}$ are each OH or the group $CR^{3a}R^{3b}$ is a carbonyl group.

Likewise particularly preferred are compounds of the formulae I-a and I-b wherein:
W—$R^2$ is W3, wherein Q is O, S or NH, in particular O or S,
$R^1$ is $C_3$-$C_8$-alkyl,
X is $CONH_2$, and
$R^{3a}$ and $R^{3b}$ are each OH or the group $CR^{3a}R^{3b}$ is a carbonyl group.

Likewise particularly preferred are compounds of the formulae I-a and I-b wherein:
W is W1, wherein Q is O, S or NH,
$R^1$ is phenyl-$C_1$-$C_4$-alkyl, which is unsubstituted or carries 1, 2, 3 or 4 identical or different radicals $R^{1c}$,
$R^2$ is phenyl or is naphthyl, where phenyl and naphthyl may be unsubstituted or substituted with 1 or 2 identical or different radicals $R^{2b}$,
X is $CONHR^{x2a}$, wherein $R^{x2a}$ are as defined above and
$R^{3a}$ and $R^{3b}$ are each OH or the group $CR^{3a}R^{3b}$ is a carbonyl group.

Likewise particularly preferred are compounds of the formulae I-a and I-b wherein:
W is W1, wherein Q is O, S or NH, in particular O or S,
$R^1$ is $C_3$-$C_8$-alkyl,
$R^2$ is phenyl or is naphthyl, where phenyl and naphthyl may be unsubstituted or substituted with 1 or 2 identical or different radicals $R^{2b}$,
X is $CONHR^{x2a}$, wherein $R^{x2a}$ are as defined above and
$R^{3a}$ and $R^{3b}$ are each OH or the group $CR^{3a}R^{3b}$ is a carbonyl group.

Likewise particularly preferred are compounds of the formulae I-a and I-b wherein:
W is W2, wherein Q is O, S or NH, in particular O or S,
$R^1$ is phenyl-$C_1$-$C_4$-alkyl, which is unsubstituted or carries 1, 2, 3 or 4 identical or different radicals $R^{1c}$,
$R^2$ is phenyl or is naphthyl, where phenyl and naphthyl may be unsubstituted or substituted with 1 or 2 identical or different radicals $R^{2b}$,
X is $CONHR^{x2a}$, wherein $R^{x2a}$ are as defined above and
$R^{3a}$ and $R^{3b}$ are each OH or the group $CR^{3a}R^{3b}$ is a carbonyl group.

Likewise particularly preferred are compounds of the formulae I-a and I-b wherein:
W is W2, wherein Q is O, S or NH, in particular O or S,
$R^1$ is $C_3$-$C_8$-alkyl,
$R^2$ is phenyl or is naphthyl, where phenyl and naphthyl may be unsubstituted or substituted with 1 or 2 identical or different radicals $R^{2b}$,
X is $CONHR^{x2a}$, wherein $R^{x2a}$ are as defined above and
$R^{3a}$ and $R^{3b}$ are each OH or the group $CR^{3a}R^{3b}$ is a carbonyl group.

Likewise particularly preferred are compounds of the formulae I-a and I-b wherein:
W—$R^2$ is W3, wherein Q is O, S or NH, in particular O or S,
$R^1$ is phenyl-$C_1$-$C_4$-alkyl, which is unsubstituted or carries 1, 2, 3 or 4 identical or different radicals $R^{1c}$,
X is $CONHR^{x2a}$, wherein $R^{x2a}$ are as defined above and
$R^{3a}$ and $R^{3b}$ are each OH or the group $CR^{3a}R^{3b}$ is a carbonyl group.

Likewise particularly preferred are compounds of the formulae I-a and I-b wherein:
W—$R^2$ is W3, wherein Q is O, S or NH, in particular O or S,
$R^1$ is $C_3$-$C_8$-alkyl,
X is $CONHR^{x2a}$, wherein $R^{x2a}$ are as defined above and
$R^{3a}$ and $R^{3b}$ are each OH or the group $CR^{3a}R^{3b}$ is a carbonyl group.

In turn preferred among the carboxamide compounds of the invention of the formula I-A are compounds which correspond to the general formulae I-A.a, I-A.b, I-A.c or I-A.d,

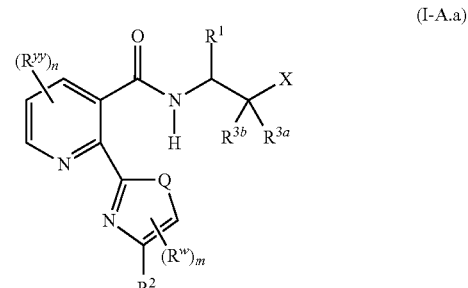
(I-A.a)

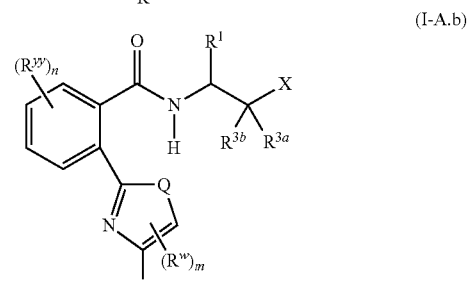
(I-A.b)

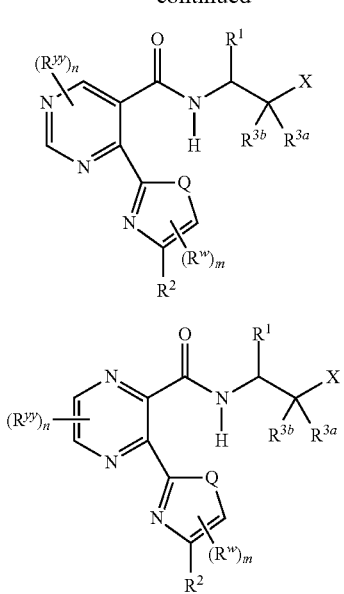

in which n, $R^{yy}$, m, $R^W$, Q, X, $R^1$, $R^2$, $R^{3a}$ and $R^{3b}$ have the aforementioned meanings, in particular those mentioned as preferred.

Particularly preferred are compounds of the formulae I-A.a and I-A.b wherein:

m is 0;

$R^1$ is phenyl-$C_1$-$C_4$-alkyl, which is unsubstituted or carries 1, 2, 3 or 4 identical or different radicals $R^{1c}$, $R^2$ is phenyl or is naphthyl, where phenyl and naphthyl may be unsubstituted or substituted with 1 or 2 identical or different radicals $R^{2b}$, X is $CONH_2$ or $CONHR^{x2a}$, wherein $R^{x2a}$ are as defined above, and $R^{3a}$ and $R^{3b}$ are each OH or the group Gee is a carbonyl group.

Particularly preferred are compounds of the formulae I-A.a and I-A.b wherein:

m is 0;

$R^1$ is $C_3$-$C_8$-alkyl, $R^2$ is phenyl or is naphthyl, where phenyl and naphthyl may be unsubstituted or substituted with 1 or 2 identical or different radicals $R^{2b}$, X is $CONH_2$ or $CONHR^{x2a}$, wherein $R^{x2a}$ are as defined above, and $R^{3a}$ and $R^{3b}$ are each OH or the group Gee is a carbonyl group.

Preferred examples of compounds of formula I-A.a and I-A.b comprise

N-(4-amino-3,4-dioxo-1-phenylbutan-2-yl)-2-(5-phenyl-1H-imidazol-2-yl)pyridine-3-carboxamide, N-(4-amino-3,4-dioxo-1-phenylbutan-2-yl)-2-[4-(4-fluorophenyl)-1,3-thiazol-2-yl]pyridine-3-carboxamide, N-(4-amino-3,4-dioxo-1-phenylbutan-2-yl)-2-{4-[3-(trifluoromethyl)phenyl]-1,3-thiazol-2-yl}pyridine-3-carboxamide, N-(4-amino-3,4-dioxo-1-phenylbutan-2-yl)-2-(4-phenyl-1,3-thiazol-2-yl)pyridine-3-carboxamide, N-(4-amino-3,4-dioxo-1-phenylbutan-2-yl)-2-[4-(2-chlorophenyl)-1,3-thiazol-2-yl]pyridine-3-carboxamide, N-(4-amino-3,4-dioxo-1-phenylbutan-2-yl)-2-[4-(naphthalen-2-yl)-1,3-thiazol-2-yl]pyridine-3-carboxamide, N-(1-amino-1,2-dioxoheptan-3-yl)-2-(4-phenyl-1,3-thiazol-2-yl)nicotinamide, N-(1-amino-1,2-dioxoheptan-3-yl)-2-(4-phenyl-1,3-thiazol-2-yl)benzamide, N-(4-amino-3,4-dioxo-1-phenylbutan-2-yl)-2-(4-phenyl-1,3-thiazol-2-yl)benzamide, N-(4-(Cyclopropylamino)-3,4-dioxo-1-phenylbutan-2-yl)-2-(4-phenyl-1,3-thiazol-2-yl)nicotinamide, N-(4-(Methoxyamino)-3,4-dioxo-1-phenylbutan-2-yl)-2-(4-phenylthiazol-2-yl)nicotinamide and N-(4-amino-3,4-dioxo-1-phenylbutan-2-yl)-2-(4-phenyloxazol-2-yl)nicotinamide, and the pharmaceutically suitable salts thereof, their prodrugs, their hydrates and the tautomers thereof.

In turn preferred among the carboxamide compounds of the invention of the formula I-B are compounds which correspond to the general formulae I-B.a, I-B.b, I-B.c or I-B.d,

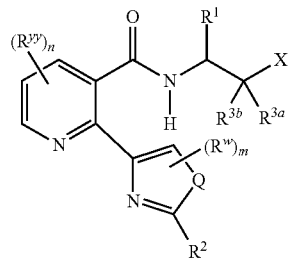

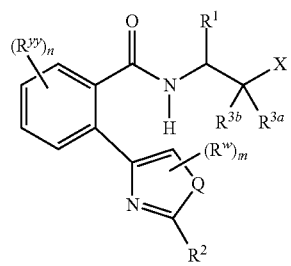

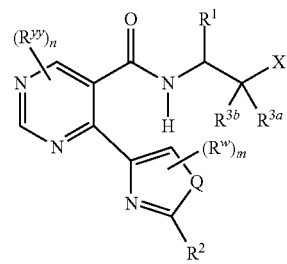

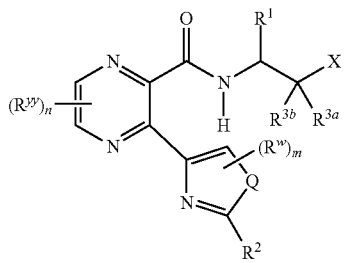

in which n, $R^{yy}$, m, $R^W$, Q, X, $R^1$, $R^2$, $R^{3a}$ and $R^{3b}$ have the aforementioned meanings, in particular those mentioned as preferred.

Particularly preferred are compounds of the formulae I-B.a and I-B.b wherein:
m is 0;
$R^1$ is phenyl-$C_1$-$C_4$-alkyl, which is unsubstituted or carries 1, 2, 3 or 4 identical or different radicals $R^{1c}$,
$R^2$ is phenyl or is naphthyl, where phenyl and naphthyl may be unsubstituted or substituted with 1 or 2 identical or different radicals $R^{2b}$,
X is $CONH_2$ or $CONHR^{x2a}$, wherein $R^{x2a}$ are as defined above, and
$R^{3a}$ and $R^{3b}$ are each OH or the group Gee is a carbonyl group.

Particularly preferred are compounds of the formulae I-B.a and I-B.b wherein:
m is 0;
$R^1$ is $C_3$-$C_8$-alkyl,
$R^2$ is phenyl or is naphthyl, where phenyl and naphthyl may be unsubstituted or substituted with 1 or 2 identical or different radicals $R^{2b}$,
X is $CONH_2$ or $CONHR^{x2a}$, wherein $R^{x2a}$ are as defined above, and
$R^{3a}$ and $R^{3b}$ are each OH or the group $CR^{3a}R^{3b}$ is a carbonyl group.

Preferred examples of compounds of formula I-B.a and I-B.b comprise
N-(4-amino-3,4-dioxo-1-phenylbutan-2-yl)-2-[2-(4-fluorophenyl)-1,3-thiazol-4-yl]pyridine-3-carboxamide,
N-(4-amino-3,4-dioxo-1-phenylbutan-2-yl)-2-{2-[3-(trifluoromethyl)phenyl]-1,3-thiazol-4-yl}pyridine-3-carboxamide,
N-(4-amino-3,4-dioxo-1-phenylbutan-2-yl)-2-(2-phenyl-1,3-thiazol-4-yl)pyridine-3-carboxamide,
N-(4-amino-3,4-dioxo-1-phenylbutan-2-yl)-2-[2-(2-chlorophenyl)-1,3-thiazol-4-yl]pyridine-3-carboxamide,
N-(4-amino-3,4-dioxo-1-phenylbutan-2-yl)-2-[2-(naphthalen-2-yl)-1,3-thiazol-4-yl]pyridine-3-carboxamide,
N-(1-amino-1,2-dioxoheptan-3-yl)-2-(2-phenylthiazol-4-yl)nicotinamide,
N-(1-amino-1,2-dioxoheptan-3-yl)-2-(2-phenyl-1,3-thiazol-4-yl)benzamide,
N-(4-amino-3,4-dioxo-1-phenylbutan-2-yl)-2-(2-phenyl-1,3-thiazol-4-yl)benzamide,
N-(4-(Cyclopropylamino)-3,4-dioxo-1-phenylbutan-2-yl)-2-(2-phenylthiazol-4-yl)nicotinamide,
N-(4-(Methoxyamino)-3,4-dioxo-1-phenylbutan-2-yl)-2-(2-phenylthiazol-4-yl)nicotinamide and
N-(4-amino-3,4-dioxo-1-phenylbutan-2-yl)-2-(2-phenyloxazol-4-yl)nicotinamide and the pharmaceutically suitable salts, their prodrugs, their hydrates and the tautomers thereof.

In turn preferred among the carboxamide compounds of the invention of the formula I-C are compounds which correspond to the general formulae I-C.a, I-C.b, I-C.c or I-C.d,

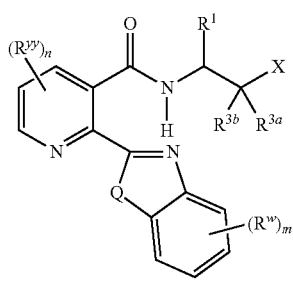
(I-C.a)

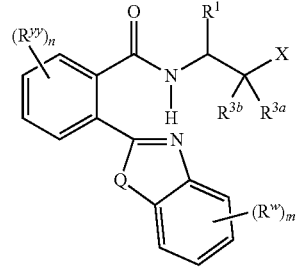
(I-C.b)

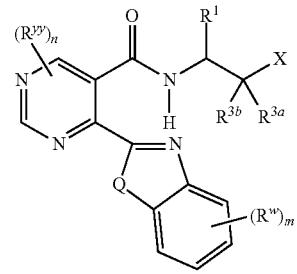
(I-C.c)

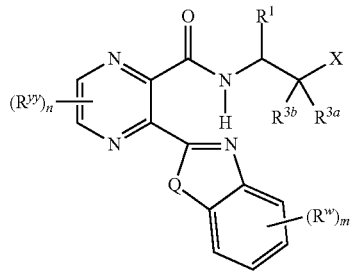
(I-C.d)

in which n, $R^{yy}$, m, $R^W$, Q, X, $R^1$, $R^{3a}$ and $R^{ab}$ have the aforementioned meanings, in particular those mentioned as preferred.

Particularly preferred are compounds of the formulae I-C.a and I-C.b wherein:
m is 0;
$R^1$ is phenyl-$C_1$-$C_4$-alkyl, which is unsubstituted or carries 1, 2, 3 or 4 identical or different radicals $R^{1c}$,
$R^2$ is phenyl or is naphthyl, where phenyl and naphthyl may be unsubstituted or substituted with 1 or 2 identical or different radicals $R^{2b}$,
X is $CONH_2$ or $CONHR^{x2a}$, wherein $R^{x2a}$ are as defined above, and
$R^{3a}$ and $R^{3b}$ are each OH or the group $CR^{3a}R^{3b}$ is a carbonyl group.

Particularly preferred are compounds of the formulae I-C.a and I-C.b wherein:
m is 0;
$R^1$ is $C_3$-$C_8$-alkyl,
$R^2$ is phenyl or is naphthyl, where phenyl and naphthyl may be unsubstituted or substituted with 1 or 2 identical or different radicals $R^{2b}$,
X is $CONH_2$ or $CONHR^{x2a}$, wherein $R^{x2a}$ are as defined above, and
$R^{3a}$ and $R^{3b}$ are each OH or the group Gee is a carbonyl group.

Preferred examples of compounds of formula I-C.a comprise:
N-(4-amino-3,4-dioxo-1-phenylbutan-2-yl)-2-(1H-benzimidazol-2-yl)pyridine-3-carboxamide;
N-(4-amino-3,4-dioxo-1-phenylbutan-2-yl)-2-(1,3-benzothiazol-2-yl)pyridine-3-carboxamide; and N-(4-amino-3,4-dioxo-1-phenylbutan-2-yl)-2-(1,3-benzo[d]oxazol-2-yl)pyridine-3-carboxamide and the pharmaceutically suitable salts thereof, their prodrugs, their hydrates and the tautomers thereof.

The compounds of the general formulae I-a, I-b, I-c and I-d, which are indicated in Tables 1 to 160 below and in which Gee is a carbonyl function or a C(OH)$_2$ group, and their tautomers, prodrugs and pharmaceutically acceptable salts, represent per se preferred embodiments of the present invention. The meanings for $R^1$ and $R^2$ indicated in Table A below, as well as the meanings for $R^1$ and W3 (represented by W—$R^2$) indicated in Table B below, represent embodiments of the invention which are likewise preferred independently of one another and especially in combination.

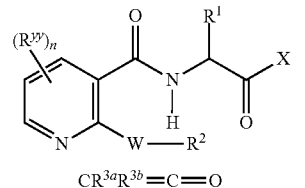

(I-a)

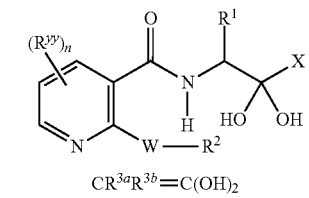

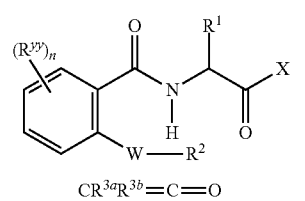

(I-b)

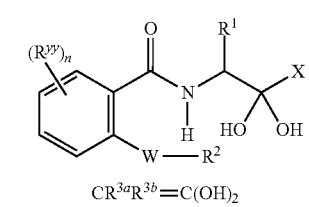

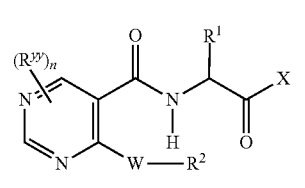

(I-c)

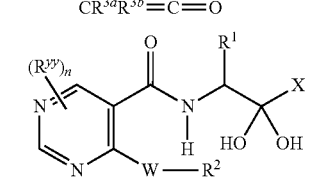

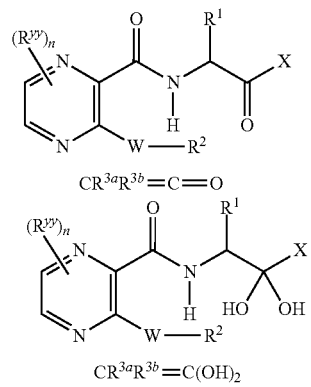

In subsequent Tables 1 to 80 the variables W1a, W1b, W2a and W2b have the following meanings:

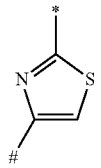

(W1a)

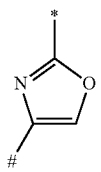

(W1b)

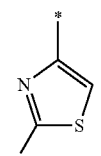

(W2a)

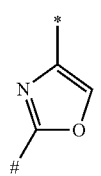

(W2b)

in which * and # have the have the aforementioned meanings.

Table 1

Compounds of the formulae I-a, I-b, I-c and I-d in which the group C($R^{3a}R^{3b}$) is C=O, X is carbamoyl, n=0, i.e. ($R^{yy}$)$_n$ is absent, W is W1a, and the combination of $R^1$ and $R^2$ for a compound in each case corresponds to one line of Table A.

Table 2

Compounds of the formulae I-a, I-b and I-d in which the group C($R^{3a}R^{3b}$) is C=O, X is carbamoyl, ($R^{yy}$)$_n$ is 5-F, W is W1a, and the combination of $R^1$ and $R^2$ for a compound in each case corresponds to one line of Table A.

Table 3

Compounds of the formulae I-a, I-b and I-d in which the group C($R^{3a}R^{3b}$) is C=O, X is carbamoyl, ($R^{yy}$)$_n$ is 5-Cl, W is W1a, and the combination of $R^1$ and $R^2$ for a compound in each case corresponds to one line of Table A.

Table 4
Compounds of the formulae I-a, I-b and I-d in which the group $C(R^{3a}R^{3b})$ is C=O, X is carbamoyl, $(R^{yy})_n$ is 5-CN, W is W1a, and the combination of $R^1$ and $R^2$ for a compound in each case corresponds to one line of Table A.

Table 5
Compounds of the formulae I-a, I-b and I-d in which the group $C(R^{3a}R^{3b})$ is C=O, X is carbamoyl, $(R^{yy})_n$ is 5-CH$_3$, W is W1a, and the combination of $R^1$ and $R^2$ for a compound in each case corresponds to one line of Table A.

Table 6
Compounds of the formulae I-a, I-b, I-c and I-d in which the group $C(R^{3a}R^{3b})$ is C=O, X is —C(O)NHCH$_3$, n=0, i.e. $(R^{yy})_n$ is absent, W is W1a, and the combination of $R^1$ and $R^2$ for a compound in each case corresponds to one line of Table A.

Table 7
Compounds of the formulae I-a, I-b and I-d in which the group $C(R^{3a}R^{3b})$ is C=O, X is —C(O)NHCH$_3$, $(R^{yy})_n$ is 5-F, W is W1a, and the combination of $R^1$ and $R^2$ for a compound in each case corresponds to one line of Table A.

Table 8
Compounds of the formulae I-a, I-b and I-d in which the group $C(R^{3a}R^{3b})$ is C=O, X is —C(O)NHCH$_3$, $(R^{yy})_n$ is 5-Cl, W is W1a, and the combination of $R^1$ and $R^2$ for a compound in each case corresponds to one line of Table A.

Table 9
Compounds of the formulae I-a, I-b and I-d in which the group $C(R^{3a}R^{3b})$ is C=O, X is —C(O)NHCH$_3$, $(R^{yy})_n$ is 5-CN, W is W1a, and the combination of $R^1$ and $R^2$ for a compound in each case corresponds to one line of Table A.

Table 10
Compounds of the formulae I-a, I-b and I-d in which the group $C(R^{3a}R^{3b})$ is C=O, X is —C(O)NHCH$_3$, $(R^{yy})_n$ is 5-CH$_3$, W is W1a, and the combination of $R^1$ and $R^2$ for a compound in each case corresponds to one line of Table A.

Table 11
Compounds of the formulae I-a, I-b, I-c and I-d in which the group $C(R^{3a}R^{3b})$ is C(OH)$_2$, X is carbamoyl, n=0, i.e. $(R^{yy})_n$ is absent, W is W1a, and the combination of $R^1$ and $R^2$ for a compound in each case corresponds to one line of Table A.

Table 12
Compounds of the formulae I-a, I-b and I-d in which the group $C(R^{3a}R^{3b})$ is C(OH)$_2$, X is carbamoyl, $(R^{yy})_n$ is 5-F, W is W1a, and the combination of $R^1$ and $R^2$ for a compound in each case corresponds to one line of Table A.

Table 13
Compounds of the formulae I-a, I-b and I-d in which the group $C(R^{3a}R^{3b})$ is C(OH)$_2$, X is carbamoyl, $(R^{yy})_n$ is 5-Cl, W is W1a, and the combination of $R^1$ and $R^2$ for a compound in each case corresponds to one line of Table A.

Table 14
Compounds of the formulae I-a, I-b and I-d in which the group $C(R^{3a}R^{3b})$ is C(OH)$_2$, X is carbamoyl, $(R^{yy})_n$ is 5-CN, W is W1a, and the combination of $R^1$ and $R^2$ for a compound in each case corresponds to one line of Table A.

Table 15
Compounds of the formulae I-a, I-b and I-d in which the group $C(R^{3a}R^{3b})$ is C(OH)$_2$, X is carbamoyl, $(R^{yy})_n$ is 5-CH$_3$, W is W1a, and the combination of $R^1$ and $R^2$ for a compound in each case corresponds to one line of Table A.

Table 16
Compounds of the formulae I-a, I-b, I-c and I-d in which the group $C(R^{3a}R^{3b})$ is C(OH)$_2$, X is —C(O)NHCH$_3$, n=0, i.e. $(R^{yy})_n$ is absent, W is W1a, and the combination of $R^1$ and $R^2$ for a compound in each case corresponds to one line of Table A.

Table 17
Compounds of the formulae I-a, I-b, I-c and I-d in which the group $C(R^{3a}R^{3b})$ is C(OH)$_2$, X is —C(O)NHCH$_3$, $(R^{yy})_n$ is 5-F, W is W1a, and the combination of $R^1$ and $R^2$ for a compound in each case corresponds to one line of Table A.

Table 18
Compounds of the formulae I-a, I-b and I-d in which the group $C(R^{3a}R^{3b})$ is C(OH)$_2$, X is —C(O)NHCH$_3$, $(R^{yy})_n$ is 5-Cl, W is W1a, and the combination of $R^1$ and $R^2$ for a compound in each case corresponds to one line of Table A.

Table 19
Compounds of the formulae I-a, I-b and I-d in which the group $C(R^{3a}R^{3b})$ is C(OH)$_2$, X is —C(O)NHCH$_3$, $(R^{yy})_n$ is 5-CN, W is W1a, and the combination of $R^1$ and $R^2$ for a compound in each case corresponds to one line of Table A.

Table 20
Compounds of the formulae I-a, I-b and I-d in which the group $C(R^{3a}R^{3b})$ is C(OH)$_2$, X is —C(O)NHCH$_3$, $(R^{yy})_n$ is 5-CH$_3$, W is W1a, and the combination of $R^1$ and $R^2$ for a compound in each case corresponds to one line of Table A.

Table 21
Compounds of the formulae I-a, I-b, I-c and I-d in which the group $C(R^{3a}R^{3b})$ is C=O, X is carbamoyl, n=0, i.e. $(R^{yy})_n$ is absent, W is W1b, and the combination of $R^1$ and $R^2$ for a compound in each case corresponds to one line of Table A.

Table 22
Compounds of the formulae I-a, I-b and I-d in which the group $C(R^{3a}R^{3b})$ is C=O, X is carbamoyl, $(R^{yy})_n$ is 5-F, W is W1b, and the combination of $R^1$ and $R^2$ for a compound in each case corresponds to one line of Table A.

Table 23
Compounds of the formulae I-a, I-b and I-d in which the group $C(R^{3a}R^{3b})$ is C=O, X is carbamoyl, $(R^{yy})_n$ is 5-Cl, W is W1b, and the combination of $R^1$ and $R^2$ for a compound in each case corresponds to one line of Table A.

Table 24
Compounds of the formulae I-a, I-b and I-d in which the group $C(R^{3a}R^{3b})$ is C=O, X is carbamoyl, $(R^{yy})_n$ is 5-CN, W is W1b, and the combination of $R^1$ and $R^2$ for a compound in each case corresponds to one line of Table A.

Table 25
Compounds of the formulae I-a, I-b and I-d in which the group $C(R^{3a}R^{3b})$ is C=O, X is carbamoyl, $(R^{yy})_n$ is 5-CH$_3$, W is W1b, and the combination of $R^1$ and $R^2$ for a compound in each case corresponds to one line of Table A.

Table 26
Compounds of the formulae I-a, I-b, I-c and I-d in which the group $C(R^{3a}R^{3b})$ is C=O, X is —C(O)NHCH$_3$, n=0, i.e. $(R^{yy})_n$ is absent, W is W1b, and the combination of $R^1$ and $R^2$ for a compound in each case corresponds to one line of Table A.

Table 27
Compounds of the formulae I-a, I-b and I-d in which the group $C(R^{3a}R^{3b})$ is C=O, X is —C(O)NHCH$_3$, $(R^{yy})_n$ is 5-F, W is W1b, and the combination of $R^1$ and $R^2$ for a compound in each case corresponds to one line of Table A.

Table 28
Compounds of the formulae I-a, I-b and I-d in which the group $C(R^{3a}R^{3b})$ is C=O, X is —C(O)NHCH$_3$, $(R^{yy})_n$ is 5-Cl, W is W1b, and the combination of $R^1$ and $R^2$ for a compound in each case corresponds to one line of Table A.

Table 29
Compounds of the formulae I-a, I-b and I-d in which the group $C(R^{3a}R^{3b})$ is C=O, X is —C(O)NHCH$_3$, $(R^{yy})_n$ is 5-CN, W is W1b, and the combination of $R^1$ and $R^2$ for a compound in each case corresponds to one line of Table A.

Table 30

Compounds of the formulae I-a, I-b and I-d in which the group $C(R^{3a}R^{3b})$ is C=O, X is —C(O)NHCH$_3$, $(R^{yy})_n$ 5-CH$_3$, W is W1b, and the combination of $R^1$ and $R^2$ for a compound in each case corresponds to one line of Table A.

Table 31

Compounds of the formulae I-a, I-b, I-c and I-d in which the group $C(R^{3a}R^{3b})$ is $C(OH)_2$, X is carbamoyl, n=0, i.e. $(R^y)_n$ is absent, W is W1b, and the combination of $R^1$ and $R^2$ for a compound in each case corresponds to one line of Table A.

Table 32

Compounds of the formulae I-a, I-b and I-d in which the group $C(R^{3a}R^{3b})$ is $C(OH)_2$, X is carbamoyl, $(R^{yy})_n$ is 5-F, W is W1b, and the combination of $R^1$ and $R^2$ for a compound in each case corresponds to one line of Table A.

Table 33

Compounds of the formulae I-a, I-b and I-d in which the group $C(R^{3a}R^{3b})$ is $C(OH)_2$, X is carbamoyl, $(R^{yy})_n$ is 5-Cl, W is W1b, and the combination of $R^1$ and $R^2$ for a compound in each case corresponds to one line of Table A.

Table 34

Compounds of the formulae I-a, I-b and I-d in which the group $C(R^{3a}R^{3b})$ is $C(OH)_2$, X is carbamoyl, $(R^{yy})_n$ is 5-CN, W is W1b, and the combination of $R^1$ and $R^2$ for a compound in each case corresponds to one line of Table A.

Table 35

Compounds of the formulae I-a, I-b and I-d in which the group $C(R^{3a}R^{3b})$ is $C(OH)_2$, X is carbamoyl, $(R^{yy})_n$ is 5-CH$_3$, W is W1b, and the combination of $R^1$ and $R^2$ for a compound in each case corresponds to one line of Table A.

Table 36

Compounds of the formulae I-a, I-b, I-c and I-d in which the group $C(R^{3a}R^{3b})$ is $C(OH)_2$, X is —C(O)NHCH$_3$, n=0, i.e. $(R^{yy})_n$ is absent, W is W1b, and the combination of $R^1$ and $R^2$ for a compound in each case corresponds to one line of Table A.

Table 37

Compounds of the formulae I-a, I-b, I-c and I-d in which the group $C(R^{3a}R^{3b})$ is $C(OH)_2$, X is —C(O)NHCH$_3$, $(R^y)_n$ is 5-F, W is W1b, and the combination of $R^1$ and $R^2$ for a compound in each case corresponds to one line of Table A.

Table 38

Compounds of the formulae I-a, I-b and I-d in which the group $C(R^{3a}R^{3b})$ is $C(OH)_2$, X is —C(O)NHCH$_3$, $(R^{yy})_n$ is 5-Cl, W is W1b, and the combination of $R^1$ and $R^2$ for a compound in each case corresponds to one line of Table A.

Table 39

Compounds of the formulae I-a, I-b and I-d in which the group $C(R^{3a}R^{3b})$ is $C(OH)_2$, X is —C(O)NHCH$_3$, $(R^{yy})_n$ is 5-CN, W is W1b, and the combination of $R^1$ and $R^2$ for a compound in each case corresponds to one line of Table A.

Table 40

Compounds of the formulae I-a, I-b and I-d in which the group $C(R^{3a}R^{3b})$ is $C(OH)_2$, X is —C(O)NHCH$_3$, $(R^{yy})_n$ is 5-CH$_3$, W is W1b, and the combination of $R^1$ and $R^2$ for a compound in each case corresponds to one line of Table A.

Table 41

Compounds of the formulae I-a, I-b, I-c and I-d in which the group $C(R^{3a}R^{3b})$ is C=O, X is carbamoyl, n=0, i.e. $(R^{yy})_n$ is absent, W is W2a, and the combination of $R^1$ and $R^2$ for a compound in each case corresponds to one line of Table A.

Table 42

Compounds of the formulae I-a, I-b and I-d in which the group $C(R^{3a}R^{3b})$ is C=O, X is carbamoyl, $(R^{yy})_n$ is 5-F, W is W2a, and the combination of $R^1$ and $R^2$ for a compound in each case corresponds to one line of Table A.

Table 43

Compounds of the formulae I-a, I-b and I-d in which the group $C(R^{3a}R^{3b})$ is C=O, X is carbamoyl, $(R^{yy})_n$ is 5-Cl, W is W2a, and the combination of $R^1$ and $R^2$ for a compound in each case corresponds to one line of Table A.

Table 44

Compounds of the formulae I-a, I-b and I-d in which the group $C(R^{3a}R^{3b})$ is C=O, X is carbamoyl, $(R^{yy})_n$ is 5-CN, W is W2a, and the combination of $R^1$ and $R^2$ for a compound in each case corresponds to one line of Table A.

Table 45

Compounds of the formulae I-a, I-b and I-d in which the group $C(R^{3a}R^{3b})$ is C=O, X is carbamoyl, $(R^{yy})_n$ is 5-CH$_3$, W is W2a, and the combination of $R^1$ and $R^2$ for a compound in each case corresponds to one line of Table A.

Table 46

Compounds of the formulae I-a, I-b, I-c and I-d in which the group $C(R^{3a}R^{3b})$ is C=O, X is —C(O)NHCH$_3$, n=0, i.e. $(R^{yy})_n$ is absent, W is W2a, and the combination of $R^1$ and $R^2$ for a compound in each case corresponds to one line of Table A.

Table 47

Compounds of the formulae I-a, I-b and I-d in which the group $C(R^{3a}R^{3b})$ is C=O, X is —C(O)NHCH$_3$, $(R^{yy})_n$ is 5-F, W is W2a, and the combination of $R^1$ and $R^2$ for a compound in each case corresponds to one line of Table A.

Table 48

Compounds of the formulae I-a, I-b and I-d in which the group $C(R^{3a}R^{3b})$ is C=O, X is —C(O)NHCH$_3$, $(R^{yy})_n$ is 5-Cl, W is W2a, and the combination of $R^1$ and $R^2$ for a compound in each case corresponds to one line of Table A.

Table 49

Compounds of the formulae I-a, I-b and I-d in which the group $C(R^{3a}R^{3b})$ is C=O, X is —C(O)NHCH$_3$, $(R^{yy})_n$ is 5-CN, W is W2a, and the combination of $R^1$ and $R^2$ for a compound in each case corresponds to one line of Table A.

Table 50

Compounds of the formulae I-a, I-b and I-d in which the group $C(R^{3a}R^{3b})$ is C=O, X is —C(O)NHCH$_3$, $(R^{yy})_n$ is 5-CH$_3$, W is W2a, and the combination of $R^1$ and $R^2$ for a compound in each case corresponds to one line of Table A.

Table 51

Compounds of the formulae I-a, I-b, I-c and I-d in which the group $C(R^{3a}R^{3b})$ is $C(OH)_2$, X is carbamoyl, n=0, i.e. $(R^{yy})_n$ is absent, W is W2a, and the combination of $R^1$ and $R^2$ for a compound in each case corresponds to one line of Table A.

Table 52

Compounds of the formulae I-a, I-b and I-d in which the group $C(R^{3a}R^{3b})$ is $C(OH)_2$, X is carbamoyl, $(R^{yy})_n$ is 5-F, W is W2a, and the combination of $R^1$ and $R^2$ for a compound in each case corresponds to one line of Table A.

Table 53

Compounds of the formulae I-a, I-b and I-d in which the group $C(R^{3a}R^{3b})$ is $C(OH)_2$, X is carbamoyl, $(R^{yy})_n$ is 5-Cl, W is W2a, and the combination of $R^1$ and $R^2$ for a compound in each case corresponds to one line of Table A.

Table 54

Compounds of the formulae I-a, I-b and I-d in which the group $C(R^{3a}R^{3b})$ is $C(OH)_2$, X is carbamoyl, $(R^{yy})_n$ is 5-CN, W is W2a, and the combination of $R^1$ and $R^2$ for a compound in each case corresponds to one line of Table A.

Table 55

Compounds of the formulae I-a, I-b and I-d in which the group $C(R^{3a}R^{3b})$ is $C(OH)_2$, X is carbamoyl, $(R^{yy})_n$ is 5-CH$_3$, W is W2a, and the combination of $R^1$ and $R^2$ for a compound in each case corresponds to one line of Table A.

Table 56

Compounds of the formulae I-a, I-b, I-c and I-d in which the group $C(R^{3a}R^{3b})$ is $C(OH)_2$, X is —C(O)NHCH$_3$, n=0, i.e. $(R^{yy})_n$ is absent, W is W2a, and the combination of $R^1$ and $R^2$ for a compound in each case corresponds to one line of Table A.

Table 57

Compounds of the formulae I-a, I-b, I-c and I-d in which the group $C(R^{3a}R^{3b})$ is $C(OH)_2$, X is —C(O)NHCH$_3$, $(R^{yy})_n$ is 5-F, W is W2a, and the combination of $R^1$ and $R^2$ for a compound in each case corresponds to one line of Table A.

Table 58

Compounds of the formulae I-a, I-b and I-d in which the group $C(R^{3a}R^{3b})$ is $C(OH)_2$, X is —C(O)NHCH$_3$, $(R^{yy})_n$ is 5-Cl, W is W2a, and the combination of $R^1$ and $R^2$ for a compound in each case corresponds to one line of Table A.

Table 59

Compounds of the formulae I-a, I-b and I-d in which the group $C(R^{3a}R^{3b})$ is $C(OH)_2$, X is —C(O)NHCH$_3$, $(R^{yy})_n$ is 5-CN, W is W2a, and the combination of $R^1$ and $R^2$ for a compound in each case corresponds to one line of Table A.

Table 60

Compounds of the formulae I-a, I-b and I-d in which the group $C(R^{3a}R^{3b})$ is $C(OH)_2$, X is —C(O)NHCH$_3$, $(R^{yy})_n$ is 5-CH$_3$, W is W2a, and the combination of $R^1$ and $R^2$ for a compound in each case corresponds to one line of Table A.

Table 61

Compounds of the formulae I-a, I-b, I-c and I-d in which the group $C(R^{3a}R^{3b})$ is C=O, X is carbamoyl, n=0, i.e. $(R^{yy})_n$ is absent, W is W2b, and the combination of $R^1$ and $R^2$ for a compound in each case corresponds to one line of Table A.

Table 62

Compounds of the formulae I-a, I-b and I-d in which the group $C(R^{3a}R^{3b})$ is C=O, X is carbamoyl, $(R^{yy})_n$ is 5-F, W is W2b, and the combination of $R^1$ and $R^2$ for a compound in each case corresponds to one line of Table A.

Table 63

Compounds of the formulae I-a, I-b and I-d in which the group $C(R^{3a}R^{3b})$ is C=O, X is carbamoyl, $(R^{yy})_n$ is 5-Cl, W is W2b, and the combination of $R^1$ and $R^2$ for a compound in each case corresponds to one line of Table A.

Table 64

Compounds of the formulae I-a, I-b and I-d in which the group $C(R^{3a}R^{3b})$ is C=O, X is carbamoyl, $(R^{yy})_n$ is 5-CN, W is W2b, and the combination of $R^1$ and $R^2$ for a compound in each case corresponds to one line of Table A.

Table 65

Compounds of the formulae I-a, I-b and I-d in which the group $C(R^{3a}R^{3b})$ is C=O, X is carbamoyl, $(R^{yy})_n$ is 5-CH$_3$, W is W2b, and the combination of $R^1$ and $R^2$ for a compound in each case corresponds to one line of Table A.

Table 66

Compounds of the formulae I-a, I-b, I-c and I-d in which the group $C(R^{3a}R^{3b})$ is C=O, X is —C(O)NHCH$_3$, n=0, i.e. $(R^{yy})_n$ is absent, W is W2b, and the combination of $R^1$ and $R^2$ for a compound in each case corresponds to one line of Table A.

Table 67

Compounds of the formulae I-a, I-b and I-d in which the group $C(R^{3a}R^{3b})$ is C=O, X is —C(O)NHCH$_3$, $(R^{yy})_n$ is 5-F, W is W2b, and the combination of $R^1$ and $R^2$ for a compound in each case corresponds to one line of Table A.

Table 68

Compounds of the formulae I-a, I-b and I-d in which the group $C(R^{3a}R^{3b})$ is C=O, X is —C(O)NHCH$_3$, $(R^{yy})_n$ is 5-Cl, W is W2b, and the combination of $R^1$ and $R^2$ for a compound in each case corresponds to one line of Table A.

Table 69

Compounds of the formulae I-a, I-b and I-d in which the group $C(R^{3a}R^{3b})$ is C=O, X is —C(O)NHCH$_3$, $(R^{yy})_n$ is 5-CN, W is W2b, and the combination of $R^1$ and $R^2$ for a compound in each case corresponds to one line of Table A.

Table 70

Compounds of the formulae I-a, I-b and I-d in which the group $C(R^{3a}R^{3b})$ is C=O, X is —C(O)NHCH$_3$, $(R^{yy})_n$ is 5-CH$_3$, W is W2b, and the combination of $R^1$ and $R^2$ for a compound in each case corresponds to one line of Table A.

Table 71

Compounds of the formulae I-a, I-b, I-c and I-d in which the group $C(R^{3a}R^{3b})$ is $C(OH)_2$, X is carbamoyl, n=0, i.e. $(R^{yy})_n$ is absent, W is W2b, and the combination of $R^1$ and $R^2$ for a compound in each case corresponds to one line of Table A.

Table 72

Compounds of the formulae I-a, I-b and I-d in which the group $C(R^{3a}R^{3b})$ is $C(OH)_2$, X is carbamoyl, $(R^{yy})_n$ is 5-F, W is W2b, and the combination of $R^1$ and $R^2$ for a compound in each case corresponds to one line of Table A.

Table 73

Compounds of the formulae I-a, I-b and I-d in which the group $C(R^{3a}R^{3b})$ is $C(OH)_2$, X is carbamoyl, $(R^{yy})_n$ is 5-Cl, W is W2b, and the combination of $R^1$ and $R^2$ for a compound in each case corresponds to one line of Table A.

Table 74

Compounds of the formulae I-a, I-b and I-d in which the group $C(R^{3a}R^{3b})$ is $C(OH)_2$, X is carbamoyl, $(R^{yy})_n$ is 5-CN, W is W2b, and the combination of $R^1$ and $R^2$ for a compound in each case corresponds to one line of Table A.

Table 75

Compounds of the formulae I-a, I-b and I-d in which the group $C(R^{3a}R^{3b})$ is $C(OH)_2$, X is carbamoyl, $(R^{yy})_n$ is 5-CH$_3$, W is W2b, and the combination of $R^1$ and $R^2$ for a compound in each case corresponds to one line of Table A.

Table 76

Compounds of the formulae I-a, I-b, I-c and I-d in which the group $C(R^{3a}R^{3b})$ is $C(OH)_2$, X is —C(O)NHCH$_3$, n=0, i.e. $(R^{yy})_n$ is absent, W is W2b, and the combination of $R^1$ and $R^2$ for a compound in each case corresponds to one line of Table A.

Table 77

Compounds of the formulae I-a, I-b, I-c and I-d in which the group $C(R^{3a}R^{3b})$ is $C(OH)_2$, X is —C(O)NHCH$_3$, $(R^{yy})_n$ is 5-F, W is W1b, and the combination of $R^1$ and $R^2$ for a compound in each case corresponds to one line of Table A.

Table 78

Compounds of the formulae I-a, I-b and I-d in which the group $C(R^{3a}R^{3b})$ is $C(OH)_2$, X is —C(O)NHCH$_3$, $(R^{yy})_n$ is 5-Cl, W is W2b, and the combination of $R^1$ and $R^2$ for a compound in each case corresponds to one line of Table A.

Table 79

Compounds of the formulae I-a, I-b and I-d in which the group $C(R^{3a}R^{3b})$ is $C(OH)_2$, X is —C(O)NHCH$_3$, $(R^{yy})_n$ is 5-CN, W is W2b, and the combination of $R^1$ and $R^2$ for a compound in each case corresponds to one line of Table A.

Table 80

Compounds of the formulae I-a, I-b and I-d in which the group $C(R^{3a}R^{3b})$ is $C(OH)_2$, X is —C(O)NHCH$_3$, $(R^{yy})_n$ is 5-CH$_3$, W is W2b, and the combination of $R^1$ and $R^2$ for a compound in each case corresponds to one line of Table A.

Table 81

Compounds of the formulae I-a, I-b, I-c and I-d in which the group $C(R^{3a}R^{3b})$ is C=O, X is —C(O)NHOCH$_3$, n=0, i.e. $(R^{yy})_n$ is absent, W is W1a, and the combination of $R^1$ and $R^2$ for a compound in each case corresponds to one line of Table A.

Table 82
Compounds of the formulae I-a, I-b and I-d in which the group $C(R^{3a}R^{3b})$ is C=O, X is —C(O)NHOCH$_3$, $(R^{yy})_n$ is 5-F, W is W1a, and the combination of $R^1$ and $R^2$ for a compound in each case corresponds to one line of Table A.

Table 83
Compounds of the formulae I-a, I-b and I-d in which the group $C(R^{3a}R^{3b})$ is C=O, X is —C(O)NHOCH$_3$, $(R^{yy})_n$ is 5-Cl, W is W1a, and the combination of $R^1$ and $R^2$ for a compound in each case corresponds to one line of Table A.

Table 84
Compounds of the formulae I-a, I-b and I-d in which the group $C(R^{3a}R^{3b})$ is C=O, X is —C(O)NHOCH$_3$, $(R^{yy})_n$ is 5-CN, W is W1a, and the combination of $R^1$ and $R^2$ for a compound in each case corresponds to one line of Table A.

Table 85
Compounds of the formulae I-a, I-b and I-d in which the group $C(R^{3a}R^{3b})$ is C=O, X is —C(O)NHOCH$_3$, $(R^{yy})_n$ is 5-CH$_3$, W is W1a, and the combination of $R^1$ and $R^2$ for a compound in each case corresponds to one line of Table A.

Table 86
Compounds of the formulae I-a, I-b, I-c and I-d in which the group $C(R^{3a}R^{3b})$ is C(OH)$_2$, X is —C(O)NHOCH$_3$, n=0, i.e. $(R^{yy})_n$ is absent, W is W1a, and the combination of $R^1$ and $R^2$ for a compound in each case corresponds to one line of Table A.

Table 87
Compounds of the formulae I-a, I-b, I-c and I-d in which the group $C(R^{3a}R^{3b})$ is C(OH)$_2$, X is —C(O)NHOCH$_3$, $(R^{yy})_n$ is 5-F, W is W1a, and the combination of $R^1$ and $R^2$ for a compound in each case corresponds to one line of Table A.

Table 88
Compounds of the formulae I-a, I-b and I-d in which the group $C(R^{3a}R^{3b})$ is C(OH)$_2$, X is —C(O)NHOCH$_3$, $(R^{yy})_n$ is 5-Cl, W is W1a, and the combination of $R^1$ and $R^2$ for a compound in each case corresponds to one line of Table A.

Table 89
Compounds of the formulae I-a, I-b and I-d in which the group $C(R^{3a}R^{3b})$ is C(OH)$_2$, X is —C(O)NHOCH$_3$, $(R^{yy})_n$ is 5-CN, W is W1a, and the combination of $R^1$ and $R^2$ for a compound in each case corresponds to one line of Table A.

Table 90
Compounds of the formulae I-a, I-b and I-d in which the group $C(R^{3a}R^{3b})$ is C(OH)$_2$, X is —C(O)NHOCH$_3$, $(R^{yy})_n$ is 5-CH$_3$, W is W1a, and the combination of $R^1$ and $R^2$ for a compound in each case corresponds to one line of Table A.

Table 91
Compounds of the formulae I-a, I-b, I-c and I-d in which the group $C(R^{3a}R^{3b})$ is C=O, X is —C(O)NHOCH$_3$, n=0, i.e. $(R^{yy})_n$ is absent, W is W1b, and the combination of $R^1$ and $R^2$ for a compound in each case corresponds to one line of Table A.

Table 92
Compounds of the formulae I-a, I-b and I-d in which the group $C(R^{3a}R^{3b})$ is C=O, X is —C(O)NHOCH$_3$, $(R^{yy})_n$ is 5-F, W is W1b, and the combination of $R^1$ and $R^2$ for a compound in each case corresponds to one line of Table A.

Table 93
Compounds of the formulae I-a, I-b and I-d in which the group $C(R^{3a}R^{3b})$ is C=O, X is —C(O)NHOCH$_3$, $(R^{yy})_n$ is 5-Cl, W is W1b, and the combination of $R^1$ and $R^2$ for a compound in each case corresponds to one line of Table A.

Table 94
Compounds of the formulae I-a, I-b and I-d in which the group $C(R^{3a}R^{3b})$ is C=O, X is —C(O)NHOCH$_3$, $(R^{yy})_n$ is 5-CN, W is W1b, and the combination of $R^1$ and $R^2$ for a compound in each case corresponds to one line of Table A.

Table 95
Compounds of the formulae I-a, I-b and I-d in which the group $C(R^{3a}R^{3b})$ is C=O, X is —C(O)NHOCH$_3$, $(R^{yy})_n$ is 5-CH$_3$, W is W1b, and the combination of $R^1$ and $R^2$ for a compound in each case corresponds to one line of Table A.

Table 96
Compounds of the formulae I-a, I-b, I-c and I-d in which the group $C(R^{3a}R^{3b})$ is C(OH)$_2$, X is —C(O)NHOCH$_3$, n=0, i.e. $(R^{yy})_n$ is absent, W is W1b, and the combination of $R^1$ and $R^2$ for a compound in each case corresponds to one line of Table A.

Table 97
Compounds of the formulae I-a, I-b, I-c and I-d in which the group $C(R^{3a}R^{3b})$ is C(OH)$_2$, X is —C(O)NHOCH$_3$, $(R^{y})_n$ is 5-F, W is W1b, and the combination of $R^1$ and $R^2$ for a compound in each case corresponds to one line of Table A.

Table 98
Compounds of the formulae I-a, I-b and I-d in which the group $C(R^{3a}R^{3b})$ is C(OH)$_2$, X is —C(O)NHOCH$_3$, $(R^{yy})_n$ is 5-Cl, W is W1b, and the combination of $R^1$ and $R^2$ for a compound in each case corresponds to one line of Table A.

Table 99
Compounds of the formulae I-a, I-b and I-d in which the group $C(R^{3a}R^{3b})$ is C(OH)$_2$, X is —C(O)NHOCH$_3$, $(R^{yy})_n$ is 5-CN, W is W1b, and the combination of $R^1$ and $R^2$ for a compound in each case corresponds to one line of Table A.

Table 100
Compounds of the formulae I-a, I-b and I-d in which the group $C(R^{3a}R^{3b})$ is C(OH)$_2$, X is —C(O)NHOCH$_3$, $(R^{yy})_n$ is 5-CH$_3$, W is W1b, and the combination of $R^1$ and $R^2$ for a compound in each case corresponds to one line of Table A.

Table 101
Compounds of the formulae I-a, I-b, I-c and I-d in which the group $C(R^{3a}R^{3b})$ is C=O, X is —C(O)NHOCH$_3$, n=0, i.e. $(R^{yy})_n$ is absent, W is W2a, and the combination of $R^1$ and $R^2$ for a compound in each case corresponds to one line of Table A.

Table 102
Compounds of the formulae I-a, I-b and I-d in which the group $C(R^{3a}R^{3b})$ is C=O, X is —C(O)NHOCH$_3$, $(R^{yy})_n$ is 5-F, W is W2a, and the combination of $R^1$ and $R^2$ for a compound in each case corresponds to one line of Table A.

Table 103
Compounds of the formulae I-a, I-b and I-d in which the group $C(R^{3a}R^{3b})$ is C=O, X is —C(O)NHOCH$_3$, $(R^{yy})_n$ is 5-Cl, W is W2a, and the combination of $R^1$ and $R^2$ for a compound in each case corresponds to one line of Table A.

Table 104
Compounds of the formulae I-a, I-b and I-d in which the group $C(R^{3a}R^{3b})$ is C=O, X is —C(O)NHOCH$_3$, $(R^{yy})_n$ is 5-CN, W is W2a, and the combination of $R^1$ and $R^2$ for a compound in each case corresponds to one line of Table A.

Table 105
Compounds of the formulae I-a, I-b and I-d in which the group $C(R^{3a}R^{3b})$ is C=O, X is —C(O)NHOCH$_3$, $(R^{yy})_n$ is 5-CH$_3$, W is W2a, and the combination of $R^1$ and $R^2$ for a compound in each case corresponds to one line of Table A.

Table 106
Compounds of the formulae I-a, I-b, I-c and I-d in which the group $C(R^{3a}R^{3b})$ is C(OH)$_2$, X is —C(O)NHOCH$_3$, n=0, Table 107
Compounds of the formulae I-a, I-b, I-c and I-d in which the group $C(R^{3a}R^{3b})$ is $C(OH)_2$, X is —C(O)NHOCH$_3$, $(R^{yy})_n$ is 5-F, W is W2a, and the combination of $R^1$ and $R^2$ for a compound in each case corresponds to one line of Table A.

Table 108
Compounds of the formulae I-a, I-b and I-d in which the group $C(R^{3a}R^{3b})$ is $C(OH)_2$, X is —C(O)NHOCH$_3$, $(R^{yy})_n$ is 5-Cl, W is W2a, and the combination of $R^1$ and $R^2$ for a compound in each case corresponds to one line of Table A.

Table 109
Compounds of the formulae I-a, I-b and I-d in which the group $C(R^{3a}R^{3b})$ is $C(OH)_2$, X is —C(O)NHOCH$_3$, $(R^{yy})_n$ is 5-CN, W is W2a, and the combination of $R^1$ and $R^2$ for a compound in each case corresponds to one line of Table A.

Table 110
Compounds of the formulae I-a, I-b and I-d in which the group $C(R^{3a}R^{3b})$ is $C(OH)_2$, X is —C(O)NHOCH$_3$, $(R^{yy})_n$ is 5-CH$_3$, W is W2a, and the combination of $R^1$ and $R^2$ for a compound in each case corresponds to one line of Table A.

Table 111
Compounds of the formulae I-a, I-b, I-c and I-d in which the group $C(R^{3a}R^{3b})$ is C=O, X is —C(O)NHOCH$_3$, n=0, i.e. $(R^{yy})_n$ is absent, W is W2b, and the combination of $R^1$ and $R^2$ for a compound in each case corresponds to one line of Table A.

Table 112
Compounds of the formulae I-a, I-b and I-d in which the group $C(R^{3a}R^{3b})$ is C=O, X is —C(O)NHOCH$_3$, $(R^{yy})_n$ is 5-F, W is W2b, and the combination of $R^1$ and $R^2$ for a compound in each case corresponds to one line of Table A.

Table 113
Compounds of the formulae I-a, I-b and I-d in which the group $C(R^{3a}R^{3b})$ is C=O, X is —C(O)NHOCH$_3$, $(R^{yy})_n$ is 5-Cl, W is W2b, and the combination of $R^1$ and $R^2$ for a compound in each case corresponds to one line of Table A.

Table 114
Compounds of the formulae I-a, I-b and I-d in which the group $C(R^{3a}R^{3b})$ is C=O, X is —C(O)NHOCH$_3$, $(R^{yy})_n$ is 5-CN, W is W2b, and the combination of $R^1$ and $R^2$ for a compound in each case corresponds to one line of Table A.

Table 115
Compounds of the formulae I-a, I-b and I-d in which the group $C(R^{3a}R^{3b})$ is C=O, X is —C(O)NHOCH$_3$, $(R^{yy})_n$ is 5-CH$_3$, W is W2b, and the combination of $R^1$ and $R^2$ for a compound in each case corresponds to one line of Table A.

Table 116
Compounds of the formulae I-a, I-b, I-c and I-d in which the group $C(R^{3a}R^{3b})$ is $C(OH)_2$, X is —C(O)NHOCH$_3$, n=0, i.e. $(R^{yy})_n$ is absent, W is W2b, and the combination of $R^1$ and $R^2$ for a compound in each case corresponds to one line of Table A.

Table 117
Compounds of the formulae I-a, I-b, I-c and I-d in which the group $C(R^{3a}R^{3b})$ is $C(OH)_2$, X is —C(O)NHOCH$_3$, $(R^{yy})_n$ is 5-F, W is W1b, and the combination of $R^1$ and $R^2$ for a compound in each case corresponds to one line of Table A.

Table 118
Compounds of the formulae I-a, I-b and I-d in which the group $C(R^{3a}R^{3b})$ is $C(OH)_2$, X is —C(O)NHOCH$_3$, $(R^{yy})_n$ is 5-Cl, W is W2b, and the combination of $R^1$ and $R^2$ for a compound in each case corresponds to one line of Table A.

Table 119
Compounds of the formulae I-a, I-b and I-d in which the group $C(R^{3a}R^{3b})$ is $C(OH)_2$, X is —C(O)NHOCH$_3$, $(R^{yy})_n$ is 5-CN, W is W2b, and the combination of $R^1$ and $R^2$ for a compound in each case corresponds to one line of Table A.

Table 120
Compounds of the formulae I-a, I-b and I-d in which the group $C(R^{3a}R^{3b})$ is $C(OH)_2$, X is —C(O)NHOCH$_3$, $(R^{yy})_n$ is 5-CH$_3$, W is W2b, and the combination of $R^1$ and $R^2$ for a compound in each case corresponds to one line of Table A.

Table 121
Compounds of the formulae I-a, I-b, I-c and I-d in which the group $C(R^{3a}R^{3b})$ is C=O, X is —C(O)NH-c-C$_3$H$_5$, n=0, i.e. $(R^{yy})_n$ is absent, W is W1a, and the combination of $R^1$ and $R^2$ for a compound in each case corresponds to one line of Table A (here and below -c-C$_3$H$_5$ is cyclopropyl).

Table 122
Compounds of the formulae I-a, I-b and I-d in which the group $C(R^{3a}R^{3b})$ is C=O, X is —C(O)NH-c-C$_3$H$_5$, $(R^{yy})_n$ is 5-F, W is W1a, and the combination of $R^1$ and $R^2$ for a compound in each case corresponds to one line of Table A.

Table 123
Compounds of the formulae I-a, I-b and I-d in which the group $C(R^{3a}R^{3b})$ is C=O, X is —C(O)NH-c-C$_3$H$_5$, $(R^{yy})_n$ is 5-Cl, W is W1a, and the combination of $R^1$ and $R^2$ for a compound in each case corresponds to one line of Table A.

Table 124
Compounds of the formulae I-a, I-b and I-d in which the group $C(R^{3a}R^{3b})$ is C=O, X is —C(O)NH-c-C$_3$H$_5$, $(R^{yy})_n$ is 5-CN, W is W1a, and the combination of $R^1$ and $R^2$ for a compound in each case corresponds to one line of Table A.

Table 125
Compounds of the formulae I-a, I-b and I-d in which the group $C(R^{3a}R^{3b})$ is C=O, X is —C(O)NH-c-C$_3$H$_5$, $(R^{yy})_n$ is 5-CH$_3$, W is W1a, and the combination of $R^1$ and $R^2$ for a compound in each case corresponds to one line of Table A.

Table 126
Compounds of the formulae I-a, I-b, I-c and I-d in which the group $C(R^{3a}R^{3b})$ is $C(OH)_2$, X is —C(O)NH-c-C$_3$H$_5$, n=0, i.e. $(R^{yy})_n$ is absent, W is W1a, and the combination of $R^1$ and $R^2$ for a compound in each case corresponds to one line of Table A.

Table 127
Compounds of the formulae I-a, I-b, I-c and I-d in which the group $C(R^{3a}R^{3b})$ is $C(OH)_2$, X is —C(O)NH-c-C$_3$H$_5$, $(R^{yy})_n$ is 5-F, W is W1a, and the combination of $R^1$ and $R^2$ for a compound in each case corresponds to one line of Table A.

Table 128
Compounds of the formulae I-a, I-b and I-d in which the group $C(R^{3a}R^{3b})$ is $C(OH)_2$, X is —C(O)NH-c-C$_3$H$_5$, $(R^{yy})_n$ is 5-Cl, W is W1a, and the combination of $R^1$ and $R^2$ for a compound in each case corresponds to one line of Table A.

Table 129
Compounds of the formulae I-a, I-b and I-d in which the group $C(R^{3a}R^{3b})$ is $C(OH)_2$, X is —C(O)NH-c-C$_3$H$_5$, $(R^{yy})_n$ is 5-CN, W is W1a, and the combination of $R^1$ and $R^2$ for a compound in each case corresponds to one line of Table A.

Table 130
Compounds of the formulae I-a, I-b and I-d in which the group $C(R^{3a}R^{3b})$ is $C(OH)_2$, X is —C(O)NH-c-C$_3$H$_5$, $(R^{yy})_n$ is 5-CH$_3$, W is W1a, and the combination of $R^1$ and $R^2$ for a compound in each case corresponds to one line of Table A.

Table 131
Compounds of the formulae I-a, I-b, I-c and I-d in which the group $C(R^{3a}R^{3b})$ is C=O, X is —C(O)NH-c-C$_3$H$_5$, n=0, Table 132
Compounds of the formulae I-a, I-b and I-d in which the group $C(R^{3a}R^{3b})$ is C=O, X is —C(O)NH-c-$C_3H_5$, $(R^{yy})_n$ is 5-F, W is W1b, and the combination of $R^1$ and $R^2$ for a compound in each case corresponds to one line of Table A.

Table 133
Compounds of the formulae I-a, I-b and I-d in which the group $C(R^{3a}R^{3b})$ is C=O, X is —C(O)NH-c-$C_3H_5$, $(R^{yy})_n$ is 5-Cl, W is W1b, and the combination of $R^1$ and $R^2$ for a compound in each case corresponds to one line of Table A.

Table 134
Compounds of the formulae I-a, I-b and I-d in which the group $C(R^{3a}R^{3b})$ is C=O, X is —C(O)NH-c-$C_3H_5$, $(R^{yy})_n$ is 5-CN, W is W1b, and the combination of $R^1$ and $R^2$ for a compound in each case corresponds to one line of Table A.

Table 135
Compounds of the formulae I-a, I-b and I-d in which the group $C(R^{3a}R^{3b})$ is C=O, X is —C(O)NH-c-$C_3H_5$, $(R^{yy})_n$ is 5-$CH_3$, W is W1b, and the combination of $R^1$ and $R^2$ for a compound in each case corresponds to one line of Table A.

Table 136
Compounds of the formulae I-a, I-b, I-c and I-d in which the group $C(R^{3a}R^{3b})$ is $C(OH)_2$, X is —C(O)NH-c-$C_3H_5$, n=0, i.e. $(R^{yy})_n$ is absent, W is W1b, and the combination of $R^1$ and $R^2$ for a compound in each case corresponds to one line of Table A.

Table 137
Compounds of the formulae I-a, I-b, I-c and I-d in which the group $C(R^{3a}R^{3b})$ is $C(OH)_2$, X is —C(O)NH-c-$C_3H_5$, $(R^{yy})_n$ is 5-F, W is W1b, and the combination of $R^1$ and $R^2$ for a compound in each case corresponds to one line of Table A.

Table 138
Compounds of the formulae I-a, I-b and I-d in which the group $C(R^{3a}R^{3b})$ is $C(OH)_2$, X is —C(O)NH-c-$C_3H_5$, $(R^{yy})_n$ is 5-Cl, W is W1b, and the combination of $R^1$ and $R^2$ for a compound in each case corresponds to one line of Table A.

Table 139
Compounds of the formulae I-a, I-b and I-d in which the group $C(R^{3a}R^{3b})$ is $C(OH)_2$, X is —C(O)NH-c-$C_3H_5$, $(R^{yy})_n$ is 5-CN, W is W1b, and the combination of $R^1$ and $R^2$ for a compound in each case corresponds to one line of Table A.

Table 140
Compounds of the formulae I-a, I-b and I-d in which the group $C(R^{3a}R^{3b})$ is $C(OH)_2$, X is —C(O)NH-c-$C_3H_5$, $(R^{yy})_n$ is 5-$CH_3$, W is W1b, and the combination of $R^1$ and $R^2$ for a compound in each case corresponds to one line of Table A.

Table 141
Compounds of the formulae I-a, I-b, I-c and I-d in which the group $C(R^{3a}R^{3b})$ is C=O, X is —C(O)NH-c-$C_3H_5$, n=0, i.e. $(R^{yy})_n$ is absent, W is W2a, and the combination of $R^1$ and $R^2$ for a compound in each case corresponds to one line of Table A.

Table 142
Compounds of the formulae I-a, I-b and I-d in which the group $C(R^{3a}R^{3b})$ is C=O, X is —C(O)NH-c-$C_3H_5$, $(R^{yy})_n$ is 5-F, W is W2a, and the combination of $R^1$ and $R^2$ for a compound in each case corresponds to one line of Table A.

Table 143
Compounds of the formulae I-a, I-b and I-d in which the group $C(R^{3a}R^{3b})$ is C=O, X is —C(O)NH-c-$C_3H_5$, $(R^{yy})_n$ is 5-Cl, W is W2a, and the combination of $R^1$ and $R^2$ for a compound in each case corresponds to one line of Table A.

Table 144
Compounds of the formulae I-a, I-b and I-d in which the group $C(R^{3a}R^{3b})$ is C=O, X is —C(O)NH-c-$C_3H_5$, $(R^{yy})_n$ is 5-CN, W is W2a, and the combination of $R^1$ and $R^2$ for a compound in each case corresponds to one line of Table A.

Table 145
Compounds of the formulae I-a, I-b and I-d in which the group $C(R^{3a}R^{3b})$ is C=O, X is —C(O)NH-c-$C_3H_5$, $(R^{yy})_n$ is 5-$CH_3$, W is W2a, and the combination of $R^1$ and $R^2$ for a compound in each case corresponds to one line of Table A.

Table 146
Compounds of the formulae I-a, I-b, I-c and I-d in which the group $C(R^{3a}R^{3b})$ is $C(OH)_2$, X is —C(O)NH-c-$C_3H_5$, n=0, i.e. $(R^{yy})_n$ is absent, W is W2a, and the combination of $R^1$ and $R^2$ for a compound in each case corresponds to one line of Table A.

Table 147
Compounds of the formulae I-a, I-b, I-c and I-d in which the group $C(R^{3a}R^{3b})$ is $C(OH)_2$, X is —C(O)NH-c-$C_3H_5$, $(R^{yy})_n$ is 5-F, W is W2a, and the combination of $R^1$ and $R^2$ for a compound in each case corresponds to one line of Table A.

Table 148
Compounds of the formulae I-a, I-b and I-d in which the group $C(R^{3a}R^{3b})$ is $C(OH)_2$, X is —C(O)NH-c-$C_3H_5$, $(R^{yy})_n$ is 5-Cl, W is W2a, and the combination of $R^1$ and $R^2$ for a compound in each case corresponds to one line of Table A.

Table 149
Compounds of the formulae I-a, I-b and I-d in which the group $C(R^{3a}R^{3b})$ is $C(OH)_2$, X is —C(O)NH-c-$C_3H_5$, $(R^{yy})_n$ is 5-CN, W is W2a, and the combination of $R^1$ and $R^2$ for a compound in each case corresponds to one line of Table A.

Table 150
Compounds of the formulae I-a, I-b and I-d in which the group $C(R^{3a}R^{3b})$ is $C(OH)_2$, X is —C(O)NH-c-$C_3H_5$, $(R^{yy})_n$ is 5-$CH_3$, W is W2a, and the combination of $R^1$ and $R^2$ for a compound in each case corresponds to one line of Table A.

Table 151
Compounds of the formulae I-a, I-b, I-c and I-d in which the group $C(R^{3a}R^{3b})$ is C=O, X is —C(O)NH-c-$C_3H_5$, n=0, i.e. $(R^{yy})_n$ is absent, W is W2b, and the combination of $R^1$ and $R^2$ for a compound in each case corresponds to one line of Table A.

Table 152
Compounds of the formulae I-a, I-b and I-d in which the group $C(R^{3a}R^{3b})$ is C=O, X is —C(O)NH-c-$C_3H_5$, $(R^{yy})_n$ is 5-F, W is W2b, and the combination of $R^1$ and $R^2$ for a compound in each case corresponds to one line of Table A.

Table 153
Compounds of the formulae I-a, I-b and I-d in which the group $C(R^{3a}R^{3b})$ is C=O, X is —C(O)NH-c-$C_3H_5$, $(R^{yy})_n$ is 5-Cl, W is W2b, and the combination of $R^1$ and $R^2$ for a compound in each case corresponds to one line of Table A.

Table 154
Compounds of the formulae I-a, I-b and I-d in which the group $C(R^{3a}R^{3b})$ is C=O, X is —C(O)NH-c-$C_3H_5$, $(R^{yy})_n$ is 5-CN, W is W2b, and the combination of $R^1$ and $R^2$ for a compound in each case corresponds to one line of Table A.

Table 155
Compounds of the formulae I-a, I-b and I-d in which the group $C(R^{3a}R^{3b})$ is C=O, X is —C(O)NH-c-$C_3H_5$, $(R^{yy})_n$ is 5-$CH_3$, W is W2b, and the combination of $R^1$ and $R^2$ for a compound in each case corresponds to one line of Table A.

Table 156
Compounds of the formulae I-a, I-b, I-c and I-d in which the group $C(R^{3a}R^{3b})$ is $C(OH)_2$, X is —C(O)NH-c-$C_3H_5$, n=0, i.e. $(R^{yy})_n$ is absent, W is W2b, and the combination of $R^1$ and $R^2$ for a compound in each case corresponds to one line of Table A.

Table 157

Compounds of the formulae I-a, I-b, I-c and I-d in which the group $C(R^{3a}R^{3b})$ is $C(OH)_2$, X is —C(O)NH-c-$C_3H_5$, $(R^{yy})_n$ is 5-F, W is W1b, and the combination of $R^1$ and $R^2$ for a compound in each case corresponds to one line of Table A.

Table 158

Compounds of the formulae I-a, I-b and I-d in which the group $C(R^{3a}R^{3b})$ is $C(OH)_2$, X is —C(O)NH-c-$C_3H_5$, $(R^{yy})_n$ is 5-Cl, W is W2b, and the combination of $R^1$ and $R^2$ for a compound in each case corresponds to one line of Table A.

Table 159

Compounds of the formulae I-a, I-b and I-d in which the group $C(R^{3a}R^{3b})$ is $C(OH)_2$, X is —C(O)NH-c-$C_3H_5$, $(R^{yy})_n$ is 5-CN, W is W2b, and the combination of $R^1$ and $R^2$ for a compound in each case corresponds to one line of Table A.

Table 160

Compounds of the formulae I-a, I-b and I-d in which the group $C(R^{3a}R^{3b})$ is $C(OH)_2$, X is —C(O)NH-c-$C_3H_5$, $(R^{yy})_n$ is 5-$CH_3$, W is W2b, and the combination of $R^1$ and $R^2$ for a compound in each case corresponds to one line of Table A.

TABLE A

| No. | $R^1$ | $R^2$ |
|---|---|---|
| A-1 | n-Butyl | Phenyl |
| A-2 | n-Butyl | 2-Methylphenyl |
| A-3 | n-Butyl | 2-Methoxyphenyl |
| A-4 | n-Butyl | 2-Chlorophenyl |
| A-5 | n-Butyl | 2-Fluorophenyl |
| A-6 | n-Butyl | 2-Trifluoromethylphenyl |
| A-7 | n-Butyl | 3-Methylphenyl |
| A-8 | n-Butyl | 3-Methoxyphenyl |
| A-9 | n-Butyl | 3-Chlorophenyl |
| A-10 | n-Butyl | 3-Fluorophenyl |
| A-11 | n-Butyl | 3-[(Phenylmethyl)oxy]phenyl |
| A-12 | n-Butyl | 3-Morpholin-4-ylphenyl |
| A-13 | n-Butyl | 3-(Morpholin-4-ylmethyl)phenyl |
| A-14 | n-Butyl | 3-Pyrrolidin-1-ylphenyl |
| A-15 | n-Butyl | 4-Methylphenyl |
| A-16 | n-Butyl | 4-(1-Methylethyl)phenyl |
| A-17 | n-Butyl | 4-Methoxyphenyl |
| A-18 | n-Butyl | 4-Chlorophenyl |
| A-19 | n-Butyl | 4-Fluorophenyl |
| A-20 | n-Butyl | 4-Trifluoromethylphenyl |
| A-21 | n-Butyl | 4-Diethylaminophenyl |
| A-22 | n-Butyl | 4-[(Diethylamino)methyl]phenyl |
| A-23 | n-Butyl | 4-Cyanophenyl |
| A-24 | n-Butyl | 4-(Piperidin-1-yl)phenyl |
| A-25 | n-Butyl | 4-(4-Methylpiperazin-1-yl)phenyl |
| A-26 | n-Butyl | 4-Pyrrolidin-1-ylphenyl |
| A-27 | n-Butyl | 4-(1H-Imidazol-1-yl)phenyl |
| A-28 | n-Butyl | 4-Morpholin-4-ylphenyl |
| A-29 | n-Butyl | 4-(Morpholin-4-ylmethyl)phenyl |
| A-30 | n-Butyl | 2,4-Difluorophenyl |
| A-31 | n-Butyl | 2,6-Difluorophenyl |
| A-32 | n-Butyl | 3,5-Difluorophenyl |
| A-33 | n-Butyl | 2,4-Dichlorophenyl |
| A-34 | n-Butyl | 2,6-Dichlorophenyl |
| A-35 | n-Butyl | 3,5-Dichlorophenyl |
| A-36 | n-Butyl | 2-Chloro-4-fluorophenyl |
| A-37 | n-Butyl | 2-Chloro-4-morpholin-4-ylphenyl |
| A-38 | n-Butyl | 2-Fluoro-4-morpholin-4-ylphenyl |
| A-39 | n-Butyl | Pyridin-2-yl |
| A-40 | n-Butyl | Pyridin-4-yl |
| A-41 | n-Butyl | Thien-2-yl |
| A-42 | n-Butyl | 2,3-Dihydrobenzo[b]furan-5-yl |
| A-43 | Isobutyl | Phenyl |
| A-44 | Isobutyl | 2-Methylphenyl |
| A-45 | Isobutyl | 2-Methoxyphenyl |
| A-46 | Isobutyl | 2-Chlorophenyl |
| A-47 | Isobutyl | 2-Fluorophenyl |
| A-48 | Isobutyl | 2-Trifluoromethylphenyl |
| A-49 | Isobutyl | 3-Methylphenyl |
| A-50 | Isobutyl | 3-Methoxyphenyl |
| A-51 | Isobutyl | 3-Chlorophenyl |
| A-52 | Isobutyl | 3-Fluorophenyl |
| A-53 | Isobutyl | 3-[(Phenylmethyl)oxy]phenyl |
| A-54 | Isobutyl | 3-Morpholin-4-ylphenyl |
| A-55 | Isobutyl | 3-(Morpholin-4-ylmethyl)phenyl |
| A-56 | Isobutyl | 3-Pyrrolidin-1-ylphenyl |
| A-57 | Isobutyl | 4-Methylphenyl |
| A-58 | Isobutyl | 4-(1-Methylethyl)phenyl |
| A-59 | Isobutyl | 4-Methoxyphenyl |
| A-60 | Isobutyl | 4-Chlorophenyl |
| A-61 | Isobutyl | 4-Fluorophenyl |
| A-62 | Isobutyl | 4-Trifluoromethylphenyl |
| A-63 | Isobutyl | 4-Diethylaminophenyl |
| A-64 | Isobutyl | 4-[(Diethylamino)methyl]phenyl |
| A-65 | Isobutyl | 4-Cyanophenyl |
| A-66 | Isobutyl | 4-(Piperidin-1-yl)phenyl |
| A-67 | Isobutyl | 4-(4-Methylpiperazin-1-yl)phenyl |
| A-68 | Isobutyl | 4-Pyrrolidin-1-ylphenyl |
| A-69 | Isobutyl | 4-(1H-Imidazol-1-yl)phenyl |
| A-70 | Isobutyl | 4-Morpholin-4-ylphenyl |
| A-71 | Isobutyl | 4-(Morpholin-4-ylmethyl)phenyl |
| A-72 | Isobutyl | 2,4-Difluorophenyl |
| A-73 | Isobutyl | 2,6-Difluorophenyl |
| A-74 | Isobutyl | 3,5-Difluorophenyl |
| A-75 | Isobutyl | 2,4-Dichlorophenyl |
| A-76 | Isobutyl | 2,6-Dichlorophenyl |
| A-77 | Isobutyl | 3,5-Dichlorophenyl |
| A-78 | Isobutyl | 2-Chloro-4-fluorophenyl |
| A-79 | Isobutyl | 2-Chloro-4-morpholin-4-ylphenyl |
| A-80 | Isobutyl | 2-Fluoro-4-morpholin-4-ylphenyl |
| A-81 | Isobutyl | Pyridin-2-yl |
| A-82 | Isobutyl | Pyridin-4-yl |
| A-83 | Isobutyl | Thien-2-yl |
| A-84 | Isobutyl | 2,3-Dihydrobenzo[b]furan-5-yl |
| A-85 | Benzyl | Phenyl |
| A-86 | Benzyl | 2-Methylphenyl |
| A-87 | Benzyl | 2-Methoxyphenyl |
| A-88 | Benzyl | 2-Chlorophenyl |
| A-89 | Benzyl | 2-Fluorophenyl |
| A-90 | Benzyl | 2-Trifluoromethylphenyl |
| A-91 | Benzyl | 3-Methylphenyl |
| A-92 | Benzyl | 3-Methoxyphenyl |
| A-93 | Benzyl | 3-Chlorophenyl |
| A-94 | Benzyl | 3-Fluorophenyl |
| A-95 | Benzyl | 3-[(Phenylmethyl)oxy]phenyl |
| A-96 | Benzyl | 3-Morpholin-4-ylphenyl |
| A-97 | Benzyl | 3-(Morpholin-4-ylmethyl)phenyl |
| A-98 | Benzyl | 3-Pyrrolidin-1-ylphenyl |
| A-99 | Benzyl | 4-Methylphenyl |
| A-100 | Benzyl | 4-(1-Methylethyl)phenyl |
| A-101 | Benzyl | 4-Methoxyphenyl |
| A-102 | Benzyl | 4-Chlorophenyl |
| A-103 | Benzyl | 4-Fluorophenyl |
| A-104 | Benzyl | 4-Trifluoromethylphenyl |
| A-105 | Benzyl | 4-Diethylaminophenyl |
| A-106 | Benzyl | 4-[(Diethylamino)methyl]phenyl |
| A-107 | Benzyl | 4-Cyanophenyl |
| A-108 | Benzyl | 4-(Piperidin-1-yl)phenyl |
| A-109 | Benzyl | 4-(4-Methylpiperazin-1-yl)phenyl |
| A-110 | Benzyl | 4-Pyrrolidin-1-ylphenyl |
| A-111 | Benzyl | 4-(1H-Imidazol-1-yl)phenyl |
| A-112 | Benzyl | 4-Morpholin-4-ylphenyl |
| A-113 | Benzyl | 4-(Morpholin-4-ylmethyl)phenyl |
| A-114 | Benzyl | 2,4-Difluorophenyl |
| A-115 | Benzyl | 2,6-Difluorophenyl |
| A-116 | Benzyl | 3,5-Difluorophenyl |
| A-117 | Benzyl | 2,4-Dichlorophenyl |
| A-118 | Benzyl | 2,6-Dichlorophenyl |
| A-119 | Benzyl | 3,5-Dichlorophenyl |
| A-120 | Benzyl | 2-Chloro-4-fluorophenyl |
| A-121 | Benzyl | 2-Chloro-4-morpholin-4-ylphenyl |
| A-122 | Benzyl | 2-Fluoro-4-morpholin-4-ylphenyl |
| A-123 | Benzyl | Pyridin-2-yl |
| A-124 | Benzyl | Pyridin-4-yl |
| A-125 | Benzyl | Thien-2-yl |
| A-126 | Benzyl | 2,3-Dihydrobenzo[b]furan-5-yl |

TABLE A-continued

| No. | R¹ | R² |
|---|---|---|
| A-127 | 4-Chlorobenzyl | Phenyl |
| A-128 | 4-Chlorobenzyl | 2-Methylphenyl |
| A-129 | 4-Chlorobenzyl | 2-Methoxyphenyl |
| A-130 | 4-Chlorobenzyl | 2-Chlorophenyl |
| A-131 | 4-Chlorobenzyl | 2-Fluorophenyl |
| A-132 | 4-Chlorobenzyl | 2-Trifluoromethylphenyl |
| A-133 | 4-Chlorobenzyl | 3-Methylphenyl |
| A-134 | 4-Chlorobenzyl | 3-Methoxyphenyl |
| A-135 | 4-Chlorobenzyl | 3-Chlorophenyl |
| A-136 | 4-Chlorobenzyl | 3-Fluorophenyl |
| A-137 | 4-Chlorobenzyl | 3-[(Phenylmethyl)oxy]phenyl |
| A-138 | 4-Chlorobenzyl | 3-Morpholin-4-ylphenyl |
| A-139 | 4-Chlorobenzyl | 3-(Morpholin-4-ylmethyl)phenyl |
| A-140 | 4-Chlorobenzyl | 3-Pyrrolidin-1-ylphenyl |
| A-141 | 4-Chlorobenzyl | 4-Methylphenyl |
| A-142 | 4-Chlorobenzyl | 4-(1-Methylethyl)phenyl |
| A-143 | 4-Chlorobenzyl | 4-Methoxyphenyl |
| A-144 | 4-Chlorobenzyl | 4-Chlorophenyl |
| A-145 | 4-Chlorobenzyl | 4-Fluorophenyl |
| A-146 | 4-Chlorobenzyl | 4-Trifluoromethylphenyl |
| A-147 | 4-Chlorobenzyl | 4-Diethylaminophenyl |
| A-148 | 4-Chlorobenzyl | 4-[(Diethylamino)methyl]phenyl |
| A-149 | 4-Chlorobenzyl | 4-Cyanophenyl |
| A-150 | 4-Chlorobenzyl | 4-(Piperidin-1-yl)phenyl |
| A-151 | 4-Chlorobenzyl | 4-(4-Methylpiperazin-1-yl)phenyl |
| A-152 | 4-Chlorobenzyl | 4-Pyrrolidin-1-ylphenyl |
| A-153 | 4-Chlorobenzyl | 4-(1H-Imidazol-1-yl)phenyl |
| A-154 | 4-Chlorobenzyl | 4-Morpholin-4-ylphenyl |
| A-155 | 4-Chlorobenzyl | 4-(Morpholin-4-ylmethyl)phenyl |
| A-156 | 4-Chlorobenzyl | 2,4-Difluorophenyl |
| A-157 | 4-Chlorobenzyl | 2,6-Difluorophenyl |
| A-158 | 4-Chlorobenzyl | 3,5-Difluorophenyl |
| A-159 | 4-Chlorobenzyl | 2,4-Dichlorophenyl |
| A-160 | 4-Chlorobenzyl | 2,6-Dichlorophenyl |
| A-161 | 4-Chlorobenzyl | 3,5-Dichlorophenyl |
| A-162 | 4-Chlorobenzyl | 2-Chloro-4-fluorophenyl |
| A-163 | 4-Chlorobenzyl | 2-Chloro-4-morpholin-4-ylphenyl |
| A-164 | 4-Chlorobenzyl | 2-Fluoro-4-morpholin-4-ylphenyl |
| A-165 | 4-Chlorobenzyl | Pyridin-2-yl |
| A-166 | 4-Chlorobenzyl | Pyridin-4-yl |
| A-167 | 4-Chlorobenzyl | Thien-2-yl |
| A-168 | 4-Chlorobenzyl | 2,3-Dihydrobenzo[b]furan-5-yl |
| A-169 | 4-Methoxybenzyl | Phenyl |
| A-170 | 4-Methoxybenzyl | 2-Methylphenyl |
| A-171 | 4-Methoxybenzyl | 2-Methoxyphenyl |
| A-172 | 4-Methoxybenzyl | 2-Chlorophenyl |
| A-173 | 4-Methoxybenzyl | 2-Fluorophenyl |
| A-174 | 4-Methoxybenzyl | 2-Trifluoromethylphenyl |
| A-175 | 4-Methoxybenzyl | 3-Methylphenyl |
| A-176 | 4-Methoxybenzyl | 3-Methoxyphenyl |
| A-177 | 4-Methoxybenzyl | 3-Chlorophenyl |
| A-178 | 4-Methoxybenzyl | 3-Fluorophenyl |
| A-179 | 4-Methoxybenzyl | 3-[(Phenylmethyl)oxy]phenyl |
| A-180 | 4-Methoxybenzyl | 3-Morpholin-4-ylphenyl |
| A-181 | 4-Methoxybenzyl | 3-(Morpholin-4-ylmethyl)phenyl |
| A-182 | 4-Methoxybenzyl | 3-Pyrrolidin-1-ylphenyl |
| A-183 | 4-Methoxybenzyl | 4-Methylphenyl |
| A-184 | 4-Methoxybenzyl | 4-(1-Methylethyl)phenyl |
| A-185 | 4-Methoxybenzyl | 4-Methoxyphenyl |
| A-186 | 4-Methoxybenzyl | 4-Chlorophenyl |
| A-187 | 4-Methoxybenzyl | 4-Fluorophenyl |
| A-188 | 4-Methoxybenzyl | 4-Trifluoromethylphenyl |
| A-189 | 4-Methoxybenzyl | 4-Diethylaminophenyl |
| A-190 | 4-Methoxybenzyl | 4-[(Diethylamino)methyl]phenyl |
| A-191 | 4-Methoxybenzyl | 4-Cyanophenyl |
| A-192 | 4-Methoxybenzyl | 4-(Piperidin-1-yl)phenyl |
| A-193 | 4-Methoxybenzyl | 4-(4-Methylpiperazin-1-yl)phenyl |
| A-194 | 4-Methoxybenzyl | 4-Pyrrolidin-1-ylphenyl |
| A-195 | 4-Methoxybenzyl | 4-(1H-Imidazol-1-yl)phenyl |
| A-196 | 4-Methoxybenzyl | 4-Morpholin-4-ylphenyl |
| A-197 | 4-Methoxybenzyl | 4-(Morpholin-4-ylmethyl)phenyl |
| A-198 | 4-Methoxybenzyl | 2,4-Difluorophenyl |
| A-199 | 4-Methoxybenzyl | 2,6-Difluorophenyl |
| A-200 | 4-Methoxybenzyl | 3,5-Difluorophenyl |
| A-201 | 4-Methoxybenzyl | 2,4-Dichlorophenyl |
| A-202 | 4-Methoxybenzyl | 2,6-Dichlorophenyl |
| A-203 | 4-Methoxybenzyl | 3,5-Dichlorophenyl |
| A-204 | 4-Methoxybenzyl | 2-Chloro-4-fluorophenyl |
| A-205 | 4-Methoxybenzyl | 2-Chloro-4-morpholin-4-ylphenyl |
| A-206 | 4-Methoxybenzyl | 2-Fluoro-4-morpholin-4-ylphenyl |
| A-207 | 4-Methoxybenzyl | Pyridin-2-yl |
| A-208 | 4-Methoxybenzyl | Pyridin-4-yl |
| A-209 | 4-Methoxybenzyl | Thien-2-yl |
| A-210 | 4-Methoxybenzyl | 2,3-Dihydrobenzo[b]furan-5-yl |
| A-211 | Cyclohexylmethyl | Phenyl |
| A-212 | Cyclohexylmethyl | 2-Methylphenyl |
| A-213 | Cyclohexylmethyl | 2-Methoxyphenyl |
| A-214 | Cyclohexylmethyl | 2-Chlorophenyl |
| A-215 | Cyclohexylmethyl | 2-Fluorophenyl |
| A-216 | Cyclohexylmethyl | 2-Trifluoromethylphenyl |
| A-217 | Cyclohexylmethyl | 3-Methylphenyl |
| A-218 | Cyclohexylmethyl | 3-Methoxyphenyl |
| A-219 | Cyclohexylmethyl | 3-Chlorophenyl |
| A-220 | Cyclohexylmethyl | 3-Fluorophenyl |
| A-221 | Cyclohexylmethyl | 3-[(Phenylmethyl)oxy]phenyl |
| A-222 | Cyclohexylmethyl | 3-Morpholin-4-ylphenyl |
| A-223 | Cyclohexylmethyl | 3-(Morpholin-4-ylmethyl)phenyl |
| A-224 | Cyclohexylmethyl | 3-Pyrrolidin-1-ylphenyl |
| A-225 | Cyclohexylmethyl | 4-Methylphenyl |
| A-226 | Cyclohexylmethyl | 4-(1-Methylethyl)phenyl |
| A-227 | Cyclohexylmethyl | 4-Methoxyphenyl |
| A-228 | Cyclohexylmethyl | 4-Chlorophenyl |
| A-229 | Cyclohexylmethyl | 4-Fluorophenyl |
| A-230 | Cyclohexylmethyl | 4-Trifluoromethylphenyl |
| A-231 | Cyclohexylmethyl | 4-Diethylaminophenyl |
| A-232 | Cyclohexylmethyl | 4-[(Diethylamino)methyl]phenyl |
| A-233 | Cyclohexylmethyl | 4-Cyanophenyl |
| A-234 | Cyclohexylmethyl | 4-(Piperidin-1-yl)phenyl |
| A-235 | Cyclohexylmethyl | 4-(4-Methylpiperazin-1-yl)phenyl |
| A-236 | Cyclohexylmethyl | 4-Pyrrolidin-1-ylphenyl |
| A-237 | Cyclohexylmethyl | 4-(1H-Imidazol-1-yl)phenyl |
| A-238 | Cyclohexylmethyl | 4-Morpholin-4-ylphenyl |
| A-239 | Cyclohexylmethyl | 4-(Morpholin-4-ylmethyl)phenyl |
| A-240 | Cyclohexylmethyl | 2,4-Difluorophenyl |
| A-241 | Cyclohexylmethyl | 2,6-Difluorophenyl |
| A-242 | Cyclohexylmethyl | 3,5-Difluorophenyl |
| A-243 | Cyclohexylmethyl | 2,4-Dichlorophenyl |
| A-244 | Cyclohexylmethyl | 2,6-Dichlorophenyl |
| A-245 | Cyclohexylmethyl | 3,5-Dichlorophenyl |
| A-246 | Cyclohexylmethyl | 2-Chloro-4-fluorophenyl |
| A-247 | Cyclohexylmethyl | 2-Chloro-4-morpholin-4-ylphenyl |
| A-248 | Cyclohexylmethyl | 2-Fluoro-4-morpholin-4-ylphenyl |
| A-249 | Cyclohexylmethyl | Pyridin-2-yl |
| A-250 | Cyclohexylmethyl | Pyridin-4-yl |
| A-251 | Cyclohexylmethyl | Thien-2-yl |
| A-252 | Cyclohexylmethyl | 2,3-Dihydrobenzo[b]furan-5-yl |
| A-253 | 2-Thienylmethyl | Phenyl |
| A-254 | 2-Thienylmethyl | 2-Methylphenyl |
| A-255 | 2-Thienylmethyl | 2-Methoxyphenyl |
| A-256 | 2-Thienylmethyl | 2-Chlorophenyl |
| A-257 | 2-Thienylmethyl | 2-Fluorophenyl |
| A-258 | 2-Thienylmethyl | 2-Trifluoromethylphenyl |
| A-259 | 2-Thienylmethyl | 3-Methylphenyl |
| A-260 | 2-Thienylmethyl | 3-Methoxyphenyl |
| A-261 | 2-Thienylmethyl | 3-Chlorophenyl |
| A-262 | 2-Thienylmethyl | 3-Fluorophenyl |
| A-263 | 2-Thienylmethyl | 3-[(Phenylmethyl)oxy]phenyl |
| A-264 | 2-Thienylmethyl | 3-Morpholin-4-ylphenyl |
| A-265 | 2-Thienylmethyl | 3-(Morpholin-4-ylmethyl)phenyl |
| A-266 | 2-Thienylmethyl | 3-Pyrrolidin-1-ylphenyl |
| A-267 | 2-Thienylmethyl | 4-Methylphenyl |
| A-268 | 2-Thienylmethyl | 4-(1-Methylethyl)phenyl |
| A-269 | 2-Thienylmethyl | 4-Methoxyphenyl |
| A-270 | 2-Thienylmethyl | 4-Chlorophenyl |
| A-271 | 2-Thienylmethyl | 4-Fluorophenyl |
| A-272 | 2-Thienylmethyl | 4-Trifluoromethylphenyl |
| A-273 | 2-Thienylmethyl | 4-Diethylaminophenyl |
| A-274 | 2-Thienylmethyl | 4-[(Diethylamino)methyl]phenyl |
| A-275 | 2-Thienylmethyl | 4-Cyanophenyl |
| A-276 | 2-Thienylmethyl | 4-(Piperidin-1-yl)phenyl |
| A-277 | 2-Thienylmethyl | 4-(4-Methylpiperazin-1-yl)phenyl |
| A-278 | 2-Thienylmethyl | 4-Pyrrolidin-1-ylphenyl |
| A-279 | 2-Thienylmethyl | 4-(1H-Imidazol-1-yl)phenyl |
| A-280 | 2-Thienylmethyl | 4-Morpholin-4-ylphenyl |
| A-281 | 2-Thienylmethyl | 4-(Morpholin-4-ylmethyl)phenyl |
| A-282 | 2-Thienylmethyl | 2,4-Difluorophenyl |

TABLE A-continued

| No. | R¹ | R² |
|---|---|---|
| A-283 | 2-Thienylmethyl | 2,6-Difluorophenyl |
| A-284 | 2-Thienylmethyl | 3,5-Difluorophenyl |
| A-285 | 2-Thienylmethyl | 2,4-Dichlorophenyl |
| A-286 | 2-Thienylmethyl | 2,6-Dichlorophenyl |
| A-287 | 2-Thienylmethyl | 3,5-Dichlorophenyl |
| A-288 | 2-Thienylmethyl | 2-Chloro-4-fluorophenyl |
| A-289 | 2-Thienylmethyl | 2-Chloro-4-morpholin-4-ylphenyl |
| A-290 | 2-Thienylmethyl | 2-Fluoro-4-morpholin-4-ylphenyl |
| A-291 | 2-Thienylmethyl | Pyridin-2-yl |
| A-292 | 2-Thienylmethyl | Pyridin-4-yl |
| A-293 | 2-Thienylmethyl | Thien-2-yl |
| A-294 | 2-Thienylmethyl | 2,3-Dihydrobenzo[b]furan-5-yl |
| A-295 | Pyridin-3-ylmethyl | Phenyl |
| A-296 | Pyridin-3-ylmethyl | 2-Methylphenyl |
| A-297 | Pyridin-3-ylmethyl | 2-Methoxyphenyl |
| A-298 | Pyridin-3-ylmethyl | 2-Chlorophenyl |
| A-299 | Pyridin-3-ylmethyl | 2-Fluorophenyl |
| A-300 | Pyridin-3-ylmethyl | 2-Trifluoromethylphenyl |
| A-301 | Pyridin-3-ylmethyl | 3-Methylphenyl |
| A-302 | Pyridin-3-ylmethyl | 3-Methoxyphenyl |
| A-303 | Pyridin-3-ylmethyl | 3-Chlorophenyl |
| A-304 | Pyridin-3-ylmethyl | 3-Fluorophenyl |
| A-305 | Pyridin-3-ylmethyl | 3-[(Phenylmethyl)oxy]phenyl |
| A-306 | Pyridin-3-ylmethyl | 3-Morpholin-4-ylphenyl |
| A-307 | Pyridin-3-ylmethyl | 3-(Morpholin-4-ylmethyl)phenyl |
| A-308 | Pyridin-3-ylmethyl | 3-Pyrrolidin-1-ylphenyl |
| A-309 | Pyridin-3-ylmethyl | 4-Methylphenyl |
| A-310 | Pyridin-3-ylmethyl | 4-(1-Methylethyl)phenyl |
| A-311 | Pyridin-3-ylmethyl | 4-Methoxyphenyl |
| A-312 | Pyridin-3-ylmethyl | 4-Chlorophenyl |
| A-313 | Pyridin-3-ylmethyl | 4-Fluorophenyl |
| A-314 | Pyridin-3-ylmethyl | 4-Trifluoromethylphenyl |
| A-315 | Pyridin-3-ylmethyl | 4-Diethylaminophenyl |
| A-316 | Pyridin-3-ylmethyl | 4-[(Diethylamino)methyl]phenyl |
| A-317 | Pyridin-3-ylmethyl | 4-Cyanophenyl |
| A-318 | Pyridin-3-ylmethyl | 4-(Piperidin-1-yl)phenyl |
| A-319 | Pyridin-3-ylmethyl | 4-(4-Methylpiperazin-1-yl)phenyl |
| A-320 | Pyridin-3-ylmethyl | 4-Pyrrolidin-1-ylphenyl |
| A-321 | Pyridin-3-ylmethyl | 4-(1H-Imidazol-1-yl)phenyl |
| A-322 | Pyridin-3-ylmethyl | 4-Morpholin-4-ylphenyl |
| A-323 | Pyridin-3-ylmethyl | 4-(Morpholin-4-ylmethyl)phenyl |
| A-324 | Pyridin-3-ylmethyl | 2,4-Difluorophenyl |
| A-325 | Pyridin-3-ylmethyl | 2,6-Difluorophenyl |
| A-326 | Pyridin-3-ylmethyl | 3,5-Difluorophenyl |
| A-327 | Pyridin-3-ylmethyl | 2,4-Dichlorophenyl |
| A-328 | Pyridin-3-ylmethyl | 2,6-Dichlorophenyl |
| A-329 | Pyridin-3-ylmethyl | 3,5-Dichlorophenyl |
| A-330 | Pyridin-3-ylmethyl | 2-Chloro-4-fluorophenyl |
| A-331 | Pyridin-3-ylmethyl | 2-Chloro-4-morpholin-4-ylphenyl |
| A-332 | Pyridin-3-ylmethyl | 2-Fluoro-4-morpholin-4-ylphenyl |
| A-333 | Pyridin-3-ylmethyl | Pyridin-2-yl |
| A-334 | Pyridin-3-ylmethyl | Pyridin-4-yl |
| A-335 | Pyridin-3-ylmethyl | Thien-2-yl |
| A-336 | Pyridin-3-ylmethyl | 2,3-Dihydrobenzo[b]furan-5-yl |

With regard to subsequent Tables 161 to 200 the groups W—R² in formulae I-a, I-b, I-c and I-d represent a radical W3, in accordance to the aforementioned definition.

Table 161
Compounds of the formulae I-a, I-b, I-c and I-d in which the group $C(R^{3a}R^{3b})$ is C=O, X is carbamoyl, n=0, i.e. $(R^{yy})_n$ is absent, and the combination of $R^1$ and W3 for a compound in each case corresponds to one line of Table B.

Table 162
Compounds of the formulae I-a, I-b and I-d in which the group $C(R^{3a}R^{3b})$ is C=O, X is carbamoyl, $(R^{yy})_n$ is 5-F, and the combination of $R^1$ and W3 for a compound in each case corresponds to one line of Table B.

Table 163
Compounds of the formulae I-a, I-b and I-d in which the group $C(R^{3a}R^{3b})$ is C=O, X is carbamoyl, $(R^{yy})_n$ is 5-Cl, and the combination of $R^1$ and W3 for a compound in each case corresponds to one line of Table B.

Table 164
Compounds of the formulae I-a, I-b and I-d in which the group $C(R^{3a}R^{3b})$ is C=O, X is carbamoyl, $(R^{yy})_n$ is 5-CN, and the combination of $R^1$ and W3 for a compound in each case corresponds to one line of Table B.

Table 165
Compounds of the formulae I-a, I-b and I-d in which the group $C(R^{3a}R^{3b})$ is C=O, X is carbamoyl, $(R^{yy})_n$ is 5-CH₃, and the combination of $R^1$ and W3 for a compound in each case corresponds to one line of Table B.

Table 166
Compounds of the formulae I-a, I-b, I-c and I-d in which the group $C(R^{3a}R^{3b})$ is C=O, X is —C(O)NHCH₃, n=0, i.e. $(R^{yy})_n$ is absent, and the combination of $R^1$ and W3 for a compound in each case corresponds to one line of Table B.

Table 167
Compounds of the formulae I-a, I-b and I-d in which the group $C(R^{3a}R^{3b})$ is C=O, X is —C(O)NHCH₃, $(R^{yy})_n$ is 5-F, and the combination of $R^1$ and W3 for a compound in each case corresponds to one line of Table B.

Table 168
Compounds of the formulae I-a, I-b and I-d in which the group $C(R^{3a}R^{3b})$ is C=O, X is —C(O)NHCH₃, $(R^{yy})_n$ is 5-Cl, and the combination of $R^1$ and W3 for a compound in each case corresponds to one line of Table B.

Table 169
Compounds of the formulae I-a, I-b and I-d in which the group $C(R^{3a}R^{3b})$ is C=O, X is —C(O)NHCH₃, $(R^{yy})_n$ is 5-CN, and the combination of $R^1$ and W3 for a compound in each case corresponds to one line of Table B.

Table 170
Compounds of the formulae I-a, I-b and I-d in which the group $C(R^{3a}R^{3b})$ is C=O, X is —C(O)NHCH₃, $(R^{yy})_n$ is 5-CH₃, and the combination of $R^1$ and W3 for a compound in each case corresponds to one line of Table B.

Table 171
Compounds of the formulae I-a, I-b, I-c and I-d in which the group $C(R^{3a}R^{3b})$ is C(OH)₂, X is carbamoyl, n=0, i.e. $(R^{yy})_n$ is absent, and the combination of $R^1$ and W3 for a compound in each case corresponds to one line of Table B.

Table 172
Compounds of the formulae I-a, I-b and I-d in which the group $C(R^{3a}R^{3b})$ is C(OH)₂, X is carbamoyl, $(R^{yy})_n$ is 5-F, and the combination of $R^1$ and W3 for a compound in each case corresponds to one line of Table B.

Table 173
Compounds of the formulae I-a, I-b and I-d in which the group $C(R^{3a}R^{3b})$ is C(OH)₂, X is carbamoyl, $(R^{yy})_n$ is 5-Cl, and the combination of $R^1$ and W3 for a compound in each case corresponds to one line of Table B.

Table 174
Compounds of the formulae I-a, I-b and I-d in which the group $C(R^{3a}R^{3b})$ is C(OH)₂, X is carbamoyl, $(R^{yy})_n$ is 5-CN, and the combination of $R^1$ and W3 for a compound in each case corresponds to one line of Table B.

Table 175
Compounds of the formulae I-a, I-b and I-d in which the group $C(R^{3a}R^{3b})$ is C(OH)₂, X is carbamoyl, $(R^{yy})_n$ is 5-CH₃, and the combination of $R^1$ and W3 for a compound in each case corresponds to one line of Table B.

Table 176
Compounds of the formulae I-a, I-b, I-c and I-d in which the group $C(R^{3a}R^{3b})$ is C(OH)₂, X is —C(O)NHCH₃, n=0, i.e. $(R^{yy})_n$ is absent, and the combination of $R^1$ and W3 for a compound in each case corresponds to one line of Table B.

Table 177
Compounds of the formulae I-a, I-b, I-c and I-d in which the group $C(R^{3a}R^{3b})$ is $C(OH)_2$, X is —C(O)NHCH$_3$, $(R^{yy})_n$ is 5-F, and the combination of $R^1$ and W3 for a compound in each case corresponds to one line of Table B.

Table 178
Compounds of the formulae I-a, I-b and I-d in which the group $C(R^{3a}R^{3b})$ is $C(OH)_2$, X is —C(O)NHCH$_3$, $(R^{yy})_n$ is 5-Cl, and the combination of $R^1$ and W3 for a compound in each case corresponds to one line of Table B.

Table 179
Compounds of the formulae I-a, I-b and I-d in which the group $C(R^{3a}R^{3b})$ is $C(OH)_2$, X is —C(O)NHCH$_3$, $(R^{yy})_n$ is 5-CN, and the combination of $R^1$ and W3 for a compound in each case corresponds to one line of Table B.

Table 180
Compounds of the formulae I-a, I-b and I-d in which the group $C(R^{3a}R^{3b})$ is $C(OH)_2$, X is —C(O)NHCH$_3$, $(R^{yy})_n$ is 5-CH$_3$, and the combination of $R^1$ and W3 for a compound in each case corresponds to one line of Table B.

Table 181
Compounds of the formulae I-a, I-b, I-c and I-d in which the group $C(R^{3a}R^{3b})$ is C=O, X is —C(O)NHOCH$_3$, n=0, i.e. $(R^{yy})_n$ is absent, and the combination of $R^1$ and W3 for a compound in each case corresponds to one line of Table B.

Table 182
Compounds of the formulae I-a, I-b and I-d in which the group $C(R^{3a}R^{3b})$ is C=O, X is —C(O)NHOCH$_3$, $(R^{yy})_n$ is 5-F, and the combination of $R^1$ and W3 for a compound in each case corresponds to one line of Table B.

Table 183
Compounds of the formulae I-a, I-b and I-d in which the group $C(R^{3a}R^{3b})$ is C=O, X is —C(O)NHOCH$_3$, $(R^{yy})_n$ is 5-Cl, and the combination of $R^1$ and W3 for a compound in each case corresponds to one line of Table B.

Table 184
Compounds of the formulae I-a, I-b and I-d in which the group $C(R^{3a}R^{3b})$ is C=O, X is —C(O)NHOCH$_3$, $(R^{yy})_n$ is 5-CN, and the combination of $R^1$ and W3 for a compound in each case corresponds to one line of Table B.

Table 185
Compounds of the formulae I-a, I-b and I-d in which the group $C(R^{3a}R^{3b})$ is C=O, X is —C(O)NHOCH$_3$, $(R^{yy})_n$ is 5-CH$_3$, and the combination of $R^1$ and W3 for a compound in each case corresponds to one line of Table B.

Table 186
Compounds of the formulae I-a, I-b, I-c and I-d in which the group $C(R^{3a}R^{3b})$ is $C(OH)_2$, X is —C(O)NHOCH$_3$, n=0, i.e. $(R^{yy})_n$ is absent, and the combination of $R^1$ and W3 for a compound in each case corresponds to one line of Table B.

Table 187
Compounds of the formulae I-a, I-b, I-c and I-d in which the group $C(R^{3a}R^{3b})$ is $C(OH)_2$, X is —C(O)NHOCH$_3$, $(R^{yy})_n$ is 5-F, and the combination of $R^1$ and W3 for a compound in each case corresponds to one line of Table B.

Table 188
Compounds of the formulae I-a, I-b and I-d in which the group $C(R^{3a}R^{3b})$ is $C(OH)_2$, X is —C(O)NHOCH$_3$, $(R^{yy})_n$ is 5-Cl, and the combination of $R^1$ and W3 for a compound in each case corresponds to one line of Table B.

Table 189
Compounds of the formulae I-a, I-b and I-d in which the group $C(R^{3a}R^{3b})$ is $C(OH)_2$, X is —C(O)NHOCH$_3$, $(R^{yy})_n$ is 5-CN, and the combination of $R^1$ and W3 for a compound in each case corresponds to one line of Table B.

Table 190
Compounds of the formulae I-a, I-b and I-d in which the group $C(R^{3a}R^{3b})$ is $C(OH)_2$, X is —C(O)NHOCH$_3$, $(R^{yy})_n$ is 5-CH$_3$, and the combination of $R^1$ and W3 for a compound in each case corresponds to one line of Table B.

Table 191
Compounds of the formulae I-a, I-b, I-c and I-d in which the group $C(R^{3a}R^{3b})$ is C=O, X is —C(O)NH-c-C$_3$H$_5$, n=0, i.e. $(R^{yy})_n$ is absent, and the combination of $R^1$ and W3 for a compound in each case corresponds to one line of Table B.

Table 192
Compounds of the formulae I-a, I-b and I-d in which the group $C(R^{3a}R^{3b})$ is C=O, X is —C(O)NH-c-C$_3$H$_5$, $(R^{yy})_n$ is 5-F, and the combination of $R^1$ and W3 for a compound in each case corresponds to one line of Table B.

Table 193
Compounds of the formulae I-a, I-b and I-d in which the group $C(R^{3a}R^{3b})$ is C=O, X is —C(O)NH-c-C$_3$H$_5$, $(R^{yy})_n$ is 5-Cl, and the combination of $R^1$ and W3 for a compound in each case corresponds to one line of Table B.

Table 194
Compounds of the formulae I-a, I-b and I-d in which the group $C(R^{3a}R^{3b})$ is C=O, X is —C(O)NH-c-C$_3$H$_5$, $(R^{yy})_n$ is 5-CN, and the combination of $R^1$ and W3 for a compound in each case corresponds to one line of Table B.

Table 195
Compounds of the formulae I-a, I-b and I-d in which the group $C(R^{3a}R^{3b})$ is C=O, X is —C(O)NH-c-C$_3$H$_5$, $(R^{yy})_n$ is 5-CH$_3$, and the combination of $R^1$ and W3 for a compound in each case corresponds to one line of Table B.

Table 196
Compounds of the formulae I-a, I-b, I-c and I-d in which the group $C(R^{3a}R^{3b})$ is $C(OH)_2$, X is —C(O)NH-c-C$_3$H$_5$, n=0, i.e. $(R^{yy})_n$ is absent, and the combination of $R^1$ and W3 for a compound in each case corresponds to one line of Table B.

Table 197
Compounds of the formulae I-a, I-b, I-c and I-d in which the group $C(R^{3a}R^{3b})$ is $C(OH)_2$, X is —C(O)NH-c-C$_3$H$_5$, $(R^{yy})_n$ is 5-F, and the combination of $R^1$ and W3 for a compound in each case corresponds to one line of Table B.

Table 198
Compounds of the formulae I-a, I-b and I-d in which the group $C(R^{3a}R^{3b})$ is $C(OH)_2$, X is —C(O)NH-c-C$_3$H$_5$, $(R^{yy})_n$ is 5-Cl, and the combination of $R^1$ and W3 for a compound in each case corresponds to one line of Table B.

Table 199
Compounds of the formulae I-a, I-b and I-d in which the group $C(R^{3a}R^{3b})$ is $C(OH)_2$, X is —C(O)NH-c-C$_3$H$_5$, $(R^{yy})_n$ is 5-CN, and the combination of $R^1$ and W3 for a compound in each case corresponds to one line of Table B.

Table 200
Compounds of the formulae I-a, I-b and I-d in which the group $C(R^{3a}R^{3b})$ is $C(OH)_2$, X is —C(O)NH-c-C$_3$H$_5$, $(R^{yy})_n$ is 5-CH$_3$, and the combination of $R^1$ and W3 for a compound in each case corresponds to one line of Table B.

TABLE B

| No. | $R^1$ | W3 |
| --- | --- | --- |
| B-1 | n-Butyl | 1H-Benzo[d]imidozol-2-yl |
| B-2 | n-Butyl | Benzo[d]thiazol-2-yl |
| B-3 | n-Butyl | Benzo[d]oxazol-2-yl |
| B-4 | Isobutyl | 1H-Benzo[d]imidozol-2-yl |
| B-5 | Isobutyl | Benzo[d]thiazol-2-yl |
| B-6 | Isobutyl | Benzo[d]oxazol-2-yl |
| B-7 | Benzyl | 1H-Benzo[d]imidozol-2-yl |

TABLE B-continued

| No. | R¹ | W3 |
|---|---|---|
| B-8 | Benzyl | Benzo[d]thiazol-2-yl |
| B-9 | Benzyl | Benzo[d]oxazol-2-yl |
| B-10 | 4-Chlorobenzyl | 1H-Benzo[d]imidozol-2-yl |
| B-11 | 4-Chlorobenzyl | Benzo[d]thiazol-2-yl |
| B-12 | 4-Chlorobenzyl | Benzo[d]oxazol-2-yl |
| B-13 | 4-Methoxybenzyl | 1H-Benzo[d]imidozol-2-yl |
| B-14 | 4-Methoxybenzyl | Benzo[d]thiazol-2-yl |
| B-15 | 4-Methoxybenzyl | Benzo[d]oxazol-2-yl |
| B-16 | Cyclohexylmethyl | 1H-Benzo[d]imidozol-2-yl |
| B-17 | Cyclohexylmethyl | Benzo[d]thiazol-2-yl |
| B-18 | Cyclohexylmethyl | Benzo[d]oxazol-2-yl |
| B-19 | 2-Thienylmethyl | 1H-Benzo[d]imidozol-2-yl |
| B-20 | 2-Thienylmethyl | Benzo[d]thiazol-2-yl |
| B-21 | 2-Thienylmethyl | Benzo[d]oxazol-2-yl |
| B-22 | Pyridin-3-ylmethyl | 1H-Benzo[d]imidozol-2-yl |
| B-23 | Pyridin-3-ylmethyl | Benzo[d]thiazol-2-yl |
| B-24 | Pyridin-3-ylmethyl | Benzo[d]oxazol-2-yl |

The compounds of the invention of the general formula I and the required starting materials used to prepare them can be prepared in analogy to known processes of organic chemistry as are described in standard works of organic chemistry, e.g. Houben-Weyl, "Methoden der Organischen Chemie", Thieme-Verlag Stuttgart; Jerry March "Advanced Organic Chemistry", 5$^{th}$ edition, Wiley & Sons and the literature cited therein; and R. Larock, "Comprehensive Organic Transformations", 2$^{nd}$ edition, Weinheim 1999, and the literature cited therein. The compounds of the invention of the general formula I are advantageously prepared by the methods described below and/or in the experimental section.

In the following the variables R$^1$, R$^2$, W, and X exhibit the aforementioned meanings and the variable Y represents the diradical:

(Y)

in which n, R$^y$, Y$^1$, Y$^2$, Y$^3$ and Y$^4$ are as defined herein and wherein * indicates the point of attachment to W, while # indicates the point of attachment to the carbonyl group.

The synthesis of C-disubstituted hetaryl residues of the formula Y used as intermediates for preparation of compounds of the general formula I can be achieved as described in the standard works of heterocyclic chemistry, eg. J. Joule et al. "Heterocyclic Chemistry", Blackwell; and T. Eicher, S. Hauptmann "The Chemistry of Heterocycles", Wiley-VCH, 1$^{st}$ edition.

The compounds of formula I can be prepared in analogy to the schemes and methods described in WO 99/54305 and WO 2008/080969.

Scheme 1:

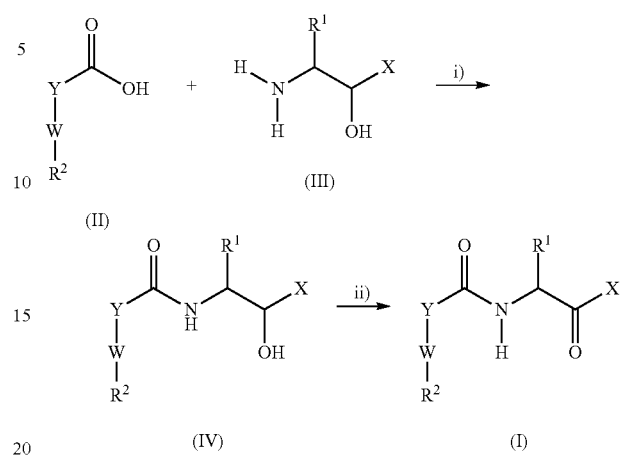

As shown in Scheme 1, in a first step i) a carboxylic acid II is converted by reaction with an amino alcohol III into a corresponding hydroxy amide IV. In this connection, conventional peptide coupling methods are ordinarily used, as are described for example in R. C. Larock, Comprehensive Organic Transformations, VCH Publisher, 1989, pages 972-976, or in Houben-Weyl, Methoden der organischen Chemie, 4th edition, E5, Chap. V. It may be advantageous firstly to activate the carboxylic acid II. For this purpose, for example, the carboxylic acid II is reacted with a carbodiimide such as dicyclohexylcarbodiimide (DCC) or 1-ethyl-3-(3-dimethylaminopropyl)carbodiimide (EDC) in the presence of hydroxybenzotriazole (HOBt), nitrophenol, pentafluorophenol, 2,4,5-trichlorophenol or N-hydroxysuccinimide, to obtain an activated ester IIa. It may further be advantageous to prepare the activated ester IIa in the presence of a base, for example a tertiary amine. The activated ester IIa is subsequently reacted with the amino alcohol of the formula III or its hydrohalide salt to give the hydroxy amide IV. The reaction normally takes place in anhydrous inert solvents, such as chlorinated hydrocarbons, e.g. dichloromethane or dichloroethane, ethers, e.g. tetrahydrofuran or 1,4-dioxane or carboxamides, e.g. N,N-dimethylformamide, N,N-dimethylacetamide or N-methylpyrrolidone. Step i) is ordinarily carried out at temperatures in the range from –20° C. to +25° C.

Subsequently, in a second step ii), the hydroxy amide compound IV is oxidized to the carboxamide compound I. Various conventional oxidation reactions are suitable for this (see R. C. Larock, Comprehensive Organic Transformations, VCH Publisher, 1989, page 604 et seq.) such as, for example, Swern oxidation and Swern analogous oxidations (T. T. Tidwell, Synthesis 1990, pp. 857-870) or Pfitzner-Moffatt oxidation. Suitable oxidizing agents are dimethyl sulfoxide (DMSO) in combination with dicyclohexylcarbodiimide or 1-ethyl-3-(3-dimethylaminopropyl)carbodiimide, dimethyl sulfoxide in combination with the pyridine-SO$_3$ complex or dimethyl sulfoxide in combination with oxalyl chloride, sodium hypochloride/TEMPO(S. L. Harbenson et al., J. Med: Chem. 1994, 37, 2918-2929), and hypervalent iodine reagents like 2-iodoxybenzoic acid (IBX) (J. Org. Chem. 1995, 60, 7272), the Dess-Martin reagent (J. Org. Chem. 1983, 48, 4155) or polymer-supported IBX (H.5 Jang, Tetrahedron Lett. 2007, 48, 3731-3734). Depending on the oxidizing agent used, the oxidation of the hydroxy amide compound IV takes place at temperatures of from –50 to +25° C.

Compounds of the formula IV in which X is —C(O)N(R$^{x4}$)—(C$_1$-C$_6$-alkylene)-NR$^{x2}$R$^{x3}$ or is —C(O)N(R$^{x4}$)NR$^{x2}$R$^{x3}$, in which R$^{x2}$, R$^{x3}$ and R$^{x4}$ have the aforementioned meanings, can additionally be prepared by reacting compounds of the formula III, in which X is COON, with hydrazine compounds of the formula NH(R$^{x4}$)NR$^{x2}$R$^{x3}$ or diamines of the formula NH(R$^{x4}$)—(C$_1$-C$_6$-alkylene)-NR$^{x2}$R$^{x3}$. The reaction can then be carried out in analogy to step i) in Scheme 1.

The amino alcohols III can be obtained by purchase or can be prepared by processes disclosed in the literature (for amino hydroxy carboxylic acid derivatives, see, for example, S. L. Harbenson et al., J. Med. Chem. 1994, 37, 2918-2929 or J. P. Burkhardt et al., Tetrahedron Lett. 1988, 29, 3433-3436) or by the methods and procedures described in WO 2008/08969.

The carboxylic acid II can be prepared by hydrolyzing the carboxylic ester V with acids or bases under generally customary conditions. The hydrolysis preferably takes place with bases such as alkali metal or alkaline earth metal hydroxides, for example lithium hydroxide, sodium hydroxide or potassium hydroxide in aqueous medium or in a mixture of water and organic solvents, e.g. alcohols such as methanol or ethanol, ethers such as tetrahydrofuran or dioxane, at room temperature or elevated temperature such as 25-100° C.

Scheme 2:

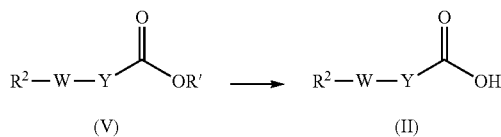

In formulae II and V, R$^2$, W and Y have the aforementioned meanings. In formula V, R' is alkyl, preferably C$_1$-C$_6$-alkyl.

In general carboxylic ester of the formula V can be prepared either using Suzuki or Stille reaction employing the appropriate starting materials as depicted in Scheme 3.

Scheme 3:

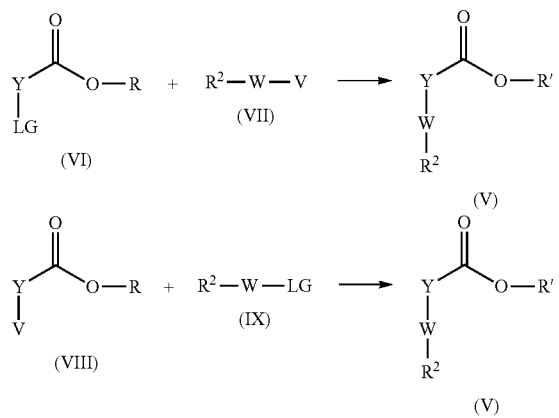

In Scheme 3, LG represents a group like halogen or triflate, which is known to be displaceable in metal-catalyzed reactions like Suzuki or Stille. The variable V represents the complementary group required for these reactions, like boronic acid or boronic ester in the case of Suzuki coupling, or organo stannyl compounds for the Stille reaction.

Suzuki coupling of appropriate phenyl or hetaryl boronic acids and boronic esters, respectively, is described e.g. 1) for thiazoles in T. Bach et al., Synlett 2002, 12, 2089-2091; Tetrahedron Lett. 2000, 41, 11, 1707-1710; WO 2003/2977 and WO 2005/19161; 2) for imidazoles in US 2003/220372 and WO 2003/93252; 3) for oxazoles in H. Araki et al., Synlett 2006, 4, 555-558; E. Flegau et al., Organic Letters 2006, 8, 12, 2495-2498. Stille coupling of appropriate stannyl organyls with halogenated phenyl- or hetaryl residues can be applied as described 1) for thiazoles in M. Wentland et al., J. Med. Chem. 1993, 36, 11, 1580-1596; J. Haemmerle et al., Synlett 2007, 19, 2975-2978, and 2) for oxazoles in Kelly et al., Tetrahedron Lett. 1995, 36, 30, 5319-5322.

Alternatively compounds of the general formula V can be prepared by directly assembling the hetaryl residue W starting from appropriate precursors as outlined below.

In cases where W represents a radical W1 or W2 with Q=S or where W—R$^2$ represents a radical W3 with Q=S the appropriate starting materials of the formulae VII or IX can either be purchased or prepared by methods already mentioned. A general overview for the synthesis of substituted thiazoles can be found in e.g. G. Vernin, in: "Chemistry of Heterocyclic Compounds" 1979, 34, 165-335; Houben-Weyl, "Methoden der Organischen Chemie", Vol. E8, Hetarenes III Part 2, Thieme-Verlag Stuttgart; or J. V. Metzger, in: "Comprehensive Heterocyclic Chemistry" A. R. Katritzky, C. W. Rees, Eds., Pergamon Press, New York, 1984, Vol. 6, pp 235-332.

The compounds of the formula V where W is W1, W2 or where W together with R$^2$ is W3, with Q in each case being S, are particularly advantageously prepared by the method originally disclosed by Hantzsch (A. Hantzsch, J. H. Weber, Ber. Dtsch. Chem. Ges. 1887, 20, 3118), in which alpha-halo or alpha-hydroxy ketones are reacted with thioamides to give the corresponding thiazoles V according to the reaction conditions described in the experimental section.

In the case where W represents a radical W1, W2 or together with R$^2$ a radical W3, with Q in each case being NH, the appropriate starting materials can either be purchased or prepared by methods as already mentioned. A general overview for the synthesis of substituted imidazoles can be found in Houben-Weyl "Methoden der Organischen Chemie", Vol. E8, Hetarenes III Part 3, Thieme-Verlag, Stuttgart; and M. R. Grimmett, Advances in Heterocyclic Chemistry 1970, 12, 103-83.

Phenyl- or hetaryl substituted imidazole compounds of the formula II with Q=NH are particularly advantageously prepared by a method disclosed in WO 2005/002503 and CA2027347A1, which is depicted in Scheme 4 with Y represented by phenyl as an example: 3-Imino-2,3-dihydro-1H-isoindol-1-one is converted into 2-substituted 3-imino-2-(2-oxo-2-ethyl)-2,3-dihydro-1H-isoindol-1-one by alkylation with an alpha-halo-ketone, which upon basic treatment rearranges to the corresponding 4-substituted 2-(-1H-imidazol-2-yl)benzoic acid.

Scheme 4:

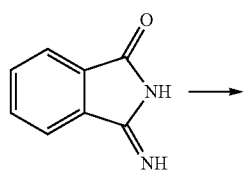

-continued

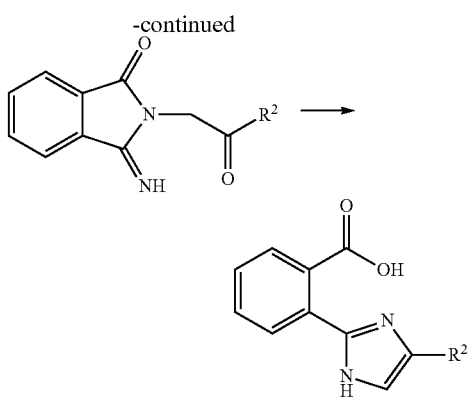

In the case where W represents a radical W1, W2 or together with $R^2$ a radical W3, with Q in each case being 0, the appropriate starting materials can either be purchased or prepared by methods as already mentioned. A general overview for the synthesis of substituted oxazoles can be found in Houben-Weyl "Methoden der Organischen Chemie", Vol. E8, Hetarenes III Part 1, Thieme-Verlag, Stuttgart; or D. C. Palmer, Ed. "Oxazoles: The Chemistry of Heterocyclic compounds", Part A, Vol. 60, Wiley, New York, 2003.

According to one aspect of the invention the hydrogen atom linked to the carbon atom carrying the radical $R^1$ of a compound I is replaced by a deuterium atom, as shown in formula I-D below. $R^1$, $R^2$, $R^{3a}$, $R^{3b}$, $Y^1$, $Y^2$, $Y^3$, $Y^4$, W and X in formula I-D have the aforementioned meanings.

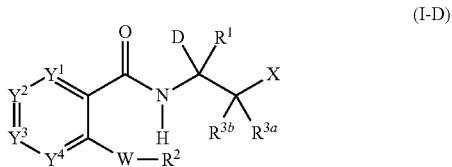
(I-D)

Compounds of formula I-D can be prepared in analogy to methods described by F. Maltais et al., J. Med. Chem. 2009, 52 (24), 7993-8001 (DOI 10.1021/jm901023f). The degree of deuteration at said position usually exceeds 80%, preferably exceeds 90% and inparticular exceeds 95%. The deuterated compounds of formula I-D often show a markedly higher stability against racematisation than their counterparts of formula I, probably due to a kinetic isotope effect (see F. Maltais et al., J. Med. Chem. 2009, 52 (24), 7993-8001).

The reaction mixtures are worked up in a conventional way, e.g. by mixing with water, separating the phases and, where appropriate, purifying the crude products by chromatography. The intermediates and final products in some cases result in the form of colorless or pale brownish, viscous oils which are freed of volatiles or purified under reduced pressure and at moderately elevated temperature. If the intermediates and final products are obtained as solids, the purification can also take place by recrystallization or digestion.

If individual compounds I are not obtainable by the routes described above, they can be prepared by derivatization of other compounds I.

The compounds of the invention exhibit extremely low Ki values in relation to the inhibition of calpain and thus permit efficient inhibition of calpain, especially calpain I, at low serum levels. The compounds of the invention ordinarily exhibit Ki values in relation to the inhibition of calpain in vitro of <500 nM, in particular <100 nM and specifically ≤40 nM. The compounds of the invention are therefore particularly suitable for the treatment of disorders associated with an elevated calpain activity.

In addition, the compounds of the invention are selective calpain inhibitors, i.e. the inhibition of other cysteine proteases such as cathepsin B, cathepsin K, cathepsin L or cathepsin S takes place only at concentrations which are distinctly higher than the concentrations necessary for inhibition of calpain. Accordingly, the compounds of the invention ought to show distinctly fewer side effects than the prior art compounds which are comparatively unselective in relation to inhibition of calpain and likewise inhibit other cysteine proteases.

Compounds preferred according to the invention accordingly have a selectivity in relation to inhibition of cathepsin B, expressed in the form of the ratio of the Ki for inhibition of cathepsin B to the Ki for inhibition of calpain of ≥10, in particular ≥30.

Compounds preferred according to the invention accordingly have a selectivity in relation to inhibition of cathepsin K, expressed in the form of the ratio of the Ki for inhibition of cathepsin K to the Ki for inhibition of calpain of ≥10, in particular ≥30.

Compounds preferred according to the invention accordingly have a selectivity in relation to inhibition of cathepsin L, expressed in the form of the ratio of the Ki for inhibition of cathepsin L to the Ki for inhibition of calpain of ≥30, in particular ≥50.

Compounds preferred according to the invention accordingly have a selectivity in relation to inhibition of cathepsin S, expressed in the form of the ratio of the Ki for inhibition of cathepsin S to the Ki for inhibition of calpain of ≥50, in particular ≥100.

In addition, the compounds of the present invention feature an improved stability in the cytosole of human cells, which markedly contributes to their good overall metabolic stability. The cytosolic stability can be measured for example by incubating a solution of a compound of the invention with liver cytosole from particular species (for example rat, dog, monkey or human) and determining the half-life of the compound under these conditions. It is possible to conclude from larger half-lives that the metabolic stability of the compound is improved. The stability in the presence of human liver cytosole is of particular interest because it makes it possible to predict the metabolic degradation of the compound in the human liver. Compounds with enhanced cytosolic stability therefore are likely to be degraded at reduced rates in the liver. Slower metabolic degradation in the liver in turn can lead to higher and/or longer-lasting concentrations (effective levels) of the compound in the body, so that the elimination half-life of the compounds of the invention is increased. Increased and/or longer-lasting effective levels may lead to a better efficacy of the compound in the treatment or prophylaxis of various calpain-dependent diseases. An improved metabolic stability may additionally lead to an increased bioavailability after oral administration, because the compound is subjected, after being absorbed in the intestine, to less metabolic degradation in the liver (termed the first pass effect). An increased oral bioavailability may, because the concentration (effective level) of the compound is increased, lead to a better efficacy of the compound after oral administration.

Accordingly, due to their improved cytosolic stability the compounds of the invention remain in the cytosol for extended periods, i.e. have a decreased cytosolic clearance, and therefore ought to show enhanced human pharmacokinetics.

Compounds preferred according to the invention accordingly have a cytosolic clearance in human liver cytosol of ≤30 μl/min/mg, in particular of ≤15 μl/min/mg.

The improved cytosolic stability of the compounds according to the present invention is probably primarily due to their reduced susceptibility to aldo-keto reductases (AKRs) which mediate the metabolic degradation of compounds having a carbonyl group in the liver cytosole of humans and monkeys. Thus, the AKR-catalyzed reduction of the ketoamides of formula I should be less pronounced than that of less stable ketoamides. Hence, the ratio of the concentration of the parent compound, i.e. the ketamide of formula I, to the concentration of the metabolite, i.e. the hydroxyamide stemming form the ketoamide, is a measure for the stability of the compounds of the invention.

Compounds preferred according to the invention accordingly have, after an incubation in human hepatocytes for 4 hours, a concentration ratio of the hydroxyamide metabolite to their corresponding parent compound of formula I of ≤5, in particular ≤2 and specifically ≤0.5.

Owing to their inhibitory effect on calpain and their selectivity for calpain by comparison with other cysteine proteases, the compounds of the invention of the formula I, their tautomers and their pharmaceutically suitable salts are particularly suitable for the treatment of a disorder, of an impairment or of a condition which is associated with an elevated calpain activity as are described for example in the prior art cited at the outset.

Disorders, impairments or conditions associated with an elevated calpain activity are in particular neurodegenerative disorders, especially those neurodegenerative disorders occurring as a result of a chronic brain supply deficit, of an ischemia (stroke) or of a trauma such as brain trauma, and the neurodegenerative disorders Alzheimer's disease, Parkinson's disease, amyotrophic lateral sclerosis and Huntington's disease, also multiple sclerosis and the damage to the nervous system associated therewith, especially damage to the optic nerve (optic neuritis) and the nerves which control the movement of the eye. Accordingly, preferred embodiments of the invention relate to the treatment of neurodegenerative disorders, especially of the aforementioned neurodegenerative disorders in humans, and to the use of the compounds of the invention of the formula I, their tautomers and their pharmaceutically suitable salts for the manufacture of a medicament for the treatment of these disorders.

Disorders, impairments or conditions associated with an elevated calpain activity also include epilepsy. Accordingly, preferred embodiments of the invention relate to the treatment of epilepsy in humans, and to the use of the compounds of the invention of the formula I, their tautomers and their pharmaceutically suitable salts for the manufacture of a medicament for the treatment of epilepsy.

The disorders, impairments or conditions associated with an elevated calpain activity also include pain and painful conditions. Accordingly, preferred embodiments of the invention relate to the treatment of pain and painful conditions in mammals, especially in humans, and to the use of the compounds of the invention of the formula I, their tautomers and their pharmaceutically suitable salts for the manufacture of a medicament for the treatment of pain and painful conditions.

The disorders, impairments or conditions associated with an elevated calpain activity also include damage to the heart following cardiac ischemias, damage to the kidneys following renal ischemias, skeletal muscle damage, muscular dystrophies, damage arising through proliferation of smooth muscle cells, coronary vasospasms, cerebral vasospasms, macular degeneration, cataracts of the eyes, or restenosis of blood vessels following angioplasty. Accordingly, preferred embodiments of the invention relate to the treatment of diseases or conditions associated with damage to the heart following cardiac ischemias, damage to the kidneys following renal ischemias, skeletal muscle damage, muscular dystrophies, damage arising through proliferation of smooth muscle cells, coronary vasospasms, cerebral vasospasms, macular degeneration, cataracts of the eyes, or restenosis of blood vessels following angioplasty in mammals, especially in humans, and to the use of the compounds of the invention of the formula I, their tautomers and their pharmaceutically suitable salts for the manufacture of a medicament for the treatment of these disorders.

It has further emerged that inhibition of calpain brings about cytotoxic effects on tumor cells. Accordingly, the compounds of the invention are suitable for the chemotherapy of tumors and metastasis thereof. Preferred embodiments of the invention therefore relate to the use of the compounds of the invention of the formula I, their tautomers and their pharmaceutically suitable salts in the therapy of tumors and metastases, and to their use for the manufacture of a medicament for the therapy of tumors and metastases.

It has further been found that various impairments associated with an HIV disorder, especially nerve damage (HIV-induced neurotoxicity), are mediated by calpain and therefore inhibition of calpain allows such impairments to be treated or alleviated. Accordingly, the compounds of the invention of the formula I, their tautomers and their pharmaceutically suitable salts are suitable for the treatment of HIV patients. Preferred embodiments of the invention therefore relate to the use of the compounds of the invention of the formula I, their tautomers and their pharmaceutically suitable salts for the treatment of HIV-infected patients, especially the treatment of those impairments caused by an HIV-induced neurotoxicity, and to their use for the manufacture of a medicament for the treatment of HIV patients.

It has further been found that the release of interleukin-1, TNF or beta-amyloid peptides (Aβ or Aβ-peptides) can be reduced or completely inhibited by calpain inhibitors. Accordingly, impairments or disorders associated with an elevated interleukin-1, TNF or Aβ level can be treated by using the compounds of the invention of the formula I, their tautomers and their pharmaceutically suitable salts. Preferred embodiments of the invention therefore relate to the use of the compounds of the invention of the formula I, their tautomers, their produgs and their pharmaceutically acceptable salts for the treatment of impairments or disorders associated with an elevated interleukin-1, TNF or Aβ level such as rheumatism, rheumatoid arthritis and to their use for the manufacture of a medicament for the treatment of such impairments or disorders.

The compounds of the general formula (I) are distinguished in particular also by a good metabolic stability. The metabolic stability of a compound can be measured for example by incubating a solution of this compound with liver microsomes from particular species (for example rat, dog or human) and determining the half-life of the compound under these conditions (R S Obach, Curr Opin Drug Discov Devel. 2001, 4, 36-44). It is possible to conclude from larger half-lives that the metabolic stability of the compound is improved. The stability in the presence of human liver microsomes is of particular interest because it makes it possible to predict the metabolic degradation of the compound in the human liver. Compounds with increased metabolic stability are therefore probably also degraded more slowly in the liver (measured in the liver microsome test). Slower metabolic degradation in the liver can lead to higher and/or longer-lasting concentrations (effective levels) of the compound in the body, so that the elimination half-life of the compounds of the invention is increased. Increased and/or longer-lasting effective levels may lead to a better efficacy of the compound in the treatment or prophylaxis of various calpain-dependent diseases. An improved metabolic stability may additionally lead to an increased bioavailability after oral administration, because the compound is subjected, after being absorbed in the intestine, to less metabolic degradation in the liver (termed the first pass effect). An increased oral bioavailability may, because the concentration (effective level) of the compound is increased, lead to a better efficacy of the compound after oral administration.

The compounds of the invention of the formula I are further distinguished by exhibiting an improved pharmacological activity, compared with the carboxamide compounds of the formula I disclosed in the prior art, in patients or relevant animal models allowing prognostic statements for use in treatment.

The present invention also relates to pharmaceutical compositions (i.e. medicaments) which comprise at least one compound of the invention of the formula I or a tautomer or a pharmaceutically suitable salt thereof and, where appropriate, one or more suitable excipients/drug carriers.

These drug carriers/excipients are chosen according to the pharmaceutical form and the desired mode of administration.

The compounds of the invention of the general formula I, their tautomers and the pharmaceutically suitable salts of these compounds can be used to manufacture pharmaceutical compositions for oral, sublingual, subcutaneous, intramuscular, intravenous, topical, intratracheal, intranasal, transdermal or rectal administration, and be administered to animals or humans in unit dose forms, mixed with conventional pharmaceutical carriers, for the prophylaxis or treatment of the above impairments or diseases.

Suitable unit dose forms include forms for oral administration, such as tablets, gelatin capsules, powders, granules and solutions or suspensions for oral intake, forms for sublingual, buccal, intratracheal or intranasal administration, aerosols, implants, forms of subcutaneous, intramuscular or intravenous administration and forms of rectal administration.

The compounds of the invention can be used in creams, ointments or lotions for topical administration.

In order to achieve the desired prophylactic or therapeutic effect, the dose of the active basic ingredient may vary between 0.01 and 50 mg per kg of body weight and per day.

Each unit dose may comprise from 0.05 to 5000 mg, preferably 1 to 1000 mg, of the active ingredient in combination with a pharmaceutical carrier. This unit dose can be administered 1 to 5 times a day, so that a daily dose of from 0.5 to 25 000 mg, preferably 1 to 5000 mg, is administered.

If a solid composition is prepared in the form of tablets, the main ingredient is mixed with a pharmaceutical carrier such as gelatin, starch, lactose, magnesium stearate, talc, silicon dioxide or the like.

The tablets may be coated with sucrose, a cellulose derivative or another suitable substance or be treated otherwise in order to display a prolonged or delayed activity and in order to release a predetermined amount of the active basic ingredient continuously.

A preparation in the form of gelatin capsules is obtained by mixing the active ingredient with an extender and taking up the resulting mixture in soft or hard gelatin capsules.

A preparation in the form of a syrup or elixir or for administration in the form of drops may comprise active ingredients together with a sweetener, which is preferably calorie-free, methylparaben or propylparaben as antiseptics, a flavoring and a suitable coloring.

The water-dispersible powders or granules may comprise the active ingredients mixed with dispersants, wetting agents or suspending agents such as polyvinylpyrrolidones, and sweeteners or taste improvers.

Rectal administration is achieved by the use of suppositories which are prepared with binders which melt at the rectal temperature, for example cocobutter or polyethylene glycols. Parenteral administration is effected by using aqueous suspensions, isotonic salt solutions or sterile and injectable solutions which comprise pharmacologically suitable dispersants and/or wetting agents, for example propylene glycol or polyethylene glycol.

The active basic ingredient may also be formulated as microcapsules or liposomes/centrosomes, if suitable with one or more carriers or additives.

In addition to the compounds of the general formula I, their tautomers or their pharmaceutically suitable salts, the compositions of the invention may comprise further active basic ingredients which may be beneficial for the treatment of the impairments or diseases indicated above.

The present invention thus further relates to pharmaceutical compositions in which a plurality of active basic ingredients are present together, where at least one thereof is a compound of the invention.

The compounds of the invention also include those compounds in which one or more atoms have been replaced by their stable, non-radioactive isotopes, for example, a hydrogen atom by deuterium.

Stable isotopes (e.g., deuterium, $^{13}C$, $^{15}N$, $^{18}O$) are nonradioactive isotopes which contain one additional neutron than the normally abundant isotope of the respective atom. Deuterated compounds have been used in pharmaceutical research to investigate the in vivo metabolic fate of the compounds by evaluation of the mechanism of action and metabolic pathway of the non deuterated parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., J. *Labelled Comp. Radiopharmaceut.*, 36(10):927-932 (1995); Kushner et al., *Can. J. Physiol. Pharmacol.*, 77, 79-88 (1999)).

Incorporation of a heavy atom particularly substitution of deuterium for hydrogen, can give rise to an isotope effect that could alter the pharmacokinetics of the drug. This effect is usually insignificant if the label is placed at a metabolically inert position of the molecule.

Stable isotope labeling of a drug can alter its physicochemical properties such as pKa and lipid solubility. These changes may influence the fate of the drug at different steps along its passage through the body. Absorption, distribution, metabolism or excretion can be changed. Absorption and distribution are processes that depend primarily on the molecular size and the lipophilicity of the substance. These effects and alterations can affect the pharmacodynamic response of the drug molecule if the isotopic substitution affects a region involved in a ligand-receptor interaction.

Drug metabolism can give rise to large isotopic effect if the breaking of a chemical bond to a deuterium atom is the rate limiting step in the process. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. In any reaction in which the breaking of this bond is the rate limiting step, the reaction will proceed slower for the molecule with the heavy isotope due to "kinetic isotope effect". A reaction involving breaking a C-D bond can be up to 700 percent slower than a similar reaction involving breaking a C—H bond. If the C-D bond is not involved in any of the steps leading to the metabolite, there may not be any effect to alter the behavior of the drug. If a deuterium is placed at a site involved in the metabolism of a drug, an isotope effect will be observed only if breaking of the C-D bond is the rate limiting step. There is evidence to suggest that whenever cleavage of an aliphatic C—H bond occurs, usually by oxidation catalyzed by a mixed-function oxidase, replacement of the hydrogen by deuterium will lead to observable isotope effect. It is also important to understand that the incorporation of deuterium at the site of metabolism slows its rate to the point where another metabolite produced by attack at a carbon atom not substituted by deuterium becomes the major pathway a process called "metabolic switching".

Deuterium tracers, such as deuterium-labeled drugs and doses, in some cases repeatedly, of thousands of milligrams of deuterated water, are also used in healthy humans of all ages, including neonates and pregnant women, without reported incident (e.g. Pons G and Rey E, Pediatrics 1999 104: 633; Coward W A et al., Lancet 1979 7: 13; Schwarcz H P, Control. Clin. Trials 1984 5(4 Suppl): 573; Rodewald L E et al., J. Pediatr. 1989 114: 885; Butte N F et al. Br. J. Nutr. 1991 65: 3; MacLennan A H et al. Am. J. Obstet Gynecol. 1981 139: 948). Thus, it is clear that any deuterium released, for instance, during the metabolism of compounds of this invention poses no health risk.

The weight percentage of hydrogen in a mammal (approximately 9%) and natural abundance of deuterium (approximately 0.015%) indicates that a 70 kg human normally contains nearly a gram of deuterium. Furthermore, replacement of up to about 15% of normal hydrogen with deuterium has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci 1960 84: 736; Czakja D Metal., Am. J. Physiol. 1961 201: 357). Higher deuterium concentrations, usually in excess of 20%, can be toxic in animals. However, acute replacement of as high as 15%-23% of the hydrogen in humans' fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Increasing the amount of deuterium present in a compound above its natural abundance is called enrichment or deuterium-enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %.

The hydrogens present on a particular organic compound have different capacities for exchange with deuterium. Certain hydrogen atoms are easily exchangeable under physiological conditions and, if replaced by deuterium atoms, it is expected that they will readily exchange for protons after administration to a patient. Certain hydrogen atoms may be exchanged for deuterium atoms by the action of a deuteric acid such as $D_2SO_4/D_2O$. Alternatively, deuterium atoms may be incorporated in various combinations during the synthesis of compounds of the invention. Certain hydrogen atoms are not easily exchangeable for deuterium atoms. However, deuterium atoms at the remaining positions may be incorporated by the use of deuterated starting materials or intermediates during the construction of compounds of the invention.

Deuterated and deuterium-enriched compounds of the invention can be prepared by using known methods described in the literature. Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure. Relevant procedures and intermediates are disclosed, for instance in Lizondo, J et al., *Drugs Fut*, 21(11), 1116 (1996); Brickner, S J et al., *J Med Chem*, 39(3), 673 (1996); Mallesham, B et al., *Org Lett*, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; 20090082471, the methods are hereby incorporated by reference.

The following examples illustrate the invention without restricting it. Depending on the management of the reaction and work up, the compounds of the general formula I result as mixtures of carbonyl form and the corresponding hydrates. Conversion into the pure carbonyl compounds generally takes place by treating the substances with HCl in an inert solvent.

EXAMPLES

Preparation Examples

Example 1

N-(4-Amino-3,4-dioxo-1-phenylbutan-2-yl)-2-(1H-benzimidazol-2-yl)pyridine-3-carboxamide 1.1 2-(1H-Benzo[d]imidazol-2-yl)nicotinic acid A mixture of furo[3,4-b]pyridine-5,7-dione (2.0 g, 13.41 mmol) and benzene-1,2-diamine (1.45 g, 13.41 mmol) in 20 ml of N,N-dimethylformamide (DMF) was heated to 100° C. for 3 hours. The reaction mixture was evaporated to dryness, the obtained residue taken up in 15 mL of dichloromethane and stirred for 30 minutes at 5° C. Filtration with suction and drying gave 1.0 g of a red solid, which was used further without additional purification.

ESI-MS $[m+H]^+=240.1$.

1.2 (4-Amino-3-hydroxy-4-oxo-1-phenylbutan-2-yl)-2-(1H-benzo[d]imidazol-2-yl)nicotinamide 0.2 g N-(3-Dimethylaminopropyl)-N'-ethylcarbodiimide hydrochloride (EDC), 1.04 g 1-hydroxybenzotriazole hydrate and 150 µL triethylamine (Et$_3$N) were successively added to a solution of 2-(1H-benzo[d]imidazol-2-yl)nicotinic acid (0.2 g. 0.836 mmol) and 3-amino-2-hydroxy-4-phenylbutanamide (170 mg, 0.875 mmol) in 40 ml of dichloromethane at 5° C., and the mixture was stirred at 5° C. for about 5 minutes. A pH of 8-9 was adjusted by adding of 50 µl Et$_3$N, the mixture stirred for 1 hour at 5° C. and then overnight at room temperature. For work up the reaction mixture was evaporated to dryness, treated with 50 ml of water, the precipitate filtered off with suction, washed three times with water and dried at 50° C. over night. The crude product was purified by crystallization from 10 ml of 2-propanole yielding 50 mg of the title compound as white amorphous solid.

ESI-MS [m+H]$^+$=416.2.

1.3 N-(4-Amino-3,4-dioxo-1-phenylbutan-2-yl)-2-(1H-benzimidazol-2-yl)pyridine-3-carboxamide 160 mg of EDC and 36 µL of 2,2-dichloroacetic acid were added to 42 mg N-(4-amino-3-hydroxy-4-oxo-1-phenylbutan-2-yl)-2-(1H-benzo[d]imidazol-2-yl)nicotinamide (0.096 mmol) in 2 ml of dry dimethylsulfoxide (DMSO), and the reaction mixture stirred for 25 minutes at room temperature. For work up the reaction mixture was mixed with 40 ml of NaCl solution and sat. NaHCO$_3$ (1:1) for 10 minutes. The resulting solid was filtered off with suction, washed with water and dried. 24 mg of the title compound were obtained as lightgrey amorphous solid.

ESI-MS [m+H]$^+$=414.1.
$^1$H-NMR (500 MHz DMSO) δ ppm 13.0 (s broad, 1H), 9.55 (m, 1H), 8.78 (m, 2H), 8.02 (s, 1H), 7.81 (m, 1H), 7.6-7.5 (m, 3H), 7.3-6.90 (m, 6H), 5.51 (m, 1H), 3.21 (m, partially superimposed by water), 3.06 (m, 1H).

Example 2

N-(4-Amino-3,4-dioxo-1-phenylbutan-2-yl)-2-(5-phenyl-1H-imidazol-2-yl)pyridine-3-carboxamide

2.1 7-Imino-6-(2-oxo-2-phenylethyl)-6,7-dihydro-5H-pyrrolo[3,4-b]pyridin-5-one To a suspension of 7-imino-6,7-dihydro-5H-pyrrolo[3,4-b]pyridin-5-one (147 mg, 1 mmol) and 2-bromoacetephenone (219 mg, 1.1 mmol) in 3 ml of acetone K$_2$CO$_3$ (276 mg, 2.0 mmol) and KI (100 mg, 0.60 mmol) were added, and the mixture stirred over night. After filtration the mother liquor was evaporated to dryness, the obtained residue was treated with 30 ml of methyl-tert.-butylether, filtrated and dried to give 140 mg of the title compound as amorphous solid.

$^1$H-NMR (500 MHz DMSO) δ ppm 9.96 (s, 1H), 9.02 (dd, 1H), 8.34 (dd, 1H), 8.1 (m, 2H), 7.81 (dd, 1H), 7.74 (m, 1H), 7.61 (m, 2H), 5.35 (s, 2H).

2.2 2-(5-Phenyl-1H-imidazol-2-yl)nicotinic acid

To the suspension of 7-imino-6-(2-oxo-2-phenylethyl)-6,7-dihydro-5H-pyrrolo[3,4-b]pyridin-5-one (825 mg, 3.11 mmol) in 1N NaOH (6.22 ml) 40 ml of water were added, and the reaction mixture heated to reflux for 1.5 hours. After cooling to room temperature the mixture was diluted with 100 ml of water, and the pH adjusted to 2-3 by addition of 2N HCl. The resulting precipitate was filtered off and dried to give 414 mg of the title compound as solid; ESI-MS [M+W]: 266.1.

$^1$H-NMR (500 MHz DMSO) δ ppm 14.01 (s broad), 8.81 (dd, 1H), 8.48 (dd, 1H), 7.94 (s, 1H), 7.85 (m, 1H), 7.83 (m, 1H), 7.59 (dd, 1H), 7.46 (m, 2H), 7.32 (m, 1H).

2.3 N-(4-Amino-3-hydroxy-4-oxo-1-phenylbutan-2-yl)-2-(5-phenyl-1H-imidazol-2-yl)nicotinamide Coupling of 2-(5-phenyl-1H-imidazol-2-yl)nicotinic acid (200 mg, 0.754 mmol) and 3-amino-2-hydroxy-4-phenylbutanamide (161 mg, 0.829 mmol) in a manner analogous to example 1.2 afforded 142 mg of crude product, which was purified by chromatography on silica gel (eluent: CH$_2$Cl$_2$+0-20% methanol). After evaporation of the combined product fractions the remaining oil was treated with water, the resulting precipitate filtered off and dried to give 55 mg of the title compound.

ESI-MS [M+H]$^+$: 442.2.

2.4 N-(4-Amino-3,4-dioxo-1-phenylbutan-2-yl)-2-(5-phenyl-1H-imidazol-2-yl)nicotinamide To a solution of N-(4-amino-3-hydroxy-4-oxo-1-phenylbutan-2-yl)-2-(5-phenyl-1H-imidazol-2-yl)nicotinamide (60 mg, 0.136 mmol) in a mixture of 2 ml of DMSO and 10 ml of dichloromethane IBX-polystyrene was added (371 mg, 0.408 mmol), and the reaction mixture stirred for 16 hours at room temperature. The polymer was filtered off, washed with dichloromethane, the combined organic layers washed with water, dried and evaporated to dryness. The remaining oily residue was treated with water to give a yellow solid which was filtered off and dried again. To a solution of the obtained solid in 20 ml of ethylacetate (EtOAc) two drops of 4N HCl in dioxane were added, and the resulting precipitate filtered off. Recrystallisation of the crude product from 15 ml of ethylacetate yielded 31 mg of the title compound as solid.

ESI-MS [M+H$_2$O+H]$^+$: 458.2.
$^1$H-NMR (500 MHz DMSO) δ ppm 9.55 (m, 1H), 8.86 (m, 1H), 8.04 (m, 2H), 7.85 (m, 2H), 7.74 (m, 1H), 7.46 (m, 2H), 7.38 (m, 1H), 7.25-7.11 (m, 6H), 5.50 (m, 1H), 3.7 and 2.90 (each dd, 1H).

Example 3

N-(4-Amino-3,4-dioxo-1-phenylbutan-2-yl)-2-(1,3-benzothiazol-2-yl)pyridine-3-carboxamide

3.1 N-(4-Amino-3-hydroxy-4-oxo-1-phenylbutan-2-yl)-2-(1,3-benzothiazol-2-yl)pyridine-3-carboxamide 0.58 g 1-Hydroxybenzotriazole hydrate, 0.75 ml diisopropylethylamin (DIPEA) and 0.82 g EDC successively were added to a solution of 2-(1,3-benzothiazol-2-yl)benzoic acid (1.0 g, 3.90 mmol) in a mixture of 1.5 ml DMF und 20 ml THF at 5° C., and stirred at 5° C. for 1 hour. 3-Amino-2-hydroxy-4-phenylbutanamide (0.8 g, 3.9 mmol) was added, and the reaction mixture stirred for 1 hour at 5° C. and then over night at room temperature. For work up water was added under cooling, the precipitate formed filtered off with suction and dried to give 1.33 g of the title compound.

ESI-MS [M+H]$^+$=433.3.

3.1 N-(4-Amino-3,4-dioxo-1-phenylbutan-2-yl)-2-(1,3-benzothiazol-2-yl)pyridine-3-carboxamide To a solution of N-(4-Amino-3-hydroxy-4-oxo-1-phenylbutan-2-yl)-2-(1,3-benzothiazol-2-yl)pyridine-3-carboxamide (0.5 g, 1.16 mmol) in 1.5 ml of DMSO und 15 ml of dichloromethane 3.04 g N-cyclohexylcarbodiimid-N'-methylpolystyrole (1.9 mmol/g; 5.78 mmol) and 0.24 ml dichloroacetic acid (0.38 g, 2.89 mmol) were added, and the reaction mixture stirred over night at room temperature. For work up the polymer was filtered off, washed with dichloromethane, and the combined organic layers evaporated to dryness. Treatment with a mixture of n-hexane/ethylacetate, filtration and drying afforded 260 mg of the title compound, as white amorphous solid:

ESI-MS [M+H$^+$]=431.04.

¹H-NMR (400 MHz DMSO) δ ppm: 9.06 (d, 1H), 8.74 (d, 1H), 8.12 (d, 1H), 8.05 (s, 1H), 7.81 (d, 2H), 7.68 (d, 1H), 7.60 (dd, 1H), 7.48 (m, 2H), 7.26 (d, 2H), 7.07-7.18 (m, 3H), 5.53-5.59 (m, 1H), 3.20 (dd, 1H), 2.94 (dd, 1H).

Example 4

N-(4-Amino-3,4-dioxo-1-phenylbutan-2-yl)-2-[4-(4-fluorophenyl)-1,3-thiazol-2-yl]pyridine-3-carboxamide 4.1 Ethyl 2-carbamothioylnicotinate Et$_3$N (10 ml) was added to a solution of ethyl 2-cyanonicotinate (1.9 g, 10.78 mmol) in 20 ml of pyridine. Hydrogen sulfide was passed through the reaction mixture at 5° C. for 20 minutes, then the mixture was stirred for 1 hour at room temperature. For work up the solution was purged with nitrogen for 30 minutes, evaporated to dryness, and the remaining solid dissolved in 200 ml of dichloromethane. The organic layer was washed successively with water and brine, dried, evaporated and treated with ethylacetate to give 2.15 g of a red oil which was reacted without further purification.
ESI-MS [M+H]$^+$: 211.1.

4.2 Ethyl 2-(4-(4-fluorophenyl)thiazol-2-yl)nicotinate

To a suspension of ethyl 2-carbamothioylnicotinate (1.9 g, 9.04 mmol) in 20 ml of DMF 4-fluorophenacylbromide (2.0 g, 9.22 mmol) was added, and the resulting mixture stirred for 2 hours at room temperature. The mixture was filtered under suction, the mother liquor evaporated to dryness, and the remaining oil purified by chromatography on silica gel (eluent: CH$_2$Cl$_2$+0-5% methanol) to give 434 mg of the title compound as amorphous solid.
ESI-MS [M+H]$^+$: 329.1.

4.3 2-(4-(4-Fluorophenyl)thiazol-2-yl)nicotinic acid 3 ml of a 2N NaOH solution were added to a solution of ethyl 2-(4-(4-fluorophenyl)thiazol-2-yl)nicotinate (430 mg, 1.31 mmol) in 25 ml of methanol, and afterwards stirred for 2 hours at 60° C. The reaction mixture was subsequently evaporated to dryness, mixed with water and neutralized by adding 2N HCl. Filtration with suction and drying the precipitate formed resulted in 356 mg of the acid as yellow amorphous solid.
ESI-MS [M+H]$^+$: 301.05.

4.4 N-(4-Amino-3-hydroxy-4-oxo-1-phenylbutan-2-yl)-2-(4-(4-fluorophenyl)thiazol-2-yl)nicotinamide Coupling of 2-(4-(4-fluorophenyl)thiazol-2-yl)nicotinic acid (356 mg, 1.185 mmol) and 3-amino-2-hydroxy-4-phenylbutanamide (280 mg, 1.442 mmol) in an analogous manner as described for example 1.2 afforded 530 mg of the title compound as white amorphous solid.
ESI-MS [M+H]$^+$: 477.2.
¹H-NMR (500 MHz DMSO) δ ppm 8.69 (m, 1H), 8.22 (m, 2H), 8.01 (m, 2H), 7.71 (m, 1H), 7.55 (m, 1H), 7.26-7.10 (m, 9H), 5.75 (m, 1H), 4.47 (m, 1H), 3.82 (m, 1H), 2.80 (m, 2H).

4.5 N-(4-Amino-3,4-dioxo-1-phenylbutan-2-yl)-2-(4-(4-fluorophenyl)thiazol-2-yl)nicotinamide N-(4-Amino-3-hydroxy-4-oxo-1-phenylbutan-2-yl)-2-(4-(4-fluorophenyl)thiazol-2-yl)nicotin-amide (310 mg, 0.651 mmol) was oxidized in a manner analogous to example 1.3. The crude product obtained after work up was crystallized from 2-propanole, the precipitate formed filtered off with suction and dried to give 205 mg of the title compound as white solid; ESI-MS [M+H+]: 475.15.
¹H-NMR (500 MHz DMSO) δ ppm 8.96 (m, 1H), 8.69 (m, 1H), 8.22 (s, 1H), 8.10 (s, 1H), 7.89 (m, 3h), 7.58 (m, 2H), 7.23-7.10 (m, 7H), 5.70 (m, 1H), 3.12 and 2.68 (each dd, 1H).

Example 5

N-(4-Amino-3,4-dioxo-1-phenylbutan-2-yl)-2-[2-(4-fluorophenyl)-1,3-thiazol-4-yl]pyridine-3-carboxamide 5.1 2-(2-Bromoacetyl)-3-(methoxycarbonyl)pyridinium bromide To a solution of methyl 2-acetylnicotinate (750 mg, 4.19 mmol)—prepared according to H. Nagano et al.; Heterocycles 1987, 26, 1263-1270—in 2 ml of 33% HBr in acetic acid a suspension of pyridinium bromide perbromide (1.4 g, 4.38 mmol) in 5 ml of acetic acid was added, and stirred for 5 hours at room temperature. The precipitate formed was filtered off under suction, washed with n-pentane and dried to give 1.17 g of the title compound.

5.2 Methyl 2-(2-(4-fluorophenyl)thiazol-4-yl)nicotinate

To a solution of 2-(2-bromoacetyl)-3-(methoxycarbonyl) pyridinium bromide (1.17 g, 3.45 mmol) in 10 ml of DMF 4-fluorobenzothioamide (0.7 g, 4.51 mmol) were added and stirred at room temperature over night. For work up the reaction mixture was evaporated to dryness and the obtained crude oil purified by chromatography on silica gel (eluent: CH$_2$CL$_2$+0.2% methanol) to give 865 mg of the thiazole as yellow oil.
ESI-MS [M+H]$^+$: 315.05.

5.3 2-(2-(4-Fluorophenyl)thiazol-4-yl)nicotinic acid 5.5 ml of a 2N NaOH solution were added to a solution of methyl 2-(2-(4-fluorophenyl)thiazol-4-yl)nicotinate (850 mg, 2.7 mmol) in 30 ml of methanol, and afterwards stirred for 4 hours at 50° C. The reaction mixture was evaporated to dryness, mixed with water and neutralized by adding 2N HCl. Filtration with suction and drying the precipitate formed resulted in 690 mg of the acid as amorphous solid.
ESI-MS [M+H]$^+$: 301.0.

5.4 N-(4-Amino-3-hydroxy-4-oxo-1-phenylbutan-2-yl)-2-(2-(4-fluorophenyl)thiazol-4-yl)nicotinamide Coupling of 2-(2-(4-fluorophenyl)thiazol-4-yl)nicotinic acid (350 mg, 1.165 mmol) and 3-amino-2-hydroxy-4-phenylbutanamide (270 mg, 1.39 mmol) in an analogous manner as described for example 1.2 afforded 520 mg of the title compound as white amorphous solid; ESI-MS [M+H+]: 477.1.
¹H-NMR (500 MHz DMSO) δ ppm 8.68 (m, 1H), 8.28 (d, 1H), 7.96 (m, 3H), 7.70 (m, 1H), 7.44 (m, 1H), 7.30-7.20 (m, 9H), 5.76 (d, 1H), 4.37 (m, 1H), 3.83 (m, 1H), 2.82 and 2.67 (each m, 1H).

5.5 N-(4-Amino-3,4-dioxo-1-phenylbutan-2-yl)-2-(2-(4-fluorophenyhthiazol-4-yl)nicotinamide N-(4-Amino-3-hydroxy-4-oxo-1-phenylbutan-2-yl)-2-(2-(4-fluorophenyhthiazol-4-yl)nicotin-amide (350 mg, 0.734 mmol) was oxidized in a manner analogous to example 1.3. The crude product obtained after work up was crystallized from 2-propanole, the precipitate formed filtered off with suction and dried to give 208 mg of the title compound as white solid.

ESI-MS [M+H]$^+$: 475.1.
$^1$H-NMR (500 MHz DMSO) δ ppm: 8.86 (m, 1H), 8.68 (m, 1H), 8.11 (s, 2H), 7.87 (m, 3H), 7.60 (m, 1H), 7.47 (m, 1H), 7.29 (m, 2H), 7.15 (m, 5H), 5.55 (m, 1H), 3.10 and 2.81 (each dd, 1H).

The compounds of the following examples were prepared in a manner analogous to the preparation of example 5, if not indicated otherwise:

Example 6

N-(4-Amino-3,4-dioxo-1-phenylbutan-2-yl)-2-{2-[3-(trifluoromethyl)phenyl]-1,3-thiazol-4-yl}pyridine-3-carboxamide ESI-MS [M+H]$^+$: 525.0.
$^1$H-NMR (500 MHz DMSO) δ ppm: 8.82 (m, 1H), 8.71 (m, 1H), 8.19 (s, 1H), 8.01 (m, 2H), 7.81 (m, 2H), 7.68 (m, 2H), 7.49 (m, 1H), 7.1-7.0 (m, 5H), 5.41 (m, 1H), 3.1 and 2.68 (each dd, 1H).

Example 7

N-(4-Amino-3,4-dioxo-1-phenylbutan-2-yl)-2-(2-phenyl-1,3-thiazol-4-yl)pyridine-3-carboxamide ESI-MS [M+H]$^+$: 457.2.
$^1$H-NMR (500 MHz DMSO) δ ppm: 8.86 (m, 1H), 8.69 (m, 1H), 8.10 (s, 1H), 8.05 (s, 1H), 7.83 (m, 3H), 7.62 (m, 1H), 7.44 (m, 4H), 7.15 (m, 5H), 5.56 (m, 1H), 3.12 and 2.75 (each dd, 1H).

Example 8

N-(4-Amino-3,4-dioxo-1-phenylbutan-2-yl)-2-[2-(2-chlorophenyl)-1,3-thiazol-4-yl]pyridine-3-carboxamide ESI-MS [M+H]$^+$: 491.1.
$^1$H-NMR (500 MHz DMSO) δ ppm: 8.82 (d, 1H), 8.70 (m, 1H), 8.30 (s, 1H), 8.12 (, 1H), 8.04 (s, 1H), 7.81 (s, 1H), 7.63 (m, 2H), 7.48 (m, 2H), 7.38 (m, 1H), 7.0 (m, 5H), 5.52 (m, 1H), 3.08 and 2.69 (each dd, 1H).

Example 9

N-(4-Amino-3,4-dioxo-1-phenylbutan-2-yl)-2-[2-(naphthalen-2-yl)-1,3-thiazol-4-yl]pyridine-3-carboxamide ESI-MS [M+H]$^+$: 507.2.
$^1$H-NMR (500 MHz DMSO) δ ppm: 8.92 (m, 1H), 8.71 (m, 1H), 8.47 (s, 1H), 8.15 (s, 1H), 8.08 (m, 2H), 7.98 (m, 3H), 7.83 (s, 1H), 7.63 (m, 3H), 7.49 (m, 1H), 7.12 (m, 2H), 7.05 (m, 3H), 5.61 (m, 1H), 3.11 and 2.76 (each dd, 1H).

Example 10

N-(1-Amino-1,2-dioxoheptan-3-yl)-2-(2-phenylthiazol-4-yl)nicotinamide

ESI-MS [M+H]$^+$: 423.1.
$^1$H-NMR (500 MHz DMSO) δ ppm: 8.69 (m, 1H), 8.65 (d, 1H), 8.23 (s, 1H), 7.98 (s, 1H), 7.93 (m, 2H), 7.28 (m, 2H), 7.55 (m, 4H), 5.18 (m, 1H), 1.68 (m, 1H), 1.43 (m, 1H), 1.13 (m, 4H), 0.68 (m, 3H).

Example 11

N-(1-Amino-1,2-dioxoheptan-3-yl)-2-(2-phenyl-1,3-thiazol-4-yl)benzamide

11.1 N-(1-Amino-2-hydroxy-1-oxoheptan-3-yl)-2-(2-phenylthiazol-4-yl)benzamide Coupling of 2-(2-phenylthiazol-4-yl)benzoic acid (200 mg, 0.711 mmol) and 1-amino-2-hydroxy-1-oxoheptan-3-aminium chloride (145 mg, 0.737 mmol) in an analogous manner as described for example 1.2 afforded 264 mg of the title compound as white solid.

ESI-MS [M+H]$^+$: 424.15.

11.2 N-(1-Amino-1,2-dioxoheptan-3-yl)-2-(2-phenyl-1,3-thiazol-4-yl)benzamide N-(1-Amino-2-hydroxy-1-oxoheptan-3-yl)-2-(2-phenylthiazol-4-yl)benzamide (120 mg, 0.283 mmol) was oxidized in a manner analogous to example 1.3. Recrystallization of the crude product in 2-propanole gave 50 mg of the title compound.

ESI-MS [M+H]$^+$: 422.1.
$^1$H-NMR (500 MHz DMSO) δ ppm: 8.66 (d, 1H), 7.98 (m, 3H), 7.89 (d, 1H), 7.81 (s, 1H), 7.74 (s, 1H), 7.55-7.41 (m, 7H), 5.06 (m, 1H), 1.69 and 1.45 (each m, 1H), 1.18 (m, 4H), 0.75 (m, 3H).

Example 12

N-(4-Amino-3,4-dioxo-1-phenylbutan-2-yl)-2-(2-phenyl-1,3-thiazol-4-yl)benzamide

Prepared in a manner analogous to the preparation of example 10 giving 60 mg of the title compound as white solid.
ESI-MS [M+H]$^+$: 456.1.
$^1$H-NMR (500 MHz DMSO) δ ppm: 8.90 (d, 1H), 8.09 (s, 1H), 7.92 (m, 3H), 7.84 (s, 1H), 7.45-7.23 (m, 13H), 5.45 (m, 1H), 3.20 and 2.78 (each dd, 1H).

Example 13

N-(4-(Cyclopropylamino)-3,4-dioxo-1-phenylbutan-2-yl)-2-(2-phenylthiazol-4-yl)nicotinamide

13.1 Ethyl 2-hydroxy-4-phenyl-3-(2-(2-phenylthiazol-4-yl)nicotinamido)butanoate N-(3-Dimethylaminopropyl)-N'-ethylcarbodiimide hydrochloride (EDC) (700 mg, 3.65 mmol), 1-hydroxybenzotriazole hydrate (550 mg, 3.59 mmol) and N,N-diisopropylethylamine (DIPEA) (1.2 ml, 6.87 mmol) were successively added to a solution of (2-phenylthiazol-4-yl)nicotinic acid (820 mg, 2.90 mmol) and 4-ethoxy-3-hydroxy-4-oxo-1-phenylbutan-2-aminium chloride (800 mg, 3.08 mmol) in dichloromethane (70 ml) at 5° C., and the mixture stirred at 5° C. for about 5 minutes. A pH of 8 was adjusted by adding 0.6 ml of DIPEA, the mixture stirred for 1 hour at 5° C. and then overnight at room temperature. The mixture then was concentrated under reduced pressure, poured into 200 ml of water, the precipitate formed was filtered off with suction and dried in vacuo to give 1.33 g of the title product as white amorphous solid.

$^1$H-NMR (400 MHz DMSO) δ [ppm]: 8.68 (m, 1H), 8.23 (m, 1H), 7.96 (m, 2H), 7.86 (s, 1H), 7.65 (dd, 1H), 7.40 (m, 3H), 7.17 (m, 5H), 5.45 (d, 1H), 4.42 (m, 1H), 3.99 (m, 3H), 2.82 and 2.66 (each m, 1H), 1.12 (m, 3H).

13.2 2-Hydroxy-4-phenyl-3-(2-(2-phenylthiazol-4-yl)nicotinamido)butanoic acid To a solution of ethyl 2-hydroxy-4-phenyl-3-(2-(2-phenylthiazol-4-yl)nicotinamido)-butanoate (1.31 g, 2.69 mmol) in THF (40 ml) LiOH (0.14 g, 5.85 mmol) in water (10 ml) was added at 10° C., the mixture stirred for 1 hour at room temperature and then for 2 hours at 60° C. The mixture then was concentrated under reduced pressure, water and 3 ml of 2n HCl added, poured into 300 ml of a mixture of dichloromethane and 5% acetone. The organic layer was dried, filtered and concentrated under reduced pressure to give 1.19 g of the title acid;

ESI-MS [m+H]$^+$=460.1.

13.3 N-(4-(Cyclopropylamino)-3-hydroxy-4-oxo-1-phenylbutan-2-yl)-2-(2-phenylthiazol-4-yl)nicotinamide To a solution of 2-hydroxy-4-phenyl-3-(2-(2-phenylthiazol-4-yl)nicotinamido)butanoic acid (230 mg, 0.501 mmol) and cyclopropylamine (40 µL, 0.570 mmol) in dichloromethane (30 ml) 2-(1H-7-azabenzotriazol-1-yl)-1,1,3,3-tetramethyl uronium hexafluorophosphate (HATU) (230 mg, 0.605 mmol) and DIPEA (100 µL, 0.605 mmol) were added at 5° C. The mixture was stirred for 1 hour at 5° C. and then for 5 hours at room temperature. The mixture was concentrated under reduced pressure, 40 ml of water added, the precipitate formed filtered off with suction, washed with water and dried in vacuo to give 227 mg of a white amorphous solid;

ESI-MS [M+H]$^+$=499.2.

13.4 N-(4-(Cyclopropylamino)-3,4-dioxo-1-phenylbutan-2-yl)-2-(2-phenylthiazol-4-yl)nicotinamide EDC (700 mg, 3.65 mmol) and 2,2-dichloroacetic acid (124 1, 1.46 mmol) were added to a solution of N-(4-(cyclopropylamino)-3-hydroxy-4-oxo-1-phenylbutan-2-yl)-2-(2-phenylthiazol-4-yl)nicotinamide (217 mg, 0.435 mmol) in dimethyl sulfoxide (DMSO) (4 ml), and the reaction mixture stirred for 10 min at room temperature. For work up the reaction mixture was mixed with 80 ml of sat. NaHCO$_3$-solution for 10 minutes. The resulting solid was filtered off with suction, washed with water and dried in vacuo to give 193 mg of the title product as white amorphous solid;

ESI-MS [m+H]$^+$=497.1.

$^1$H-NMR (400 MHz DMSO), δ [ppm]: 8.84 (d, 1H), 8.72 (m, 2H), 8.11 (s, 1H), 7.84 (m, 2H), 7.60 (m, 1H), 7.45 (m, 4H), 7.21 (m, 5H), 5.58 (m, 1H), 3.09 (m, 2H), 2.70 (m 2H), 0.67 (m, 2H), 0.57 (m, 2H).

Example 14

N-(4-(Methoxyamino)-3,4-dioxo-1-phenylbutan-2-yl)-2-(2-phenylthiazol-4-yl)nicotinamide

14.1 N-(3-Hydroxy-4-(methoxyamino)-4-oxo-1-phenylbutan-2-yl)-2-(2-phenylthiazol-4-yl)nicotinamide DIPEA (200 µl, 0.567 mmol) was added to a suspension of 2-hydroxy-4-phenyl-3-(2-(2-phenylthiazol-4-yl)nicotinamido)butanoic acid (250 mg, 0.544 mmol) and O-methylhydroxylamine hydrochloride (90 mg, 1.078 mmol) in dichloromethane (50 ml) at 5° C. After about 5 min 2-(1H-7-azabenzotriazol-1-yl)-1,1,3,3-tetramethyl uronium hexafluorophosphate (HATU) (665 mg, 1.748 mmol) was added, the pH adjusted to 8 via addition of further DIPEA, and the mixture then stirred for 1 h at 5° C. and then overnight at room temperature. Then dichloromethane (50 ml) was added, washed 2× with 10 ml of water and brine, dried, filtered and concentrated to give 430 mg of the crude product which was purified by chromatography on silica gel (dichloromethane+11-12% methanol. Concentration of the combined fractions and drying afforded 224 mg of a white amorphous solid;

ESI-MS [M+H]$^+$: 489.1.

14.2 N-(4-(Methoxyamino)-3,4-dioxo-1-phenylbutan-2-yl)-2-(2-phenylthiazol-4-yl)nicotinamide To polymer-supported IBX (Novabiochem, 1.1 mmol/g; 400 mg, 0.440 mmol) in dichloromethane (5 ml) N-(3-hydroxy-4-(methoxyamino)-4-oxo-1-phenylbutan-2-yl)-2-(2-phenylthiazol-4-yl)nicotinamide (140 mg, 0.287 mmol) in 10 ml of dichloromethane was added and the mixture shaken for 2 days at room temperature. IBX was added again twice (200 mg, 0.220 mmol) at intervals of 1 day. After another 4 days the mixture was filtered and concentrated under reduced pressure to 135 mg of the crude product which was purified by chromatography on silica gel. The combined fractions were concentrated, the remainder treated with water, filtered off with suction and dried to 84 mg of the desired product;

ESI-MS [M+H]$^+$: 489.1

$^1$H-NMR (400 MHz DMSO), δ [ppm]: 12.01 (s broad, 1H), 8.89 (s broad, 1H), 8.68 (d, 1H), 8.02 (s, 1H), 7.84 (m, 2H), 7.61 (m, 1H), 7.45 (m, 4H), 7.21 (m, 5H), 5.48 (m, 1H), 3.77 (s, 3H), 3.16 and 2.66 (each m, 1H).

Example 15

N-(4-Amino-1-(4-fluorophenyl)-3,4-dioxobutan-2-yl)-2-(2-phenylthiazol-4-yl)nicotinamide The title compound was prepared in a manner analogous to the preparation of example 5 yielding 146 mg of the title compound as a white solid; ESI-MS [M+H+]: 475.05.

$^1$H-NMR (500 MHz DMSO) δ ppm: 8.80 (d, 1H), 8.70 (m, 1H), 8.13 (s, 1H), 8.03 (m, 1H), 7.82 (m, 2H), 7.65 (m, 1H), 7.47 (m, 5h), 7.15 (m, 2h), 6.88 (m, 2H), 5.47 (m, 1H), 3.1 and 2.68 (each m, 1H).

Example 16

N-(4-amino-3,4-dioxo-1-phenylbutan-2-yl)-2-(benzo[d]oxazol-2-yl)nicotinamide

16.1 Ethyl 2-(benzo[d]oxazol-2-yl)nicotinate

A mixture of ethyl 2-chloronicotinate (100 mg, 0.539 mmol), 2-(tributylstannyl)benzo[d]oxazole (314 mg, 0.539 mmol) and [1,1'-bis(diphenylphosphino) ferrocene]-dichloropalladium (II) (39.4 mg, 0.054 mmol) in DMF (2 mL) was heated to 110° C. for 1 h by applying microwave radiation to the mixture. The reaction was repeated on the same scale and the thus obtained reaction mixtures obtained were combined. Excess water and EtOAc were added. The organic layer was separated and the aqueous layer was extracted with EtOAc. The combined organic layers were washed with water and dried over $MgSO_4$. Purification by flash column chromatography (EtOAc/DCM, gradient: 1-10% DCM) provided the title compound (290 mg, 90%);

ESI-MS [M+H+]=269.1.

16.2 2-(benzo[d]oxazol-2-yl)nicotinic acid

NaOH (1.65 mL, 2M in water) was added to a solution of ethyl 2-(benzo[d]oxazol-2-yl)nicotinate (290 mg, 0.973 mmol) in EtOH. After stirring for 3 h at room temperature the solvent was removed in vacuo. The residue was dissolved in water (4 mL) and dilute HCl (1.8 mL, 2M in water) was added resulting in pH 2-3 of the mixture. The mixture was extracted with dichloromethane. The combined organic layers were washed with saturated aqueous NaCl solution and dried over $MgSO_4$. Removal of the solvent provided the title compound (190 mg, 81%); ESI-MS [M+H+]=241.1.

16.3 N-(4-amino-3-hydroxy-4-oxo-1-phenylbutan-2-yl)-2-(benzo[d]oxazol-2-yl)nicotinamide Coupling of 2-(benzo[d]oxazol-2-yl)nicotinic acid (190 mg, 0.791 mmol) and 3-amino-2-hydroxy-4-phenylbutanamide (169 mg, 0.780 mmol) was performed by analogy to the method described for example 1.2 using DIPEA instead of triethylamine. The reaction yielded 279 mg of the title compound; ESI-MS [M+H+]=417.1.

16.4 N-(4-amino-3,4-dioxo-1-phenylbutan-2-yl)-2-(benzo[d]oxazol-2-yl)nicotinamide N-(4-amino-3-hydroxy-4-oxo-1-phenylbutan-2-yl)-2-(benzo[d]oxazol-2-yl)nicotinamide (60 mg, 0.144 mmol) was oxidized by analogy to example 1.3. The crude product was purified by flash column chromatography (dichloromethane/MeOH, gradient 1-9% MeOH) providing 8.5 mg of the title compound; ESI-MS [M+H+]=415.1.

$^1$H-NMR (500 MHz DMSO): δ ppm: 9.19 (d, 1H), 8.85 (d, 1H), 8.09 (s, 1H), 7.84-7.71 (m, 5H), 7.51-7.44 (m, 2H), 7-29-7.17 (m, 5H), 5.48-5.46 (m, 1H), 3.22-3.18 (m, 1H), 2.96-2.88 (m, 1H).

Example 17

N-(4-amino-3,4-dioxo-1-phenylbutan-2-yl)-2-(2-phenyloxazol-4-yl)nicotinamide

17.1 2-phenyloxazol-4-yl trifluoromethanesulfonate 2-phenyloxazol-4-yl trifluoromethanesulfonate was prepared as described by N. F. Langille, L. A. Dakin, J. S. Panek, *Organic Letters* 2002, 4, 15, 2485.

17.2 2-phenyl-4-(4,4,5,5-tetramethyl-1,3,2-dioxaborolan-2-yl)oxazole 2-phenyl-4-(4,4,5,5-tetramethyl-1,3,2-dioxaborolan-2-yl) oxazole was prepared from 2-phenyloxazol-4-yl trifluoromethanesulfonate according to the procedure published by H. Araki, T. Katoh, M. Inoue, *Synlett* 2006, 4, 555.

17.3 Ethyl 2-(2-phenyloxazol-4-yl)nicotinate

[1,3-Bis(2,6-Diisopropylphenyl)imidazol-2-ylidene](3-chloropyridyl)palladium(II) dichloride (22 mg, 0.032 mmol) was added to a mixture of ethyl-2-chloronicotinate (120 mg, 0.647 mmol) and 2-phenyl-4-(4,4,5,5-tetramethyl-1,3,2-dioxaborolan-2-yl)oxazole (220 mg, 0.811 mmol) in dioxane (5 mL). After the addition of $K_2CO_3$ (402 mg, 2.910 mmol) the reaction mixture was heated at 65° C. for 4 h and then allowed to cool to room temperature. Water was added and the mixture was extracted with EtOAc. The combined organic layers were washed with water and dried ($MgSO_4$). Purification of the thus obtained raw product by flash column chromatography (dichloromethane/EtOAc, gradient 5-10% EtOAc) provided the title compound (80 mg, 42%); ESI-MS [M+H+]=295.1.

17.4 2-(2-phenyloxazol-4-yl)nicotinic acid

An aqueous solution of NaOH (0.27 mL, 2M in water, 0.54 mmol) was added to a solution of ethyl 2-(2-phenyloxazol-4-yl)nicotinate (80 mg, 0.27 mmol) in EtOH (2.7 mL). After stirring overnight at room temperature the solvent was removed in vacuo, the residue was dissolved in water and HCl (2M in water) was added until pH ~1 was obtained. The solvent was removed in vacuo and the crude product obtained was used without further purification; ESI-MS [M+H+]=267.1.

17.5 N-(4-amino-3-hydroxy-4-oxo-1-phenylbutan-2-yl)-2-(2-phenyloxazol-4-yl)nicotinamide Coupling of 2-(2-phenyloxazol-4-yl)nicotinic acid (120 mg, 60% pure, 0.270 mmol) and 3-amino-2-hydroxy-4-phenylbutanamide (58 mg, 0.297 mmol) by analogy to the method of example 1.2 using DIPEA instead of $NEt_3$ afforded 87 mg of the title compound; ESI-MS [M+H+]=443.2.

17.6 N-(4-amino-3,4-dioxo-1-phenylbutan-2-yl)-2-(2-phenyloxazol-4-yl)nicotinamide N-(4-amino-3-hydroxy-4-oxo-1-phenylbutan-2-yl)-2-(2-phenyloxazol-4-yl)nicotinamide (80 mg, 0.181 mmol) was oxidized by analogy to the method of example example 1.3;

ESI-MS [M+H+]=441.1.

$^1$H-NMR (400 MHz DMSO) δ ppm: 8.98 (d, 1H), 8.69 (dd, 1H), 8.40 (s, 1H), 8.07, s, 1H), 7.92-7.90 (m, 2H), 7.84 (s, 1H), 7.63-7.61 (m, 1H), 7.55 (m, 3H), 7.47-7.46 (m, 1H), 7.28-7.13 (m, 5H), 5.53-5.50 (m, 1H), 3.18 (dd, 1H), 2.81 (dd, 1H).

Biological Investigation of Inhibition of Calpain and Cathepsins

The following solutions and buffers were employed:

HBS (for 40 ml): 800 µl 1M HEPES; 2.16 ml 100 mM KCl; 4.8 ml 1M NaCl; 3.59 ml 5% glucose; 60 µl 1M $MgSO_4$; 400 µl 100 mM Na pyruvate, 28.19 ml water; pH 7.2-7.5.

lysis buffer (for 20 ml): 400 µl 1M Tris pH 8.2; 2.74 ml 1M NaCl; 520 µl 0.5M EDTA; 2 ml 10% triton X-100; 0.8 ml (=1:25) CompletePlus (1 tablet/2 ml $H_2O$); 200 µl 100 mM Pefabloc; 13.34 ml water, pH 8.2.

TBST (10×) (for 1 l): 100 mM Tris (12.1 g); 1.5M NaCl (87 g); 1% Tween 20 (10 g), adjusted to pH 8.

I Enzyme Inhibition In Vitro:

Testing for blockade of the corresponding enzymic activities was carried out by means of kinetic fluorescence assays (excitation 390 nm, emission 460 nm).

Apparent Ki values were calculated from the experimentally determined $IC_{50}$ values by the Cheng-Prussoff relation assuming a reversible competitive enzyme inhibition. The Km values of the substrates used under the assay conditions indicated above were: 90 µM (Z-Phe-Arg-AMC, cathepsin B), 10 µM (Z-Gly-Pro-Arg-AMC, cathepsin K), 2 µM (Z-Phe-Arg-AMC, cathepsin L), and 30 µM (Z-Val-Val-Arg-AMC, cathepsin S).

The indicated Ki values are averages of the inhibition constants calculated on the basis of 2 to 4 independent dose-effect plots.

The following assays were used:

1. Calpain I:
   20 nM calpain-I—isolated from human erythrocytes (Calbiochem #208713), 100 µM Suc-Leu-Tyr-AMC (Bachem #I-1355) as substrate in buffer with 62 mM imidazole, 0.3 mM $CaCl_2$, 0.10% CHAPS, 0.05% BSA, 1 mM DTT at pH 7.3 and room temperature.
2. Cathepsin B:
   0.25 nM cathepsin B—isolated from human liver (Calbiochem #219362), 100 µM Z-Phe-Arg-AMC (Bachem #I-1160) as substrate 50 mM MES, 2 mM EDTA, 0.05% Brij 35, 2.5 mM L-cysteine, pH 6.0, room temperature.
3. Cathepsin K:
   3 nM cathepsin K—activated from recombinant human procathepsin K from *E. coli* (Calbiochem #342001), 10 µM Z-Gly-Pro-Arg-AMC (Biomol #P-142) as substrate in 50 mM MES, 2 mM EDTA, 0.05% Brij 35, 2.5 mM L-cysteine, pH 6.0, room temperature.
4. Cathepsin L:
   1 nM cathepsin L—isolated from human liver (Calbiochem #219402),
   2 µM Z-Phe-Arg-AMC (Bachem #I-1160) as substrate in 50 mM MES,
   2 mM EDTA, 0.05% Brij 35, 2.5 mM L-cysteine, pH 6.0, room temperature.
5. Cathepsin S:
   0.5 nM recombinant human cathepsin S from *E. coli* (Calbiochem #219343), 20 µM Z-Val-Val-Arg-AMC (Bachem #I-1540) as substrate in 50 mM MES, 2 mM EDTA, 0.05% Brij 35, 2.5 mM L-cysteine, pH 6.0, room temperature.

The results of the in vitro determination are indicated in Table 1. The following abbreviations are used in Table 1:

In the "Calpain activity" column, +++ stands for a calpain Ki (Ki(calpain)) of ≤40 nM, and ++ means: 40 nM<Ki(Calpain)≤100 nM and + means 100 nM<Ki(Calpain)≤300 nM.

The "Sel. cat. B" column indicates the Ki(cathepsin B)/Ki(calpain) ratio. In this connection, ++ means a Ki(cathepsin B)/Ki(calpain) ratio of ≥30 and + means 10≤Ki(cathepsin B)/Ki(calpain)<30.

The "Sel. cat. K" column indicates the Ki(cathepsin K)/Ki(calpain) ratio. In this connection, ++ means a Ki(cathepsin K)/Ki(calpain) ratio of ≥30 and + means 10≤Ki(cathepsin K)/Ki(calpain)<30.

The "Sel. cat. L" column indicates the Ki(cathepsin L)/Ki(calpain) ratio. In this connection, ++ means a Ki(cathepsin L)/Ki(calpain) ratio of ≥50 and + means 30≤Ki(cathepsin L)/Ki(calpain)<50.

The "Sel. cat. S" column indicates the Ki(cathepsin S)/Ki(calpain) ratio. In this connection, ++ means a Ki(cathepsin S)/Ki(calpain) ratio of ≥100 and + means 50≤Ki(cathepsin S)/Ki(calpain)<100.

TABLE 1

| Example | Calpain activity | Sel cat. B | Sel cat. K | Sel cat. L | Sel cat. S | human cytCL | cyno cytCL |
|---|---|---|---|---|---|---|---|
| 2 | + | | + | | | | |
| 3 | ++ | + | + | ++ | ++ | | |
| 4 | ++ | + | + | ++ | ++ | | |
| 5 | ++ | + | | + | ++ | | |
| 6 | +++ | ++ | + | ++ | ++ | | |
| 7 | +++ | ++ | + | ++ | ++ | | |
| 8 | +++ | ++ | + | ++ | ++ | | |
| 9 | ++ | ++ | + | ++ | ++ | | |
| 13 | + | ++ | + | + | | ++ | ++ |
| 14 | + | | | ++ | ++ | ++ | ++ |
| 15 | ++ | ++ | + | ++ | ++ | | |
| 16 | + | + | + | | ++ | | |

II Spectrin molt-4 assay to determine cellular calpain inhibition:

The assay design and procedure were as disclosed by Chatterjee; BMC 1998, 6, pp. 509-522; the $EC_{50}$ values are calculated from the percentage degradation of spectrin as a function of the dose.

Cell culture conditions: the molt-4 cells are maintained in RPMI 1640+Glutamax™ I medium (Gibco) with 10% FCS and 50 µg/ml gentamicin at 37° C., 5% $CO_2$ and split 1:15 twice a week.

Preparation of the molt-4 cells: the cells are washed, counted and taken up in a concentration of $2 \times 10^7$ cells/ml in HBS buffer.

Dilution of the inhibitor substances: all the inhibitors are dissolved in a concentration of $10^{-2}$ M in DMSO. The stock solution is then diluted 1:15 in DMSO (=6.67× $10^{-4}$ M). Thereafter the stock solution diluted 1:15 is diluted 1:4 in DMSO in two steps (=1.67×$10^{-4}$ M and 4.17×$10^{-5}$ M). Thereafter, these three solutions are further diluted 1:50 in HBS buffer to give solutions having a concentration of 1.33×$10^{-5}$ M, 3.36×$10^{-6}$ M and 8.34× $10^{-7}$ M.

Test mixture: for each mixture, $10^6$ cells (see above) are introduced into a 1.5 ml Eppendorf tube. To these are added in each case 150 µl of the diluted substances (final conc. $10^{-5}$ M; 2.5×$10^{-6}$ M and 6.25×$10^{-7}$ M) and thoroughly mixed. A negative control and a positive control are used as controls. In this case, initially only 150 µl of HBS buffer is pipetted onto the cells. All the mixtures are incubated at 37° C., 5% $CO_2$ in an incubator for 10 min. Thereafter, except for the negative control, in each case $CaCl_2$ (final conc. 5 mM) and ionomycin (final conc. 5 µM) are added, thoroughly mixed and incubated at 37° C., 5% $CO_2$ in an incubator for 30 min. Then centrifuge at 700 g for 5 min. The supernatants are discarded and the pellets are taken up in 20 µl of lysis buffer. The mixtures are subsequently placed on ice for 30-60 min and then centrifuged at 15000 g for 15 min. The supernatants are removed and put into new Eppendorf tubes. The protein determination is then carried out thereon, e.g. with a MicroBCA assay (Pierce).

SDS-PAGE electrophoresis: 10 µg of total protein from each mixture are put into a new Eppendorf tube and, after pipetting in the same volume of 2× Tris-glycine SDS sample buffer (Invitrogen) and ⅒ volume of 1M DTT, thoroughly mixed and heated at 95° C. for 15 min. The solutions are briefly centrifuged and loaded onto a 6% SDS gel (Invitrogen). The gel is run at 100V with 1×

Tris-glycine laemmli buffer (Biomol) until the lower band of the marker has reached the base of the gel.

Western blotting: the gel is removed from the apparatus and blotted onto nitrocellulose in 1× Tris-glycine transfer buffer (Invitrogen)+20% methanol with 1.5 A/cm² in a FastBlot chamber (Biometra) for 30 min. The nitrocellulose filter is removed, briefly washed in TBST buffer and blocked in TBST/5% milk powder for 1 h at RT (room temperature). The blocked nitrocellulose is then incubated with an anti-spectrin Ab (Chemicon) (1:10000 in TBST/5% milk powder) at RT for 3 h or at 4° C. overnight. The nitrocellulose is washed 3× in TBST buffer. It is then incubated with anti-mouse IgG (POD) antibody (Sigma) (1:10000 in TBST/5% milk powder) at room temperature for 1 h.

The nitrocellulose is then washed 5× in TBST buffer. In the next step, 5 ml of prepared solution of the SuperSignal® West Pico chemiluminescence substrate (Pierce) are put on the filter and incubated for 5 min. The nitrocellulose is then taken out of the solution, gently dabbed dry and inserted into a development folder film (Tropix). A digital image analysis system (VersaDoc, Biorad) is used to record and quantify the ECL (QuantityOne), and the percentage degradation of spectrin is calculated from the data. Graph-pad prism is used to fit the percentage spectrum degradation as a function of the dose to a sigmoidal dose-effect plot (top fixed at 100% and bottom at 0%), and the EC 50% is calculated.

III Assay for Determining Cytosolic Clearance of Compounds of Formula I:

For comparison purposes data measured with human liver cytosol were contrasted with those obtained with cynomolgus monkey liver cytosol.

0.5 µM of a compound to be tested was incubated with 1 mg/ml of human liver cytosol as well as monkey liver cytosol at 37° C. in 0.5 M of phosphate buffer at pH 7.5 while shaking (commercial sources: female cynomolgus liver cytosol from Tebu bio, human liver cytosol from BDgentest).

In each case aliquots of 65 µl were taken after 0, 5, 10 and 15 min and transferred into wells of a wellplate which were immediately filled with 130 µl of ethanol to stop the reaction. The samples were kept frozen until analysis on a LC/MS/MS system (Applied Biosystems SCIEX 4000).

Read out parameters were the loss of parent compounds, from which the half life periods ($T_{1/2}$) were calculated from. Based on these data the parameters cytosolic clearance (cytCL), scaled clearance (CLs) and predicted clearance (CLp) were calculated using the following equations:

1) cytCL=(ln 2/$T_{1/2}$)×[cytosolic protein]×1000
2) CLs=cytCL×[cytosolic yield]/1,000,000×60
3) CLp=(CLs+hepatic plasma flow)/hepatic plasma flow/CLs To assess the stability of the compounds tested the clearance ranges were adjusted to the hepatic plasma flow of the different species according to the following scheme:
stable=from 0 to about ⅓ of the hepatic plasma flow;
moderately stable=from about ⅓ to about ⅔ of the hepatic plasma flow;
instable=more than ⅔ of the hepatic plasma flow.
Based on this adjustment the following qualifiers were assigned to evaluate the cytosolic stabilities of the compounds tested. The cytCL data obtained this way for the inventive compounds are depicted in the table below.

| cytCL | symbol | human | cynomolgus monkey (cyno) |
|---|---|---|---|
| stable | ++ | 0-14 µl/min/mg | 0-18 µl/min/mg |
| moderately stable | + | 14-70 µl/min/mg | 18-90 µl/min/mg |
| instable | — | >70 µl/min/mg | >90 µl/min/mg |

We claim:
1. A carboxamide compound of the formula I

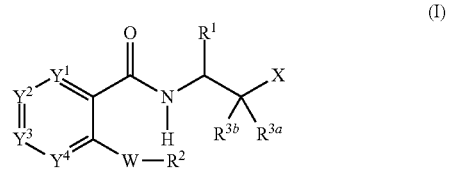

in which
R¹ is hydrogen, $C_1$-$C_{10}$-alkyl, $C_2$-$C_{10}$-alkenyl, $C_2$-$C_{10}$-alkynyl, where the last 3 radicals mentioned may be partly or completely halogenated and/or have 1, 2 or 3 substituents $R^{1a}$,
$C_3$-$C_7$-cycloalkyl, $C_3$-$C_7$-cycloalkyl-$C_1$-$C_4$-alkyl, where a $CH_2$ group in the cycloalkyl moiety of the last two radicals mentioned may be replaced by O, NH, or S, or two adjacent C atoms may form a double bond, where the cycloalkyl moiety may further have 1, 2, 3 or 4 radicals $R^{1b}$,
aryl, hetaryl, aryl-$C_1$-$C_6$-alkyl, aryl-$C_2$-$C_6$-alkenyl, hetaryl-$C_1$-$C_4$-alkyl or hetaryl-$C_2$-$C_6$-alkenyl, where aryl and hetaryl in the last 6 radicals mentioned may be unsubstituted or carry 1, 2, 3 or 4 identical or different radicals $R^{1c}$; where
$R^{1a}$ is selected independently of one another from OH, SH, COOH, CN, $OCH_2COOH$, $C_1$-$C_6$-alkoxy, $C_1$-$C_6$-haloalkoxy, $C_3$-$C_7$-cycloalkyloxy, $C_1$-$C_6$-alkylthio, $C_1$-$C_6$-haloalkylthio, $COOR^{a1}$, $CONR^{a2}R^{a3}$, $SO_2NR^{a2}R^{a3}$, —$NR^{a2}$—$SO_2$—$R^{a4}$, $NR^{a2}$—CO—$R^{a5}$, $SO_2$—$R^{a4}$ and $NR^{a6}R^{a7}$,
$R^{1b}$ is selected independently of one another from OH, SH, COOH, CN, $OCH_2COOH$, halogen, phenyl which optionally has 1, 2 or 3 substituents $R^{1d}$, $C_1$-$C_6$-alkyl, $C_1$-$C_6$-alkoxy, $C_1$-$C_6$-alkylthio, where the alkyl moieties in the last 3 substituents mentioned may be partly or completely halogenated and/or have 1, 2 or 3 substituents $R^{1a}$,
$COOR^{b1}$, $CONR^{b2}R^{b3}$, $SO_2NR^{b2}R^{b3}$, $NR^{b2}$—$SO_2$—$R^{b4}$, $NR^{b2}$—CO—$R^{b5}$, $SO_2$—$R^{b4}$ and $NR^{b6}R^{b7}$,
in addition two $R^{1b}$ radicals may together form a $C_1$-$C_4$-alkylene group, or 2 $R^{1b}$ radicals bonded to adjacent C atoms of cycloalkyl may form together with the carbon atoms to which they are bonded also a benzene ring,
$R^{1c}$ is selected independently of one another from OH, SH, halogen, $NO_2$, $NH_2$, CN, COOH, $OCH_2COOH$, $C_1$-$C_6$-alkyl, $C_1$-$C_6$-alkoxy, $C_1$-$C_6$-alkoxy-$C_1$-$C_4$-alkyl, $C_1$-$C_6$-alkylthio, where the alkyl moieties in the last 4 substituents mentioned may be partly or completely halogenated and/or have 1, 2 or 3 substituents $R^{1a}$,
$C_3$-$C_7$-cycloalkyl, $C_3$-$C_7$-cycloalkyl-$C_1$-$C_4$-alkyl, $C_3$-$C_7$-cycloalkyloxy, where the cycloalkyl moiety of the last three radicals mentioned may have 1, 2, 3 or 4 $R^{1b}$ radicals, and where 1 or 2 $CH_2$-groups in the cycloalkyl moiety may be replaced by O, NH or S, aryl, hetaryl, O-aryl, and O—$CH_2$-aryl, where the last three radicals mentioned are unsubstituted in the aryl moiety or may carry 1, 2, 3 or 4 radicals selected from the group consisting of $R^{1d}$, $COOR^{c1}$, $CONR^{c2}R^{c3}$, $SO_2NR^{c2}R^{c3}$, $NR^{c2}$—$SO_2$—$R^{c4}$, $NR^{c2}$—CO—$R^{c5}$, $SO_2$—$R^{c4}$, —$(CH_2)_p$—$NR^{c6}R^{c7}$ with p=0, 1, 2, 3, 4, 5 or 6, and O—$(CH_2)_q$—$NR^{c6}R^{c7}$ with q=2, 3, 4, 5 or 6; where $R^{a1}$, $R^{b1}$ and $R^{c1}$ are independently H, $C_1$-$C_6$-alkyl, $C_1$-$C_6$-haloalkyl, $C_1$-$C_6$-alkyl which has 1, 2 or 3 substituents independently selected from OH, SH, COOH, CN, $OCH_2COOH$, $C_1$-$C_6$-alkoxy, $C_1$-$C_6$-haloalkoxy, $C_3$-$C_7$-cycloalkyloxy, $C_1$-$C_6$-alkylthio, $C_1$-$C_6$-haloalkylthio, COOH, $C(O)OC_1$-$C_6$-alkyl, $C(O)OC_1$-$C_6$-haloalkyl, $C(O)O$-$C_2$-$C_6$-alkenyl, $C(O)O$-$C_2$-$C_6$-alkynyl, $C(O)O$-$C_3$-$C_7$-cycloalkyl, C(O)O-aryl, C(O)O-hetaryl, $CONH_2$, $CON(H)C_1$-$C_6$-alkyl, $CON(C_1$-$C_6$-alkyl$)_2$, $CON(H)C_1$-$C_6$-haloalkyl, $CON(C_1$-$C_6$-haloalkyl$)_2$, $CON(C_1$-$C_6$-alkyl$)C_1$-$C_6$-haloalkyl, $SO_2NH_2$, $SO_2N(H)C_1$-$C_6$-alkyl, $SO_2N(C_1$-$C_6$-alkyl$)_2$, $SO_2N(H)C_1$-$C_6$-haloalkyl, $SO_2N(C_1$-$C_6$-haloalkyl$)_2$, $SO_2N(C_1$-$C_6$-alkyl$)C_1$-$C_6$-haloalkyl, —NH—$SO_2$—$C_1$-$C_6$-alkyl, —NH—$SO_2$—$C_1$-$C_6$-haloalkyl, —$N(C_1$-$C_6$-alkyl)-$SO_2$—$C_1$-$C_6$-alkyl, —$N(C_1$-$C_6$-alkyl)-$SO_2$—$C_1$-$C_6$-haloalkyl, —$N(C_1$-$C_6$-haloalkyl)-$SO_2$—$C_1$-$C_6$-haloalkyl, —$N(C_1$-$C_6$-haloalkyl)-$SO_2$—$C_1$-$C_6$-alkyl, N(H)—CO—$C_1$-$C_6$-alkyl, N(H)—CO—$C_1$-$C_6$-haloalkyl, $N(C_1$-$C_6$-alkyl)-CO—$C_1$-$C_6$-alkyl, $N(C_1$-$C_6$-haloalkyl)-CO—$C_1$-$C_6$-alkyl, $N(C_1$-$C_6$-haloalkyl)-CO—$C_1$-$C_6$-haloalkyl, $SO_2$—$C_1$-$C_6$-alkyl, $SO_2$—$C_1$-$C_6$-haloalkyl, $NH_2$, $N(H)(C_1$-$C_6$-alkyl), $N(H)(C_1$-$C_6$-haloalkyl), $N(C_1$-$C_6$-alkyl$)_2$, $N(C_1$-$C_6$-alkyl$)(C_1$-$C_6$-haloalkyl), and $N(C_1$-$C_6$-haloalkyl$)_2$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, aryl-$C_1$-$C_4$-alkyl, hetaryl or hetaryl-$C_1$-$C_4$-alkyl, where aryl and hetaryl in the last 4 radicals mentioned are unsubstituted or have 1, 2 or 3 substituents $R^{1d}$, $R^{a2}$, $R^{b2}$ and $R^{c2}$ are independently of one another H, $C_1$-$C_6$-alkyl, $C_1$-$C_6$-haloalkyl, $C_1$-$C_6$-alkyl which has 1, 2 or 3 substituents independently selected from OH, SH, COOH, CN, $OCH_2COOH$, $C_1$-$C_6$-alkoxy, $C_1$-$C_6$-haloalkoxy, $C_3$-$C_7$-cycloalkyloxy, $C_1$-$C_6$-alkylthio, $C_1$-$C_6$-haloalkylthio, COOH, $C(O)OC_1$-$C_6$-alkyl, $C(O)OC_1$-$C_6$-haloalkyl, $C(O)O$-$C_2$-$C_6$-alkenyl, $C(O)O$-$C_2$-$C_6$-alkynyl, $C(O)O$-$C_3$-$C_7$-cycloalkyl, C(O)O-aryl, C(O)O-hetaryl, $CONH_2$, $CON(H)C_1$-$C_6$-alkyl, $CON(C_1$-$C_6$-alkyl$)_2$, $CON(H)C_1$-$C_6$-haloalkyl, $CON(C_1$-$C_6$-haloalkyl$)_2$, $CON(C_1$-$C_6$-alkyl$)C_1$-$C_6$-haloalkyl, $SO_2NH_2$, $SO_2N(H)C_1$-$C_6$-alkyl, $SO_2N(C_1$-$C_6$-alkyl$)_2$, $SO_2N(H)C_1$-$C_6$-haloalkyl, $SO_2N(C_1$-$C_6$-haloalkyl$)_2$, $SO_2N(C_1$-$C_6$-alkyl$)C_1$-$C_6$-haloalkyl, —NH—$SO_2$—$C_1$-$C_6$-alkyl, —NH—$SO_2$—$C_1$-$C_6$-haloalkyl, —$N(C_1$-$C_6$-alkyl)-$SO_2$—$C_1$-$C_6$-alkyl, —$N(C_1$-$C_6$-alkyl)-$SO_2$—$C_1$-$C_6$-haloalkyl, —$N(C_1$-$C_6$-haloalkyl)-$SO_2$—$C_1$-$C_6$-haloalkyl, —$N(C_1$-$C_6$-haloalkyl)-$SO_2$—$C_1$-$C_6$-alkyl, N(H)—CO—$C_1$-$C_6$-alkyl, N(H)—CO—$C_1$-$C_6$-haloalkyl, $N(C_1$-$C_6$-alkyl)-CO—$C_1$-$C_6$-alkyl, $N(C_1$-$C_6$-haloalkyl)-CO—$C_1$-$C_6$-alkyl, $N(C_1$-$C_6$-haloalkyl)-CO—$C_1$-$C_6$-haloalkyl, $SO_2$—$C_1$-$C_6$-alkyl, $SO_2$—$C_1$-$C_6$-haloalkyl, $NH_2$, $N(H)(C_1$-$C_6$-alkyl), $N(H)(C_1$-$C_6$-haloalkyl), $N(C_1$-$C_6$-alkyl$)_2$, $N(C_1$-$C_6$-alkyl$)(C_1$-$C_6$-haloalkyl), and $N(C_1$-$C_6$-haloalkyl$)_2$; $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, aryl-$C_1$-$C_4$-alkyl, hetaryl, or hetaryl-$C_1$-$C_4$-alkyl, where aryl and hetaryl in the last 4 radicals mentioned are unsubstituted or have 1, 2 or 3 substituents $R^{1d}$, and $R^{a3}$, $R^{b3}$ and $R^{c3}$ are independently of one another H, $C_1$-$C_6$-alkyl, $C_1$-$C_6$-haloalkyl, $C_1$-$C_6$-alkyl which has 1, 2 or 3 substituents independently selected from OH, SH, COOH, CN, $OCH_2COOH$, $C_1$-$C_6$-alkoxy, $C_1$-$C_6$-haloalkoxy, $C_3$-$C_7$-cycloalkyloxy, $C_1$-$C_6$-alkylthio, $C_1$-$C_6$-haloalkylthio, COOH, $C(O)OC_1$-$C_6$-alkyl, $C(O)OC_1$-$C_6$-haloalkyl, $C(O)O$-$C_2$-$C_6$-alkenyl, $C(O)O$-$C_2$-$C_6$-alkynyl, $C(O)O$-$C_3$-$C_7$-cycloalkyl, C(O)O-aryl, C(O)O-hetaryl, $CONH_2$, $CON(H)C_1$-$C_6$-alkyl, $CON(C_1$-$C_6$-alkyl$)_2$, $CON(H)C_1$-$C_6$-haloalkyl, $CON(C_1$-$C_6$-haloalkyl$)_2$, $CON(C_1$-$C_6$-alkyl$)C_1$-$C_6$-haloalkyl, $SO_2NH_2$, $SO_2N(H)C_1$-$C_6$-alkyl, $SO_2N(C_1$-$C_6$-alkyl$)_2$, $SO_2N(H)C_1$-$C_6$-haloalkyl, $SO_2N(C_1$-$C_6$-haloalkyl$)_2$, $SO_2N(C_1$-$C_6$-alkyl$)C_1$-$C_6$-haloalkyl, —NH—$SO_2$—$C_1$-$C_6$-alkyl, —NH—$SO_2$—$C_1$-$C_6$-haloalkyl, —$N(C_1$-$C_6$-alkyl)-$SO_2$—$C_1$-$C_6$-alkyl, —$N(C_1$-$C_6$-alkyl)-$SO_2$—$C_1$-$C_6$-haloalkyl, —$N(C_1$-$C_6$-haloalkyl)-$SO_2$—$C_1$-$C_6$-haloalkyl, —$N(C_1$-$C_6$-haloalkyl)-$SO_2$—$C_1$-$C_6$-alkyl, N(H)—CO—$C_1$-$C_6$-alkyl, N(H)—CO—$C_1$-$C_6$-haloalkyl, $N(C_1$-$C_6$-alkyl)-CO—$C_1$-$C_6$-alkyl, $N(C_1$-$C_6$-haloalkyl)-CO—$C_1$-$C_6$-alkyl, $N(C_1$-$C_6$-haloalkyl)-CO—$C_1$-$C_6$-haloalkyl, $SO_2$—$C_1$-$C_6$-alkyl, $SO_2$—$C_1$-$C_6$-haloalkyl, $NH_2$, $N(H)(C_1$-$C_6$-alkyl), $N(H)(C_1$-$C_6$-haloalkyl), $N(C_1$-$C_6$-alkyl$)_2$, $N(C_1$-$C_6$-alkyl$)(C_1$-$C_6$-haloalkyl), and $N(C_1$-$C_6$-haloalkyl$)_2$; $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, aryl-$C_1$-$C_4$-alkyl, hetaryl, or hetaryl-$C_1$-$C_4$-alkyl, where aryl and hetaryl in the last 4 radicals mentioned are unsubstituted or have 1, 2 or 3 substituents $R^{1d}$, or the two radicals $R^{a2}$ and $R^{a3}$, or $R^{b2}$ and $R^{b3}$, or $R^{c2}$ and $R^{c3}$, form together with the N atom a 3 to 7-membered, optionally substituted nitrogen heterocycle which may optionally have 1, 2 or 3 further different or identical heteroatoms selected from the group consisting of O, N, and S as ring members, $R^{a4}$, $R^{b4}$ and $R^{c4}$ are independently of one another $C_1$-$C_6$-alkyl, $C_1$-$C_6$-haloalkyl, $C_1$-$C_6$-alkyl which has 1, 2 or 3 substituents independently selected from OH, SH, COOH, CN, $OCH_2COOH$, $C_1$-$C_6$-alkoxy, $C_1$-$C_6$-haloalkoxy, $C_3$-$C_7$-cycloalkyloxy, $C_1$-$C_6$-alkylthio, $C_1$-$C_6$-haloalkylthio, COOH, $C(O)OC_1$-$C_6$-alkyl, $C(O)OC_1$-$C_6$-haloalkyl, $C(O)O$-$C_2$-$C_6$-alkenyl, $C(O)O$-$C_2$-$C_6$-alkynyl, $C(O)O$-$C_3$-$C_7$-cycloalkyl, C(O)O-aryl, C(O)O-hetaryl, $CONH_2$, $CON(H)C_1$-$C_6$-alkyl, $CON(C_1$-$C_6$-alkyl$)_2$, $CON(H)C_1$-$C_6$-haloalkyl, $CON(C_1$-$C_6$-haloalkyl$)_2$, $CON(C_1$-$C_6$-alkyl$)C_1$-$C_6$-haloalkyl, $SO_2NH_2$, $SO_2N(H)C_1$-$C_6$-alkyl, $SO_2N(C_1$-$C_6$-alkyl$)_2$, $SO_2N(H)C_1$-$C_6$-haloalkyl, $SO_2N(C_1$-$C_6$-haloalkyl$)_2$, $SO_2N(C_1$-$C_6$-alkyl$)C_1$-$C_6$-haloalkyl, —NH—$SO_2$—$C_1$-$C_6$-alkyl, —NH—$SO_2$—$C_1$-$C_6$-haloalkyl, —$N(C_1$-$C_6$-alkyl)-

SO$_2$—C$_1$-C$_6$-alkyl, —N(C$_1$-C$_6$-alkyl)-SO$_2$—C$_1$-C$_6$-haloalkyl, —N(C$_1$-C$_6$-haloalkyl)-SO$_2$—C$_1$-C$_6$-haloalkyl, —N(C$_1$-C$_6$-haloalkyl)-SO$_2$—C$_1$-C$_6$-alkyl, N(H)—CO—C$_1$-C$_6$-alkyl, N(H)—CO—C$_1$-C$_6$-haloalkyl, N(C$_1$-C$_6$-alkyl)-CO—C$_1$-C$_6$-alkyl, N(C$_1$-C$_6$-haloalkyl)-CO—C$_1$-C$_6$-alkyl, N(C$_1$-C$_6$-haloalkyl)-CO—C$_1$-C$_6$-haloalkyl, SO$_2$—C$_1$-C$_6$-alkyl, SO$_2$—C$_1$-C$_6$-haloalkyl, NH$_2$, N(H)(C$_1$-C$_6$-alkyl), N(H)(C$_1$-C$_6$-haloalkyl), N(C$_1$-C$_6$-alkyl)$_2$, N(C$_1$-C$_6$-alkyl)(C$_1$-C$_6$-haloalkyl), and N(C$_1$-C$_6$-haloalkyl)$_2$; C$_2$-C$_6$-alkenyl, C$_2$-C$_6$-alkynyl, C$_3$-C$_7$-cycloalkyl, C$_3$-C$_7$-cycloalkyl-C$_1$-C$_4$-alkyl, C$_3$-C$_7$-heterocycloalkyl-C$_1$-C$_4$-alkyl, C$_1$-C$_6$-alkoxy-C$_1$-C$_4$-alkyl, aryl, aryl-C$_1$-C$_4$-alkyl, hetaryl, or hetaryl-C$_1$-C$_4$-alkyl, where aryl and hetaryl in the last 4 radicals mentioned are unsubstituted or have 1, 2 or 3 substituents R$^{1d}$, and R$^{a5}$, R$^{b5}$ and R$^{c5}$ have independently of one another one of the meanings mentioned for R$^{a1}$, R$^{b1}$ and R$^{c1}$;

R$^{a6}$, R$^{b6}$ and R$^{c6}$ are independently of one another H, C$_1$-C$_6$-alkyl, C$_1$-C$_6$-alkoxy, C$_1$-C$_6$-haloalkyl, C$_1$-C$_6$-alkyl which has 1, 2 or 3 substituents independently selected from OH, SH, COOH, CN, OCH$_2$COOH, C$_1$-C$_6$-alkoxy, C$_1$-C$_6$-haloalkoxy, C$_3$-C$_7$-cycloalkyloxy, C$_1$-C$_6$-alkylthio, C$_1$-C$_6$-haloalkylthio, COOH, C(O)OC$_1$-C$_6$-alkyl, C(O)OC$_1$-C$_6$-haloalkyl, C(O)O—C$_2$-C$_6$-alkenyl, C(O)O—C$_2$-C$_6$-alkynyl, C(O)O—C$_3$-C$_7$-cycloalkyl, C(O)O-aryl, C(O)O-hetaryl, CONH$_2$, CON(H)C$_1$-C$_6$-alkyl, CON(C$_1$-C$_6$-alkyl)$_2$, CON(H)C$_1$-C$_6$-haloalkyl, CON(C$_1$-C$_6$-haloalkyl)$_2$, CON(C$_1$-C$_6$-alkyl)C$_1$-C$_6$-haloalkyl, SO$_2$NH$_2$, SO$_2$N(H)C$_1$-C$_6$-alkyl, SO$_2$N(C$_1$-C$_6$-alkyl)$_2$, SO$_2$N(H)C$_1$-C$_6$-haloalkyl, SO$_2$N(C$_1$-C$_6$-haloalkyl)$_2$, SO$_2$N(C$_1$-C$_6$-alkyl)C$_1$-C$_6$-haloalkyl, —NH—SO$_2$—C$_1$-C$_6$-alkyl, —NH—SO$_2$—C$_1$-C$_6$-haloalkyl, —N(C$_1$-C$_6$-alkyl)-SO$_2$—C$_1$-C$_6$-alkyl, —N(C$_1$-C$_6$-alkyl)-SO$_2$—C$_1$-C$_6$-haloalkyl, —N(C$_1$-C$_6$-haloalkyl)-SO$_2$—C$_1$-C$_6$-haloalkyl, —N(C$_1$-C$_6$-haloalkyl)-SO$_2$—C$_1$-C$_6$-alkyl, N(H)—CO—C$_1$-C$_6$-alkyl, N(H)—CO—C$_1$-C$_6$-haloalkyl, N(C$_1$-C$_6$-alkyl)-CO—C$_1$-C$_6$-alkyl, N(C$_1$-C$_6$-haloalkyl)-CO—C$_1$-C$_6$-alkyl, N(C$_1$-C$_6$-haloalkyl)-CO—C$_1$-C$_6$-haloalkyl, SO$_2$—C$_1$-C$_6$-alkyl, SO$_2$—C$_1$-C$_6$-haloalkyl, NH$_2$, N(H)(C$_1$-C$_6$-alkyl), N(H)(C$_1$-C$_6$-haloalkyl), N(C$_1$-C$_6$-alkyl)$_2$, N(C$_1$-C$_6$-alkyl)(C$_1$-C$_6$-haloalkyl), and N(C$_1$-C$_6$-haloalkyl)$_2$; C$_2$-C$_6$-alkenyl, C$_2$-C$_6$-alkynyl, C$_3$-C$_7$-cycloalkyl, C$_3$-C$_7$-cycloalkyl-C$_1$-C$_4$-alkyl, C$_3$-C$_7$-heterocycloalkyl-C$_1$-C$_4$-alkyl, C$_1$-C$_6$-alkoxy-C$_1$-C$_4$-alkyl, CO—C$_1$-C$_6$-alkyl, CO—O—C$_1$-C$_6$-alkyl, SO$_2$—C$_1$-C$_6$-alkyl, aryl, hetaryl, O-aryl, OCH$_2$-aryl, aryl-C$_1$-C$_4$-alkyl, hetaryl-C$_1$-C$_4$-alkyl, CO-aryl, CO-hetaryl, CO-(aryl-C$_1$-C$_4$-alkyl), CO-(hetaryl-C$_1$-C$_4$-alkyl), CO—O-aryl, CO—O-hetaryl, CO—O-(aryl-C$_1$-C$_4$-alkyl), CO—O-(hetaryl-C$_1$-C$_4$-alkyl), SO$_2$-aryl, SO$_2$-hetaryl, SO$_2$—(aryl-C$_1$-C$_4$-alkyl) or SO$_2$—(hetaryl-C$_1$-C$_4$-alkyl), where aryl and hetaryl in the last 18 radicals mentioned are unsubstituted or have 1, 2 or 3 substituents R$^{1d}$, and R$^{a7}$, R$^{b7}$ and R$^{c7}$ are independently of one another H, C$_1$-C$_6$-alkyl, C$_1$-C$_6$-haloalkyl, C$_1$-C$_6$-alkyl which has 1, 2 or 3 substituents independently selected from OH, SH, COOH, CN, OCH$_2$COOH, C$_1$-C$_6$-alkoxy, C$_1$-C$_6$-haloalkoxy, C$_3$-C$_7$-cycloalkyloxy, C$_1$-C$_6$-alkylthio, C$_1$-C$_6$-haloalkylthio, COOH, C(O)OC$_1$-C$_6$-alkyl, C(O)OC$_1$-C$_6$-haloalkyl, C(O)O-C$_2$-C$_6$-alkenyl, C(O)O-C$_2$-C$_6$-alkynyl, C(O)O-C$_3$-C$_7$-cycloalkyl, C(O)O-aryl, C(O)O-hetaryl, CONH$_2$, CON(H)C$_1$-C$_6$-alkyl, CON(C$_1$-C$_6$-alkyl)$_2$, CON(H)C$_1$-C$_6$-haloalkyl, CON(C$_1$-C$_6$-haloalkyl)$_2$, CON(C$_1$-C$_6$-alkyl)C$_1$-C$_6$-haloalkyl, SO$_2$NH$_2$, SO$_2$N(H)C$_1$-C$_6$-alkyl, SO$_2$N(C$_1$-C$_6$-alkyl)$_2$, SO$_2$N(H)C$_1$-C$_6$-haloalkyl, SO$_2$N(C$_1$-C$_6$-haloalkyl)$_2$, SO$_2$N(C$_1$-C$_6$-alkyl)C$_1$-C$_6$-haloalkyl, —NH—SO$_2$—C$_1$-C$_6$-alkyl, —NH—SO$_2$—C$_1$-C$_6$-haloalkyl, —N(C$_1$-C$_6$-alkyl)-SO$_2$—C$_1$-C$_6$-alkyl, —N(C$_1$-C$_6$-alkyl)-SO$_2$—C$_1$-C$_6$-haloalkyl, —N(C$_1$-C$_6$-haloalkyl)-SO$_2$—C$_1$-C$_6$-haloalkyl, —N(C$_1$-C$_6$-haloalkyl)-SO$_2$—C$_1$-C$_6$-alkyl, N(H)—CO—C$_1$-C$_6$-alkyl, N(H)—CO—C$_1$-C$_6$-haloalkyl, N(C$_1$-C$_6$-alkyl)-CO—C$_1$-C$_6$-alkyl, N(C$_1$-C$_6$-haloalkyl)-CO—C$_1$-C$_6$-alkyl, N(C$_1$-C$_6$-haloalkyl)-CO—C$_1$-C$_6$-haloalkyl, SO$_2$—C$_1$-C$_6$-alkyl, SO$_2$—C$_1$-C$_6$-haloalkyl, NH$_2$, N(H)(C$_1$-C$_6$-alkyl), N(H)(C$_1$-C$_6$-haloalkyl), N(C$_1$-C$_6$-alkyl)$_2$, N(C$_1$-C$_6$-alkyl)(C$_1$-C$_6$-haloalkyl), and N(C$_1$-C$_6$-haloalkyl)$_2$; C$_2$-C$_6$-alkenyl, C$_2$-C$_6$-alkynyl, C$_3$-C$_7$-cycloalkyl, C$_3$-C$_7$-cycloalkyl-C$_1$-C$_4$-alkyl, C$_3$-C$_7$-heterocycloalkyl-C$_1$-C$_4$-alkyl, C$_1$-C$_6$-alkoxy-C$_1$-C$_4$-alkyl, aryl, aryl-C$_1$-C$_4$-alkyl, hetaryl, or hetaryl-C$_1$-C$_4$-alkyl, where aryl and hetaryl in the last 4 radicals mentioned are unsubstituted or have 1, 2 or 3 substituents R$^{1d}$, or the two radicals R$^{a6}$ and R$^{b7}$, or R$^{b6}$ and R$^{b7}$, or R$^{c6}$ and R$^{c7}$, form together with the N atom a 3- to 7-membered, optionally substituted nitrogen heterocycle which may optionally have 1, 2 or 3 further different or identical heteroatoms selected from the group consisting of O, N, and S as ring members, or two radicals R$^{1b}$ or R$^{1c}$ bonded to adjacent C atoms form together with the C atoms to which they are bonded a 4-, 5-, 6- or 7-membered, optionally substituted carbocycle or an optionally substituted heterocycle which has 1, 2 or 3 different or identical heteroatoms from the group of O, N, and S as ring members;

R$^{1d}$ is selected from halogen, OH, SH, NO$_2$, COOH, C(O)NH$_2$, CHO, CN, NH$_2$, OCH$_2$COOH, C$_1$-C$_6$-alkyl, C$_1$-C$_6$-haloalkyl, C$_1$-C$_6$-alkoxy, C$_1$-C$_6$-haloalkoxy, C$_1$-C$_6$-alkylthio, C$_1$-C$_6$-haloalkylthio, CO—C$_1$-C$_6$-alkyl, CO—O—C$_1$-C$_6$-alkyl, NH—C$_1$-C$_6$-alkyl, NHCHO, NH—C(O)C$_1$-C$_6$-alkyl, and SO$_2$—C$_1$-C$_6$-alkyl;

R$^2$ is C$_3$-C$_7$-cycloalkyl, C$_3$-C$_7$-cycloalkyl-C$_1$-C$_4$-alkyl, where a CH$_2$ group in the cycloalkyl moiety of the last two radicals mentioned may be replaced by O, NH, or S, or two adjacent C atoms may form a double bond, where the cycloalkyl moiety may additionally have 1, 2, 3 or 4 R$^{2a}$ radicals;

aryl, O-aryl, O—CH$_2$-aryl, hetaryl, aryl-C$_1$-C$_6$-alkyl, aryl-C$_2$-C$_6$-alkenyl, hetaryl-C$_1$-C$_4$-alkyl or hetaryl-C$_2$-C$_6$-alkenyl, where aryl and hetaryl in the last 8 radicals mentioned may be unsubstituted or carry 1, 2, 3 or 4 identical or different R$^{2b}$ radicals; where R$^{2a}$ has one of the meanings indicated for R$^{1b}$, and R$^{2b}$ has one of the meanings indicated for R$^{1c}$;

R$^{3a}$ and R$^{3b}$ are independently of one another hydroxy or C$_1$-C$_4$-alkoxy, or together with the carbon atom to which they are bonded are C=O; or R$^{3a}$ and R$^{3b}$ together form a moiety S-Alk-S, O-Alk-S or O-Alk-O, wherein Alk is linear C$_2$-C$_5$-alkandiyl, which may be unsubstituted or substituted with 1, 2, 3 or 4 radicals selected from C$_1$-C$_4$-alkyl or halogen;

X is hydrogen or a radical of the formulae C(=O)—O—R$^{x1}$, C(=O)—NR$^{x2}$R$^{x3}$, C(=O)—N(R$^{x4}$)—(C$_1$-C$_6$-alkylene)-NR$^{x2}$R$^{x3}$ or C(=O)—N(R$^{x4}$)NR$^{x2}$R$^{x3}$, in which R$^{x1}$ is hydrogen, C$_1$-C$_6$-alkyl, C$_1$-C$_6$-haloalkyl, C$_1$-C$_6$-alkyl which has 1, 2 or 3 substituents R$^{xa}$, C$_2$-C$_6$-alkenyl, C$_2$-C$_6$-alkynyl, C$_3$-C$_7$-cycloalkyl, C$_3$-C$_7$-cycloalkyl-C$_1$-C$_4$-alkyl, C$_3$-C$_7$-heterocycloalkyl-C$_1$-C$_4$-alkyl, C$_1$-C$_6$-alkoxy-C$_1$-C$_4$-alkyl, where alkyl, alkenyl, alkoxy, alkynyl, cycloalkyl, heterocycloalkyl in the last 6 radicals mentioned are unsubstituted or have 1, 2 or 3 substituents R$^{xa}$, or aryl, aryl-C$_1$-C$_4$-alkyl, hetaryl or hetaryl-C$_1$-C$_4$-alkyl, where aryl and hetaryl in the last 4 radicals mentioned are unsubstituted or have 1, 2 or 3 substituents R$^{xd}$, R$^{x2}$ is H, OH, CN, C$_1$-C$_6$-alkyl, C$_1$-C$_6$-haloalkyl, C$_1$-C$_6$-alkyl which has 1, 2 or 3 substituents R$^{xa}$, C$_2$-C$_6$-alkenyl, C$_2$-C$_6$-alkynyl, C$_3$-C$_7$-cycloalkyl, C$_3$-C$_7$-cycloalkyl-C$_1$-C$_4$-alkyl, C$_3$-C$_7$-heterocycloalkyl-C$_1$-C$_4$-alkyl, C$_1$-C$_6$-alkoxy-C$_1$-C$_4$-alkyl, CO—C$_1$-C$_6$-alkyl, CO—O—C$_1$-C$_6$-alkyl, SO$_2$—C$_1$-C$_6$-alkyl, or O—C$_1$-C$_6$-alkyl, where alkyl, alkoxy, alkenyl, alkynyl, cycloalkyl, and heterocycloalkyl in the last 10 radicals mentioned are unsubstituted or have 1, 2 or 3 substituents R$^{xa}$, aryl, O-aryl, O—CH$_2$-aryl, hetaryl, O—CH$_2$-hetaryl, aryl-C$_1$-C$_4$-alkyl, hetaryl-C$_1$-C$_4$-alkyl, CO-aryl, CO-hetaryl, CO-(aryl-C$_1$-C$_4$-alkyl), CO-(hetaryl-C$_1$-C$_4$-alkyl), CO—O-aryl, CO—O-hetaryl, CO—O-(aryl-C$_1$-C$_4$-alkyl), CO—O-(hetaryl-C$_1$-C$_4$-alkyl), SO$_2$-aryl, SO$_2$-hetaryl, SO$_2$—(aryl-C$_1$-C$_4$-alkyl) or SO$_2$-(hetaryl-C$_1$-C$_4$-alkyl), where aryl and hetaryl in the last 19 radicals mentioned are unsubstituted or have 1, 2 or 3 substituents R$^{xd}$, R$^{x3}$ is H, C$_1$-C$_6$-alkyl, C$_1$-C$_6$-haloalkyl, C$_1$-C$_6$-alkyl which has 1, 2 or 3 substituents R$^{xa}$, C$_2$-C$_6$-alkenyl, C$_2$-C$_6$-alkynyl, C$_3$-C$_7$-cycloalkyl, C$_3$-C$_7$-cycloalkyl-C$_1$-C$_4$-alkyl, C$_3$-C$_7$-heterocycloalkyl-C$_1$-C$_4$-alkyl, C$_1$-C$_6$-alkoxy-C$_1$-C$_4$-alkyl, where alkyl, alkenyl, alkoxy, alkynyl, cycloalkyl, heterocycloalkyl in the last 6 radicals mentioned are unsubstituted or have 1, 2 or 3 substituents R$^{xa}$, aryl, aryl-C$_1$-C$_4$-alkyl, hetaryl or hetaryl-C$_1$-C$_4$-alkyl, where aryl and hetaryl in the last 4 radicals mentioned are unsubstituted or have 1, 2 or 3 substituents R$^{xd}$, or the two radicals R$^{x2}$ and R$^{x3}$ form together with the N atom a 3- to 7-membered nitrogen heterocycle which may optionally have 1, 2 or 3 further different or identical heteroatoms selected from the group consisting of O, N, S as ring members, and which may have 1, 2 or 3 substituents R$^{xb}$, and R$^{x4}$ is H, OH, CN, C$_1$-C$_6$-alkyl, C$_1$-C$_6$-haloalkyl, C$_1$-C$_6$-alkyl which has 1, 2 or 3 substituents R$^{xa}$, C$_2$-C$_6$-alkenyl, C$_2$-C$_6$-alkynyl, C$_3$-C$_7$-cycloalkyl, C$_3$-C$_7$-cycloalkyl-C$_1$-C$_4$-alkyl, C$_3$-C$_7$-heterocycloalkyl-C$_1$-C$_4$-alkyl, C$_1$-C$_6$-alkoxy-C$_1$-C$_4$-alkyl, CO—C$_1$-C$_6$-alkyl, CO—O—C$_1$-C$_6$-alkyl, or SO$_2$—C$_1$-C$_6$-alkyl, where alkyl, alkenyl, alkoxy, alkynyl, cycloalkyl, heterocycloalkyl in the last 9 radicals mentioned are unsubstituted or have 1, 2 or 3 substituents R$^{xa}$, aryl, O-aryl, O—CH$_2$-aryl, hetaryl, aryl-C$_1$-C$_4$-alkyl, hetaryl-C$_1$-C$_4$-alkyl, CO-aryl, CO-hetaryl, CO-(aryl-C$_1$-C$_4$-alkyl), CO-(hetaryl-C$_1$-C$_4$-alkyl), CO—O-aryl, CO—O-hetaryl, CO—O-(aryl-C$_1$-C$_4$-alkyl), CO—O-(hetaryl-C$_1$-C$_4$-alkyl), SO$_2$-aryl, SO$_2$-hetaryl, SO$_2$-(aryl-C$_1$-C$_4$-alkyl) or SO$_2$-(hetaryl-C$_1$-C$_4$-alkyl), where aryl and hetaryl in the last 18 radicals mentioned are unsubstituted or have 1, 2 or 3 substituents R$^{xd}$, and where R$^{xa}$ has one of the meanings indicated for R$^{1a}$, R$^{xb}$ has one of the meanings indicated for R$^{1b}$, and R$^{xd}$ has one of the meanings indicated for R$^{1d}$;

Y$^1$, Y$^2$, Y$^3$ or Y$^4$ are CR$^y$, or one or two of the variables Y$^1$, Y$^2$, Y$^3$ or Y$^4$ are a nitrogen atom, and the remaining variables Y$^1$, Y$^2$, Y$^3$ or Y$^4$ are CR$^y$;

R$^y$ is selected independently of one another from hydrogen, OH, SH, halogen, NO$_2$, NH$_2$, CN, CF$_3$, CHF$_2$, CH$_2$F, O—CF$_3$, O—CHF$_2$, O—CH$_2$F, COOH, OCH$_2$COOH, C$_1$-C$_6$-alkyl, C$_1$-C$_6$-alkoxy, C$_1$-C$_6$-alkoxy-C$_1$-C$_4$-alkyl, C$_1$-C$_6$-alkylthio, where the last 4 radicals mentioned may be partly or completely halogenated and/or have 1, 2 or 3 substituents R$^{ya}$, C$_3$-C$_7$-cycloalkyl, C$_3$-C$_7$-cycloalkyl-C$_1$-C$_4$-alkyl, C$_3$-C$_7$-cycloalkyl-O, where the cycloalkyl moiety in the last three radicals mentioned may have 1, 2, 3 or 4 R$^{yb}$ radicals, and where 1 or 2 CH$_2$-groups in the cycloalkyl moiety may be replaced by O, NH or S, aryl, hetaryl, O-aryl, CH$_2$-aryl, or O—CH$_2$-aryl, where the last 4 radicals mentioned are unsubstituted in the aryl moiety or may carry 1, 2, 3 or 4 radicals selected from the group consisting of R$^{yd}$, COOR$^{y1}$, CONR$^{y2}$R$^{y3}$, SO$_2$NR$^{y2}$R$^{y3}$, —NH—SO$_2$—R$^{y4}$, NH—CO—R$^{y5}$, SO$_2$—R$^{y4}$, —(CH$_2$)$_p$—NR$^{y6}$R$^{y7}$ with p=0, 1, 2, 3, 4, 5 or 6, and O—(CH$_2$)$_q$—NR$^{y6}$R$^{y7}$ with q=2, 3, 4, 5 or 6;

or two R$^y$ radicals bonded to adjacent C atoms form together with the C atoms to which they are bonded a 4-, 5-, 6- or 7-membered, optionally substituted carbocycle or an optionally substituted heterocycle which has 1, 2 or 3 different or identical heteroatoms selected from the group consisting of O, N, and S as ring members, where R$^{ya}$ has one of the meanings indicated for R$^{1a}$,
    R$^{yb}$ has one of the meanings indicated for R$^{1b}$,
    R$^{yd}$ has one of the meanings indicated for R$^{1d}$,
    R$^{y1}$ has one of the meanings indicated for R$^{c1}$,
    R$^{y2}$ has one of the meanings indicated for R$^{c2}$,
    R$^{y3}$ has one of the meanings indicated for R$^{c3}$,
    R$^{y4}$ has one of the meanings indicated for R$^{c4}$,
    R$^{y5}$ has one of the meanings indicated for R$^{c5}$,
    R$^{y6}$ has one of the meanings indicated for R$^{c6}$, and
    R$^{y7}$ has one of the meanings indicated for R$^{c7}$;

W is a radical of the formulae W1 or W2:

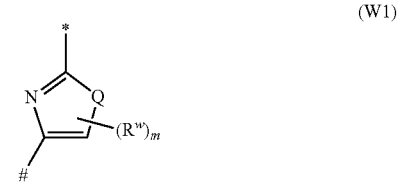

(W1)

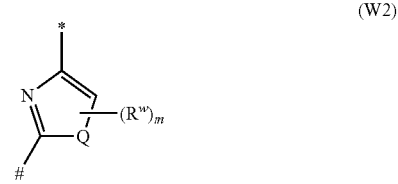

(W2)

in which
* means the linkage to the 6-membered aromatic ring, and # means the linkage to R$^2$,
m is 0 or 1,
Q is O, S or NR$^{ww}$,
R$^w$ is selected from OH, SH, halogen, NO$_2$, NH$_2$, CN, COOH, OCH$_2$COOH, C$_1$-C$_6$-alkyl, C$_1$-C$_6$-alkoxy, C$_1$-C$_6$-alkoxy-C$_1$-C$_4$-alkyl, C$_1$-C$_6$-alkylthio, where the last 4 radicals mentioned may be partly or completely halogenated and/or have 1, 2 or 3 substituents $R^{wa}$, $C_3$-$C_7$-cycloalkyl, $C_3$-$C_7$-cycloalkyl-$C_1$-$C_4$-alkyl, $C_3$-$C_7$-cycloalkyloxy, where the cycloalkyl moiety of the last three radicals mentioned may have 1, 2, 3 or 4 radicals $R^{wb}$, aryl, O-aryl, O—$CH_2$-aryl, or hetaryl, where the last four radicals mentioned are unsubstituted in the aryl moiety or may carry 1, 2, 3 or 4 radicals selected from the group consisting of $R^{wd}$, $COOR^{w1}$, $CONR^{w2}R^{w3}$, $SO_2NR^{w2}R^{w3}$, $NR^{w2}$—$SO_2$—$R^{w4}$, $NR^{w2}$—CO—$R^{w5}$, $SO_2$—$R^{w4}$, —$(CH_2)_p$—$NR^{w6}R^{w7}$ with p=0, 1, 2, 3, 4, 5 or 6, and O—$(CH_2)_q$—$NR^{w6}R^{w7}$ with q=2, 3, 4, 5 or 6;

or two $R^w$ radicals bonded to adjacent C atoms form together with the C atoms to which they are bonded a 4, 5, 6 or 7-membered, optionally substituted carbocycle or an optionally substituted heterocycle which has 1, 2 or 3 different or identical heteroatoms selected from the group consisting of O, N, and S as ring members, where $R^{wa}$ has one of the meanings indicated for $R^{1a}$,
$R^{wb}$ has one of the meanings indicated for $R^{1b}$,
$R^{wd}$ has one of the meanings indicated for $R^{1d}$,
$R^{w1}$ has one of the meanings indicated for $R^{1d}$,
$R^{w2}$ has one of the meanings indicated for $R^{c2}$,
$R^{w3}$ has one of the meanings indicated for $R^{c3}$,
$R^{w4}$ has one of the meanings indicated for $R^{c4}$,
$R^{w5}$ has one of the meanings indicated for $R^{c5}$,
$R^{w6}$ has one of the meanings indicated for $R^{c6}$,
$R^{w7}$ has one of the meanings indicated for $R^{c7}$, $R^{ww}$ is selected from H, OH, $NH_2$, CN, $CF_3$, $CHF_2$, $CH_2F$, O—$CF_3$, O—$CHF_2$, O—$CH_2F$, COOH, $OCH_2COOH$, $C_1$-$C_6$-alkyl, $C_1$-$C_6$-alkoxy, $C_1$-$C_6$-alkoxy-$C_1$-$C_4$-alkyl, where the last 4 radicals mentioned may be partly or completely halogenated and/or have 1, 2 or 3 substituents $R^{wa}$, $C_3$-$C_7$-cycloalkyl, $C_3$-$C_7$-cycloalkyl-$C_1$-$C_4$-alkyl, $C_3$-$C_7$-cycloalkyloxy, where the cycloalkyl moiety of the last three radicals mentioned may have 1, 2, 3 or 4 radicals $R^{wb}$, aryl, O-aryl, O—$CH_2$-aryl, hetaryl, where the last four radicals mentioned are unsubstituted in the aryl moiety or may carry 1, 2, 3 or 4 radicals selected from the group consisting of $R^{wd}$, $COOR^{w1}$, $CONR^{w2}R^{w3}$, $SO_2NR^{w2}R^{w3}$, $NR^{w2}$—$SO_2$—$R^{w4}$, $NR^{w2}$—CO—$R^{w5}$, $SO_2$—$R^{w4}$, —$(CH_2)_p$—$NR^{w6}R^{w7}$ with p=0, 1, 2, 3, 4, 5 or 6, and O—$(CH_2)_q$—$NR^{w6}R^{w7}$ with q=2, 3, 4, 5 or 6;

or

W forms together with $R^2$ a radical of the formula W3:

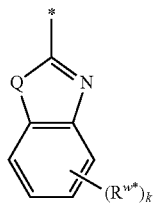

(W3)

in which

* means the linkage to the 6-membered aromatic ring,

Q has one of the meanings indicated for Q in formula W1, k is 0, 1 or 2, and $R^{w*}$ has one of the meanings indicated for $R^w$, or a tautomer thereof, or a pharmaceutically suitable salt thereof.

2. The carboxamide compound of claim 1, in which m is 0.

3. The carboxamide compound of claim 1, in which X in the formula I is a C(=O)—$NR^{x2}R^{x3}$ radical in which $R^{x2}$ is H, OH, CN, $C_1$-$C_6$-alkyl, $C_1$-$C_6$-haloalkyl, $C_1$-$C_6$-alkyl which has 1, 2 or 3 substituents $R^{xa}$, $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, hetaryl, aryl-$C_1$-$C_4$-alkyl, or hetaryl-$C_1$-$C_4$-alkyl, where aryl and hetaryl in the last 4 radicals mentioned are unsubstituted or have 1, 2 or 3 substituents $R^{xd}$, and $R^{x3}$ is H, $C_1$-$C_6$-alkyl, $C_1$-$C_6$-haloalkyl, or $C_1$-$C_6$-alkyl which has 1, 2 or 3 substituents $R^{xa}$, or $NR^{x2}R^{x3}$ is a nitrogen heterocycle of the following formulae:

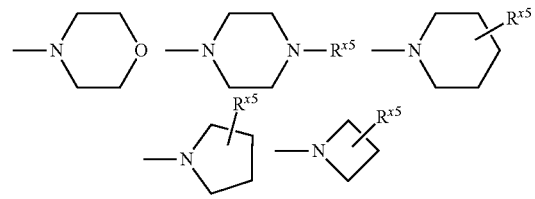

in which $R^{x5}$ is hydrogen or has the meaning indicated in claim 1 for $R^{xb}$.

4. The carboxamide compound of claim 3, in which X is C(O)—$NH_2$.

5. The carboxamide compound as claimed in claim 1, in which $R^1$ is selected from:

$C_3$-$C_{10}$-alkyl which is unsubstituted or may be partly or completely halogenated and/or have 1, 2 or 3 substituents $R^{1a}$, phenyl-$C_1$-$C_4$-alkyl, and hetaryl-$C_1$-$C_4$-alkyl, where phenyl and hetaryl in the last 2 radicals mentioned may be unsubstituted or carry 1, 2, 3 or 4 identical or different radicals $R^{1c}$.

6. The carboxamide compound as claimed in claim 1, in which $R^2$ is selected from:

aryl, and hetaryl, where aryl and hetaryl in the last 2 radicals mentioned may be unsubstituted or carry 1, 2, 3 or 4 identical or different radicals $R^{2b}$.

7. The carboxamide compound of claim 6, in which $R^2$ is phenyl, which is unsubstituted or carries 1, 2, 3 or 4 identical or different radicals $R^{2b}$.

8. The carboxamide compound of claim 1, in which $Y^4$ is N.

9. The carboxamide compound of claim 8, in which $Y^1$, $Y^2$ and $Y^3$ are $CR^Y$, wherein $R^Y$ may be identical or different and are as defined in claim 1.

10. The carboxamide compound of claim 8, in which $Y^1$ is N and $Y^2$ and $Y^3$ are $CR^Y$, or $Y^2$ is N and $Y^1$ and $Y^3$ are $CR^Y$, wherein $R^Y$ may be identical or different and are as defined in claim 1.

11. The carboxamide compound of claim 1, in which $Y^1$, $Y^2$, $Y^3$ and $Y^4$ are $CR^Y$, wherein $R^Y$ may be identical or different and are as defined in claim 1.

12. The carboxamide compound of claim 1, in which $R^{3a}$ and $R^{3b}$ are hydroxy or together with the carbon atom to which they are bonded are C=O.

13. The carboxamide compound of claim 1, which corresponds to the formula I-A, (I-A)

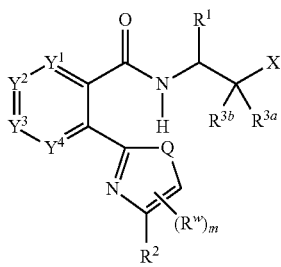

in which m, X, Q, $Y^1$, $Y^2$, $Y^3$, $Y^4$, $R^1$, $R^2$, $R^{3a}$, $R^{3b}$, and $R^w$ have the aforementioned meanings, or a tautomer thereof, or a pharmaceutically suitable salt thereof.

14. The carboxamide compound as claimed of claim 1, which corresponds to the formula I-B, (I-B)

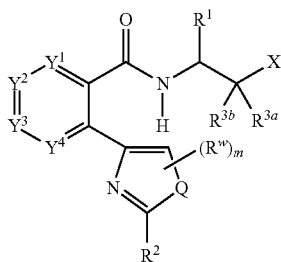

in which m, X, Q, $Y^1$, $Y^2$, $Y^3$, $Y^4$, $R^1$, $R^2$, $R^{3a}$, $R^{3b}$, and $R^w$ have the aforementioned meanings, or a tautomer thereof, or a pharmaceutically suitable salt thereof.

15. The carboxamide compound of claim 1, which corresponds to the formula I-C, (I-C)

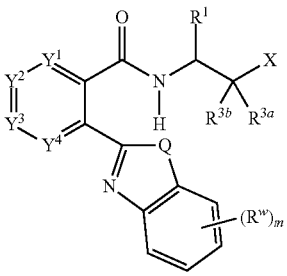

in which m, X, Q, $Y^1$, $Y^2$, $Y^3$, $Y^4$, $R^1$, $R^{3a}$, $R^{3b}$, and $R^w$ have the aforementioned meanings, or a tautomer thereof, or a pharmaceutically suitable salt thereof.

16. The carboxamide compound of claim 1, which corresponds to the formula I-a, (I-a)

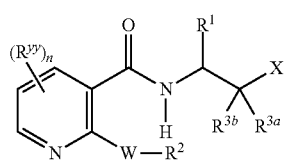

in which X, W, $R^1$, $R^2$, $R^{3a}$, and $R^{3b}$ have the aforementioned meanings, and wherein n is 0, 1 or 2 and $R^{yy}$ has one of the meanings indicated for $R^y$ which are different from hydrogen, or a tautomer thereof, or a pharmaceutically suitable salt thereof.

17. The carboxamide compound of claim 1, which corresponds to the formula I-b, (I-b)

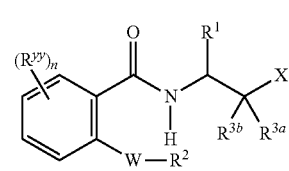

in which X, W, $R^1$, $R^2$, $R^{3a}$, and $R^{3b}$ have the aforementioned meanings, and wherein n is 0, 1 or 2 and $R^{yy}$ has one of the meanings indicated for $R^y$ which are different from hydrogen, or a tautomer thereof, or a pharmaceutically suitable salt thereof.

18. The carboxamide compound of claim 1, which corresponds to the formulae I-c or I-d, (I-c)

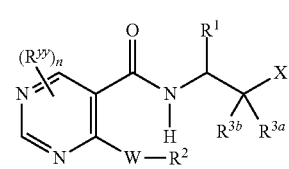

(I-d)

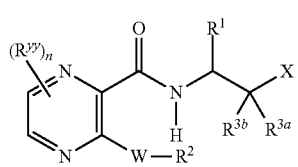

in which X, W, $R^1$, $R^2$, $R^{3a}$, and $R^{3b}$ have the aforementioned meanings, and wherein n is 0, 1 or 2 and $R^{yy}$ has one of the meanings indicated for $R^y$ which are different from hydrogen, or a tautomer thereof, or a pharmaceutically suitable salt thereof.

19. The carboxamide compounds of the formula I-a of claim 16, wherein W is a radical W1.

20. The carboxamide compounds of the formula I-a of claim 16, wherein W is a radical W2.

21. The carboxamide compounds of the formula I-a of claim 16, wherein W—$R^2$ is a radical W3.

22. The carboxamide compound of claim 1, wherein Q is S.

23. The carboxamide compound of claim 1, wherein Q is O or NH.

24. The carboxamide compound of claim 1, which has the S configuration at the carbon atom carrying the group $R^1$.

25. The carboxamide compound of claim 1, which are selected from the group consisting of N-(4-amino-3,4-dioxo-1-phenylbutan-2-yl)-2-(5-phenyl-1H-imidazol-2-yl)pyridine-3-carboxamide;

N-(4-amino-3,4-dioxo-1-phenylbutan-2-yl)-2-[4-(4-fluorophenyl)-1,3-thiazol-2-yl]pyridine-3-carboxamide;

N-(4-amino-3,4-dioxo-1-phenylbutan-2-yl)-2-{4-[3-(trifluoromethyl)phenyl]-1,3-thiazol-2-yl}pyridine-3-carboxamide;

N-(4-amino-3,4-dioxo-1-phenylbutan-2-yl)-2-(4-phenyl-1,3-thiazol-2-yl)pyridine-3-carboxamide;

N-(4-amino-3,4-dioxo-1-phenylbutan-2-yl)-2-[4-(2-chlorophenyl)-1,3-thiazol-2-yl]pyridine-3-carboxamide;

N-(4-amino-3,4-dioxo-1-phenylbutan-2-yl)-2-[4-(naphthalen-2-yl)-1,3-thiazol-2-yl]pyridine-3-carboxamide;

N-(1-amino-1,2-dioxoheptan-3-yl)-2-(4-phenyl-1,3-thiazol-2-yl)nicotinamide;

N-(1-amino-1,2-dioxoheptan-3-yl)-2-(4-phenyl-1,3-thiazol-2-yl)benzamide;

N-(4-amino-3,4-dioxo-1-phenylbutan-2-yl)-2-(4-phenyl-1,3-thiazol-2-yl)benzamide;

N-(4-(Cyclopropylamino)-3,4-dioxo-1-phenylbutan-2-yl)-2-(4-phenyl-1,3-thiazol-2-yl)nicotinamide;

N-(4-(Methoxyamino)-3,4-dioxo-1-phenylbutan-2-yl)-2-(4-phenylthiazol-2-yl)nicotinamide;

N-(4-amino-3,4-dioxo-1-phenylbutan-2-yl)-2-(4-phenyloxazol-2-yl)nicotinamide;

N-(4-amino-3,4-dioxo-1-phenylbutan-2-yl)-2-[2-(4-fluorophenyl)-1,3-thiazol-4-yl]pyridine-3-carboxamide;

N-(4-amino-3,4-dioxo-1-phenylbutan-2-yl)-2-{2-[3-(trifluoromethyl)phenyl]-1,3-thiazol-4-yl}pyridine-3-carboxamide;

N-(4-amino-3,4-dioxo-1-phenylbutan-2-yl)-2-(2-phenyl-1,3-thiazol-4-yl)pyridine-3-carboxamide;

N-(4-amino-3,4-dioxo-1-phenylbutan-2-yl)-2-[2-(2-chlorophenyl)-1,3-thiazol-4-yl]pyridine-3-carboxamide;

N-(4-amino-3,4-dioxo-1-phenylbutan-2-yl)-2-[2-(naphthalen-2-yl)-1,3-thiazol-4-yl]pyridine-3-carboxamide;

N-(1-amino-1,2-dioxoheptan-3-yl)-2-(2-phenylthiazol-4-yl)nicotinamide;

N-(1-amino-1,2-dioxoheptan-3-yl)-2-(2-phenyl-1,3-thiazol-4-yl)benzamide;

N-(4-amino-3,4-dioxo-1-phenylbutan-2-yl)-2-(2-phenyl-1,3-thiazol-4-yl)benzamide;

N-(4-(Cyclopropylamino)-3,4-dioxo-1-phenylbutan-2-yl)-2-(2-phenylthiazol-4-yl)nicotinamide;

N-(4-(Methoxyamino)-3,4-dioxo-1-phenylbutan-2-yl)-2-(2-phenylthiazol-4-yl)nicotinamide;

N-(4-amino-3,4-dioxo-1-phenylbutan-2-yl)-2-(2-phenyloxazol-4-yl)nicotinamide;

N-(4-amino-3,4-dioxo-1-phenylbutan-2-yl)-2-(1H-benzimidazol-2-yl)pyridine-3-carboxamide;

N-(4-amino-3,4-dioxo-1-phenylbutan-2-yl)-2-(1,3-benzothiazol-2-yl)pyridine-3-carboxamide; and N-(4-amino-3,4-dioxo-1-phenylbutan-2-yl)-2-(1,3-benzo[d]oxazol-2-yl)pyridine-3-carboxamide;

or a tautomer thereof, or a pharmaceutically suitable salt thereof.

26. A medicament comprising at least one carboxamide compound of claim 1, a tautomer or a pharmaceutically suitable salt thereof, and one or more suitable excipients/drug carriers.

* * * * *